US012577304B2

(12) United States Patent
Smith et al.

(10) Patent No.: US 12,577,304 B2
(45) Date of Patent: **\*Mar. 17, 2026**

(54) ANTI-CD3 ANTIBODIES WITH LOW BINDING AFFINITY

(71) Applicant: Regeneron Pharmaceuticals, Inc., Tarrytown, NY (US)

(72) Inventors: Eric Smith, New York, NY (US); Lauric Haber, Rye Brook, NY (US); Robert Babb, River Edge, NJ (US); Gang Chen, Yorktown Heights, NY (US); Douglas MacDonald, New York, NY (US)

(73) Assignee: Regeneron Pharmaceuticals, Inc., Tarrytown, NY (US)

( \* ) Notice: Subject to any disclaimer, the term of this patent is extended or adjusted under 35 U.S.C. 154(b) by 206 days.

This patent is subject to a terminal disclaimer.

(21) Appl. No.: 17/207,462

(22) Filed: Mar. 19, 2021

(65) Prior Publication Data

US 2021/0253701 A1 Aug. 19, 2021

Related U.S. Application Data

(63) Continuation of application No. 15/780,504, filed as application No. PCT/US2016/053525 on Sep. 23, 2016, now abandoned.

(60) Provisional application No. 62/222,605, filed on Sep. 23, 2015.

(51) Int. Cl.
| | |
|---|---|
| *C07K 16/28* | (2006.01) |
| *A61P 35/00* | (2006.01) |
| *C07K 16/30* | (2006.01) |
| *C07K 16/40* | (2006.01) |
| *C07K 16/46* | (2006.01) |
| *A61K 39/00* | (2006.01) |

(52) U.S. Cl.
CPC .......... *C07K 16/2809* (2013.01); *A61P 35/00* (2018.01); *C07K 16/2863* (2013.01); *C07K 16/3069* (2013.01); *C07K 16/40* (2013.01); *C07K 16/468* (2013.01); *A61K 2039/505* (2013.01); *C07K 2317/31* (2013.01); *C07K 2317/55* (2013.01); *C07K 2317/92* (2013.01)

(58) Field of Classification Search
CPC .................................................. C07K 16/2809
USPC ...................................................... 424/136.1
See application file for complete search history.

(56) References Cited

U.S. PATENT DOCUMENTS

| | | |
|---|---|---|
| 5,624,821 A | 4/1997 | Winter et al. |
| 5,648,260 A | 7/1997 | Winter et al. |
| 6,180,377 B1 | 1/2001 | Morgan et al. |
| 7,396,917 B2 | 7/2008 | Bowdish et al. |
| 7,563,441 B2 | 7/2009 | Graus et al. |
| 7,597,889 B1 | 10/2009 | Armour et al. |
| 7,608,260 B2 | 10/2009 | Schenerman et al. |
| 7,700,097 B2 | 4/2010 | Braslawsky et al. |
| 7,700,099 B2 | 4/2010 | Strohl |
| 7,728,114 B2 | 6/2010 | Mach et al. |
| 7,820,166 B2 | 10/2010 | Lanzavecchia et al. |
| 7,824,684 B2 | 11/2010 | Graus et al. |
| 7,867,491 B2 | 1/2011 | Yang et al. |
| 7,960,512 B2 | 6/2011 | Stavenhagen et al. |
| 8,075,884 B2 | 12/2011 | Bowdish et al. |
| 8,084,026 B2 | 12/2011 | Glaser et al. |
| 8,153,583 B2 | 4/2012 | Carton et al. |
| 8,236,314 B2 | 8/2012 | Kai et al. |
| 8,268,972 B2 | 9/2012 | Whitfeld et al. |
| 8,383,109 B2 | 2/2013 | Lazar et al. |

(Continued)

FOREIGN PATENT DOCUMENTS

| | | |
|---|---|---|
| EP | 2327378 B1 | 12/1996 |
| EP | 2447372 A2 | 5/2012 |

(Continued)

OTHER PUBLICATIONS

Chiu et al (Cancer Immunol Res 8(5):596-608; May 1, 2020).\*

(Continued)

*Primary Examiner* — Lynn A Bristol

(74) *Attorney, Agent, or Firm* — Schwabe, Williamson & Wyatt PC; Aparna Patankar

(57) ABSTRACT

The present invention provides antibodies that bind to CD3 with weak or no detectable binding affinity and methods of using the same. According to certain embodiments, the antibodies of the invention bind human CD3 with low affinity and induce human T cell proliferation and hence induce T cell-mediated killing of tumor cells with high efficacy. According to certain embodiments, the present invention provides bispecific antigen-binding molecules comprising a first antigen-binding domain that specifically binds human CD3 with weak or no detectable binding affinity in an in vitro assay, and a second antigen-binding molecule that specifically binds human tumor-associated antigen. In certain embodiments, the bispecific antigen-binding molecules of the present invention are capable of inhibiting the growth of tumors expressing target antigen, such as PSMA. The antibodies and bispecific antigen-binding molecules of the invention are useful for the treatment of diseases and disorders in which an upregulated or induced targeted immune response is desired and/or therapeutically beneficial. For antibodies of the invention are useful for the treatment of various cancers or other diseases where immunotherapy, including effector cell immunomodulation, is warranted.

9 Claims, 5 Drawing Sheets

Specification includes a Sequence Listing.

(56) References Cited

U.S. PATENT DOCUMENTS

| | | | |
|---|---|---|---|
| 8,409,568 B2 | 4/2013 | Gao et al. | |
| 8,597,648 B2 | 12/2013 | Guo et al. | |
| 8,961,967 B2 | 2/2015 | Strohl et al. | |
| 9,359,437 B2 | 6/2016 | Davis et al. | |
| 10,106,610 B2 | 10/2018 | Davis et al. | |
| 10,179,819 B2 * | 1/2019 | Kirshner | A61P 35/00 |
| 10,421,804 B2 | 9/2019 | Kyratsous et al. | |
| 10,556,952 B2 | 2/2020 | Davis et al. | |
| 10,738,130 B2 * | 8/2020 | Haber | C07K 16/44 |
| 10,772,972 B2 * | 9/2020 | Rudge | C07K 16/2809 |
| 10,941,208 B2 * | 3/2021 | Haber | A61K 47/6869 |
| 10,988,537 B2 | 4/2021 | Davis et al. | |
| 11,117,955 B2 | 9/2021 | Kyratsous et al. | |
| 11,155,633 B2 * | 10/2021 | Kirshner | A61P 35/00 |
| 11,485,793 B2 * | 11/2022 | Haber | C07K 16/44 |
| 11,518,807 B2 | 12/2022 | Davis et al. | |
| 11,590,223 B2 | 2/2023 | Brownstein et al. | |
| 11,633,501 B2 * | 4/2023 | Rudge | C07K 16/40 |
| | | | 424/181.1 |
| 11,952,430 B2 * | 4/2024 | Haber | C07K 16/2818 |
| 12,054,557 B2 | 8/2024 | Varghese et al. | |
| 12,065,508 B2 * | 8/2024 | Haber | C07K 14/7051 |
| 12,077,603 B2 * | 9/2024 | Haber | C07K 16/2818 |
| 2004/0171123 A1 | 9/2004 | Rosen et al. | |
| 2005/0037000 A1 | 2/2005 | Stavenhagen et al. | |
| 2005/0226876 A1 | 10/2005 | Graus et al. | |
| 2005/0244403 A1 | 11/2005 | Lazar et al. | |
| 2006/0134709 A1 | 6/2006 | Stavenhagen et al. | |
| 2007/0009523 A1 | 1/2007 | Presta | |
| 2007/0041972 A1 | 2/2007 | Rother et al. | |
| 2009/0117133 A1 | 5/2009 | Arnason et al. | |
| 2009/0162901 A1 | 6/2009 | Chen et al. | |
| 2009/0252729 A1 | 10/2009 | Farrington et al. | |
| 2010/0108574 A1 | 5/2010 | Ouriev et al. | |
| 2010/0166749 A1 | 7/2010 | Presta | |
| 2010/0267934 A1 | 10/2010 | Winkel et al. | |
| 2010/0298542 A1 | 11/2010 | Igawa et al. | |
| 2010/0325744 A1 | 12/2010 | Schuurman et al. | |
| 2010/0331527 A1 | 12/2010 | Davis et al. | |
| 2011/0077383 A1 | 3/2011 | Dall'Acqua et al. | |
| 2011/0212087 A1 | 9/2011 | Strohl et al. | |
| 2011/0245473 A1 | 10/2011 | Igawa et al. | |
| 2011/0263830 A1 | 10/2011 | Goetsch et al. | |
| 2011/0293607 A1 | 12/2011 | Labrijn et al. | |
| 2012/0065379 A1 | 3/2012 | Igawa et al. | |
| 2012/0071634 A1 | 3/2012 | Igawa et al. | |
| 2012/0100140 A1 | 4/2012 | Reyes et al. | |
| 2012/0189643 A1 | 7/2012 | Carton et al. | |
| 2012/0225058 A1 | 9/2012 | Lazar et al. | |
| 2012/0237515 A1 | 9/2012 | Bell et al. | |
| 2012/0237829 A1 | 9/2012 | Kuramochi et al. | |
| 2012/0251531 A1 | 10/2012 | Baehner et al. | |
| 2012/0276096 A1 | 11/2012 | Yang et al. | |
| 2012/0276097 A1 | 11/2012 | Yang et al. | |
| 2013/0011386 A1 | 1/2013 | Brerski et al. | |
| 2013/0101581 A1 | 4/2013 | Kuramochi et al. | |
| 2013/0108623 A1 | 5/2013 | D'Angelo et al. | |
| 2013/0129723 A1 | 5/2013 | Blankenship et al. | |
| 2013/0251707 A1 | 9/2013 | Kontermann et al. | |
| 2014/0088295 A1 | 3/2014 | Smith et al. | |
| 2014/0112914 A1 | 4/2014 | Nezu et al. | |
| 2014/0120581 A1 | 5/2014 | Niwa et al. | |
| 2015/0166661 A1 | 6/2015 | Chen et al. | |
| 2015/0203579 A1 | 7/2015 | Papadopoulos et al. | |
| 2016/0130347 A1 | 5/2016 | Bruenker et al. | |
| 2016/0168247 A1 | 6/2016 | Van Den Brink et al. | |
| 2016/0347839 A1 | 12/2016 | Davis et al. | |
| 2017/0008951 A1 | 1/2017 | Block et al. | |
| 2017/0051074 A1 | 2/2017 | Kirshner et al. | |
| 2018/0104357 A1 | 4/2018 | Rudge et al. | |
| 2018/0112001 A1 | 4/2018 | Haber et al. | |
| 2018/0118848 A1 | 5/2018 | Haber et al. | |
| 2018/0303953 A1 | 10/2018 | Van Berkel et al. | |
| 2018/0355038 A1 * | 12/2018 | Smith | C07K 16/3069 |
| 2019/0127480 A1 | 5/2019 | Kirshner et al. | |
| 2019/0389966 A1 | 12/2019 | Crawford | |
| 2020/0317810 A1 | 10/2020 | Haber et al. | |
| 2021/0403595 A1 * | 12/2021 | Kirshner | C07K 16/2809 |
| 2024/0368312 A1 * | 11/2024 | Haber | C07K 16/2818 |

FOREIGN PATENT DOCUMENTS

| | | | |
|---|---|---|---|
| EP | 2918604 A1 | 9/2015 | |
| WO | 97/028267 A1 | 8/1997 | |
| WO | 99/043713 A1 | 9/1999 | |
| WO | 99/058572 A1 | 11/1999 | |
| WO | 00/042072 A2 | 7/2000 | |
| WO | 03/026490 A2 | 4/2003 | |
| WO | 08/147143 A2 | 12/2008 | |
| WO | 10/054212 A1 | 5/2010 | |
| WO | 10/063785 A2 | 6/2010 | |
| WO | 10/085682 A2 | 7/2010 | |
| WO | 11/137362 A1 | 11/2011 | |
| WO | 11/163566 A1 | 12/2011 | |
| WO | 12/022982 A2 | 2/2012 | |
| WO | 12/035141 A1 | 3/2012 | |
| WO | 12/073985 A1 | 6/2012 | |
| WO | 12/087746 A1 | 6/2012 | |
| WO | 13/012733 A1 | 1/2013 | |
| WO | 13/026839 A1 | 2/2013 | |
| WO | 13/112986 A1 | 8/2013 | |
| WO | 13/157105 A1 | 10/2013 | |
| WO | 13/184761 A1 | 12/2013 | |
| WO | 14/012085 A2 | 1/2014 | |
| WO | 14/022540 A1 | 2/2014 | |
| WO | 14/047231 A1 | 3/2014 | |
| WO | 14/051433 A1 | 4/2014 | |
| WO | 14/056783 A1 | 7/2014 | |
| WO | 14/121087 A1 | 8/2014 | |
| WO | 15/006749 A2 | 1/2015 | |
| WO | 15/091738 A1 | 6/2015 | |
| WO | 15/143079 A1 | 9/2015 | |
| WO | 16/161010 A2 | 10/2016 | |
| WO | 17/053856 A1 | 3/2017 | |
| WO | 21/021469 A1 | 2/2021 | |

OTHER PUBLICATIONS

Vajda et al., Current Opinion in Structural Biology, 67 pp. 226-231 (2021).*

Marks et al., J. Biol. Chem. 295(29) 9823-9837 (2020 ).*

Akbar et al., Cell Reports 34, 108856, Mar. 16, 2021).*

Lo et al., BMC Genomics vol. 22, Article No. 116.*

Chiu et al (Antibodies (Basel). Dec. 2019; 8(4):1-80; Published online Dec. 3, 2019).*

"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605 pdf >].

"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].

Aalberse et al., "IgG4 breaking the rules," Immunology, 105(1):9-19, (2002).

Advani et al., "New immune strategies for the treatment of acute lymphoblastic leukemia: antibodies and chimeric antigen receptors," Hematology, vol. 2013 (No. 1): (Dec. 1, 2013).

Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).

Almagro et al., "Humanization of antibodies," Front Biosci, vol. 13, pp. 1619-163, (2008).

An et al., "IgG2m4, an engineered antibody isotype with reduced Fc function," Landes Bioscience, 1(6):572-579, (2009).

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved

(56)        References Cited

OTHER PUBLICATIONS from the Internet Mar. 14, 2017: <URL: https://www.clinicaltrailsregister. eu/ctr- search/trial/2015-001697-17/ES>].
Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials. com/trialpage?dcn=10963&city=Baltimore&country=UnitedStates &start=20&state=Maryland&conditions=lymphoma&id= 207048402254>].
Armour et al., "Differential binding to human FcyRlla and FcyRIIb receptors by human IgG wildtype and mutant antibodies," Molecular Immunology, 40:585-593, (2003).
Armour et al., "Recombinant human IgG molecules lacking Fcy receptor I binding and monocyte triggering activities", J. Immunol., 29:2613-2624, (1999).
Bae et al., "Identification of the amino acid residues involved in human IgG transport into egg yolk of Japanese quail," Molucular Immunology, vol. 47:1404-1410, (2010).
Baeuerle et al., "Bispecific T-cell engaging antibodies for cancer therapy," Cancer Res, 69(12): 4941-4944, doi: 10.1158/0008-5472. CAN-09-0547, (2009).
Bargou et al., "Tumor egression in Cancer Patients by Very Low Doses of a T Cell-Engaging Antibody," Science Magazine, vol. 321: 974-977, (2008).
Becker et al., "Evaluation of a combinatorial cell engineering approach to overcome apoptotic effects in XBP-1(s) expressing cells," Journal of Biotechnology, vol. 164:198-206, (2010).
Bloom et al., "Intrachain disulfide bond in the core hinge region of human IgG4," Protein Science, 6:407-415, (1997).
Brekke et al., "The structural requirements for complement activation by IgG: does it hinge on the hinge?" Today, 16(2):85-90, (1995).
Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).
Bortoletto et al., "Optimizing anti-CD3 affinity for effective T cell targeting against tumor cells," Eur. J. Immunol, vol. 32:3102-3107 (2002).
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www. translational-medicine.com/content/11/1/1160>].
Canfield et al., "The Binding Affinity of Human IgG for Its High Affinity Fc Receptor is Determined by Multiple Amino Acids in the $C_H2$ Domain and is Modulated by the Hinge Region," J. Exp. Med., 173(6):1483-1491, (1991).
Cao et al., "Multiformat T-Cell-Engaging Bispecific Antibodies Targeting Human Breast Cancers," Angew Chem Int Ed Engl, 54(24):7022-7027, doi: 10.1002/anie.201500799, (2015).
Chan et al., "Therapeutic antibodies for autoimmunity and inflammation," Macmillan Publishers Limited (Nature Reviews, Immunology), vol. (10):301-316, (2010).
Chappel et al., "Identification of a Secondary FcyRI Binding Site within a Genetically Engineered Human IgG," Journal of Biological Chemistry, 268(33): 25124-25131, (1993).
Chappel et al., "Identification of the FC-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Clark, "IgG Effector Mechanisms," Chem Immunol. Basel, Karger, 65:88-110, (1997).
Dall'Acqua et al., "Modulation of the Effector Functions of a Human IgG1 through Engineering of Its Hinge Region," Journal of Immunology, 177:1129-1138, (2006).

Damschroder et al., "Analysis of human and primate CD2 molecules by protein sequence and epitope mapping with anti-human CD2 antibodies," Molecular Immunology, vol. 41:985-1000, (2004).
Dangl et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on IgG", Nature, 332:563-564, (1988).
Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).
Gergely et al., "The two binding-site models of human IgG binding Fcy receptors," The FASEB Journal, 4:3275-3283, (1990).
Greenwood et al., "Structural Motifs Involved In Human IGG Antibody Effector Functions," Eur. J. Immunology, 23(5):1098-1104, (1993).
Grubb, "Human immunoglobulin allotypes and Mendelian polymorphisma of the human immunoglobulin genes," Oss CJ, Regenmortel MHV (eds): Immunochemistry, New York, Dekker; pp. 47-68 (1994).
Harlow et al., Antibodies, A Laboratory Manual, Cold Spring Harbor Laboratory; (1998) pp. 37-47.
Haso et al., "Anti-CD22-chimeric antigen receptors targeting B-cell precursor acute lymphoglastic leukemia," Blood, vol. 121 (No. 7):1165-1174, Feb. 14, 2013.
Hezareh et al., "Effector function activities of a panel of mutants of a broadly neutralizing antibody against human immunodeficiency virus type 1," J Virol, 75(24):12161-12168, doi: 10.1128/JVI.75. 24.12161-12168.2001, (2001).
Jacobsen et al., "Molecular and Functional Characterization of Cynomolgus Monkey IgG Subclasses," Journal Immunology, 186:341-349, (2011).
Jefferis et al., "Interaction sites on human IgG-Fc for FcyR: current models", Immunology Letters, 82:57-65, (2002).
Jefferis et al., "Recognition sites on human IgG for Fcy receptors: the role of glycosylation," Immunology Letters, 44:111-117, (1995).
Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Kapur et al., "IgG-effector functions: The Good, The Bad and The Ugly," El Sevier, vol. 160:139-144, (2014).
Kohnke et al., "Increase of PD-L1 expressing B-precursor ALL cells in a patient resistant to the CD19/CD3-bispecific T cell engager antibody blinatumomab," Journal of Hematology & Oncology, vol. 8 (No. 111): 5 pages, (2015).
Kumar et al., "Expression of CD20 in B Cell Precursor Acute Lymphoblastic Leukemia," Indian J Hematol Blood Transfus, vol. 30 (No. 1):16-18, (2014).
Labrijn et al., "When binding is enough: nonactivating antibody formats", Current Opinion in Immunology, 20:479-485, (2008).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).
Li et al., "A Novel Bispecific Antibody, S-Fab, Induces Potent Cancer Cell Killing," J Immunother, 38(9):350-356, doi: 10.1097/ CJI.0000000000000099, (2015).
Lum et al., "CD2O-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Published online Sep. 23, 2013].
Lund et al., "Human FcyRI and FcyRII Interact with Distinct but Overlapping Sites on Human IgG", Journal of Immunology, 147(8):2657-2662, (1991).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).

(56) References Cited

OTHER PUBLICATIONS

Morgan et al., "The N-terminal end of the CH2 domain of chimeric human IgG1 anti-HLA-DR is necessary for Gig, FcγRI and FcγRII binding," Immunology, 86:319-324, (1995).

Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).

Natsume et al., "Engineered Antibodies of IgG1|IgG3 Mixed Isotype with Enhanced Cytotoxic Activities," Cancer Research, 68:(10):3863-3872, (2008).

NCBI MedGen 44126 definition for "Pre-B Acute Lumphoblastic Leukemia"; retrieved from the Internet on Dec. 11, 2018, pp. 1-4, available at <https://www.ncbi.nlm.nih.gov/medgen/44126/> (2018).

Oganesyan et al., "Structural characterization of a human Fc fragment engineered for lack of effector functions," Acta Crystallographica Section D Biological Crystallography, D64:700-704, (2008).

Ontology Lookup Service, EFO 0000220, "acute lumphoblastic leukemia", retrieved from the Internet on Dec. 11, 2018, pp. 1-6, available at <https://www.ebi.ac.uk/ols/ontologies/efo/terms?short_form=EFO_0000220> (2018).

Patel et al., "IGG subclass variation of a monoclonal antibody binding to human Fc-gamma receptors", American Journal of Biochemistry and Biotechnology, 9(3):206-218, (2013).

Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).

Reddy et al., "Elimination of Fc Receptor-Dependent Effector Functions of a Modified IgG4 Monoclonal Antibody to Human CD4," Journal of Immunology, 164:1925-1933, (2000).

Richards et al., "Optimization of antibody binding to FcγRIIa enhances macrophage phagocytosis of tumor cells," Molecular Cancer Therapeutics (Xencor, Inc.), vol.(8):2517-2527, (2008). [Retrieved from the Internet Sep. 16, 2020: <URL: met.aacrjournals.org>].

Rother et al., : "Discovery and development of the complement inhibitor eculizumab for the treatment of paroxysmal nocturnal hemoglobinuna," Nature Biotechnology, 25(11):1256-1264, (2007).

Roux et al., "Comparisons of the ability of human IgG3 hinge mutants, IgM, IgE and IgA2, to form small immune complexes: Arole for flexibility and geometry," The Journal of Immunology, 161:4083-4090, (1998).

Roux et al., "Flexibility of Human IgG Subclasses," Journal of Immunology, 159:3372-3382, (1997).

Ruf et al., "Induction of a long-lasting antitumor immunity by a trifunctional bispecific antibody," Blood Journal, vol. 98, No. 9: 2526-2534, (2001).

Salfeld, "Isotype selection in antibody engineering," Nature Biotechnology, 25(12):1369-1372, (2007).

Sarmay et al., "Mapping and Comparison of the Interaction Sites on the Fc Region of IgG Responsible for Triggering Antibody Dependent Cellular Cytotoxicity (ADCC) through Different Types of Human Fcγ Receptor," Molecular Immunology, 29(5):633-639, (1992).

Sathish et al., "Challenges and approaches for the development of safer immunomodulatory biologics," Nature Reviews Drug Discovery, 12:306-324, (2013).

Schaefer et al., "Immunoglobulin domain crossover as a generic approach for the production of bispecific IgG antibodies," PNAS, 108(27):11187-11192, doi: 10.1073/pnas.1019002108, (2011).

Schuster et al., "Immunotherapy with the trifunctional anti-CD20 x anti-CD3 antibody FBTA05 Lymphomun) in pediatric high-risk patients with recurrent CD20-positive B cell malignancies," British Journal of Haematolgy, vol. 169 (No. 1): (Apr. 11, 2015); pp. 90-102.

Sensel et al., "Amino Acid Differences in the N-Terminus of CH2 Influence the Relative Abilities of IgG2 and IgG3 to Activate Complement", Molecular Immunology, 34(14): 1019-1029, (1997).

Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).

Siberil et al., "Molecular aspects of human FcγR interactions with IgG: Functional and therapeutic consequences," Immunology Letters, 106:111-118, (2006).

Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.

Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).

Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).

Stevenson, "Chemical Engineering at the Antibody Hinge," Chem Immunol. Basel, Karger, 65:57-72, (1997).

Strop et al., "Generating Bispecific Human IgG1 and IgG2 Antibodies from Any Antibody Pair", J. Mol. Biol., 420(3):204-219, (2012).

Sun et al., "Anti-CD20/CD3 T cell-dependent bispecific antibody for the treatment of B cell malignancies," Science Translational Medicine, 7(287):287ra70, 10 pages, (2015).

Sun, "Structural Recognition of Immunoglobulins by Fc γ Receptors," Elsevier Science & Technology, Ch. 7:131-144, (2013).

Tan et al., "Influence of the hinge region on complement activation, C1q binding, and segmental flexibility in chimeric human immunoglobulins,", Proc. Natl. Acad. Sci. USA, 87:162-166, (1990).

Thomas et al., "Chemoimmunotherapy with a Modified Hyper-CVAD and Rituximab Regimen Improves Outcome in De Novo Philadelphia Chromosome-Negative Precursor B-Lineage Acute Lymphoblastic Leukemia," Journal of Clinical Oncology, vol. 28 (No. 24):3880-3889; Aug. 20, 2010.

Topp et al., "Safety and activity of blinatumomab for adult patients with relapsed or refractory B-precursor acute lymphoblastic leukemia: a multicentre, single-arm, phase 2 study," Publication, vol. 16:57-66, (Jan. 2015).

Tsai et al., "Regulation of CD20 in Rituximab-Resistant Cell Lines and B-cell Non-Hodgkin Lymphoma," Clinical Cancer Research, vol. 18(No. 4):1039-1050, (2012).

U.S. Appl. No. 15/562,881, Notice of Allowance mailed Jun. 12, 2019.

U.S. Appl. No. 15/562,881, Notice of Allowance mailed Sep. 25, 2019.

U.S. Appl. No. 14/170,166, Non-Final Office Action mailed Dec. 21, 2015.

U.S. Appl. No. 14/170,166, Notice of Allowance mailed Apr. 11, 2016.

U.S. Appl. No. 14/170,166, Requirement for Restriction/Election mailed Jul. 27, 2015.

U.S. Appl. No. 15/147,791, Non-Final Office Action mailed Sep. 27, 2017.

U.S. Appl. No. 15/147,791, Notice of Allowance mailed Mar. 1, 2018.

U.S. Appl. No. 15/147,791, Notice of Allowance mailed Jun. 12, 2018.

U.S. Appl. No. 15/780,504, Requirement for Restriction/Election mailed Apr. 7, 2020.

U.S. Appl. No. 16/128,907, Non-Final Office Action mailed Sep. 22, 2020.

U.S. Appl. No. 15/780,504, Non-Final Office Action mailed Oct. 20, 2020.

U.S. Appl. No. 16/128,907, Notice of Allowance mailed Dec. 31, 2020.

Vafa, et al., "An engineered Fc variant of an IgG eliminates all immune effector functions via structural perturbations", 65:114-126, (2014). (Published online Jul. 17, 2013).

(56) References Cited

OTHER PUBLICATIONS

Vidarsson et al., "IgG Subclasses and Allotypes: From Structure to Effector Functions," Frontiers in Immunology, vol. 5, Article 520, 18 pages, doi: 10.3389/fimmu.2014.00520, (2014).

Ward et al., "The effector functions of immunoglobulins: implications for therapy," Therapeutic Immunology, 2:77-94, (1995).

Weinglass et al., "Engineering Conformational Flexibility in the Lactose Permease of *Escherichia coli*: Use of Glycine-Scanning Mutagenesis to Rescue Mutant Glu325—Asp," Biochemistry, vol. 40:769-776, (2001).

WIPO Application No. PCT/US2014/014175, PCT International Preliminary Report on Patentability mailed Aug. 13, 2015.

WIPO Application No. PCT/US2014/014175, PCT International Search Report and Written Opinion of the International Searching Authority mailed Jul. 9, 2014.

WIPO Application No. PCT/US2016/025051, PCT International Search Report and Written Opinion of the International Searching Authority mailed Oct. 12, 2016.

WIPO Application No. PCT/US2016/053525, PCT International Search Report and Written Opinion of the International Searching Authority mailed Mar. 8, 2017.

Wu et al., "Fab-based bispecific antibody formats with robust biophysical properties and biological activity," MABS, pp. 470-482, ISSN: 1942-0870, (2015).

Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).

Wypych et al., "Human IgG2 Antibodies Display Disulfide-mediated Structural Isoforms," Journal of Biological Chemistry, 283(23):16194-16205, (2008).

Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).

Bannerji et al., "Phase 1 Study of REGN1979, an Anti-CD20 x Anti-CD3 Bispecific Monoclonal Antibody, in Patients with CD20+ B-Cell Malignancies Previously Treated with CD20-Directed Antibody Therapy," Blood, vol. 128 (22): 621 (2016). [http://doi.org/10.1182/blood.V128.22.621.621].

U.S. Appl. No. 16/720,623, Requirement for Restriction/Election mailed Sep. 15, 2021.

U.S. Appl. No. 16/720,623, Non-Final Office Action mailed Feb. 14, 2022.

U.S. Appl. No. 16/556,885, Non-Final Office Action mailed Mar. 29, 2022.

U.S. Appl. No. 16/720,623, Notice of Allowance mailed Jul. 7, 2022.

U.S. Appl. No. 17/217,567, Non-Final Office Action mailed Mar. 31, 2023.

Varghese et al., "A Novel CD20-CD3 Bispecific Fully Human Antibody Induces Potent Anti-Tumor Effects Against B Cell Lymphoma in Mice," Blood, vol. 124 (21) 4501 (2014). [http://doi.org/10.1182/blood.V124.21.4501.4501].

Frey et al., "Cytokine release syndrome: Who is at risk and how to treat," Best Practice & Research Clinical Haematology, vol. 30 (No. 4): 336-340, (Dec. 2017). [Retrieved from the Internet Sep. 11, 2023: <URL: https://www.sciencedirect.com/journal/best-practice-and-research-clinical-haematology>].

U.S. Appl. No. 17/217,567, Final Office Action mailed Aug. 11, 2023.

U.S. Appl. No. 17/217,567, Non-Final Office Action mailed Nov. 29, 2023.

U.S. Appl. No. 17/217,567, Final Office Action mailed Mar. 7, 2024.

Chao et al. (Cancer Management and Research 2013:5 251-269). (Year: 2013).

P01834 (GenPept, Ig kappa chain C region, pp. 1-4, Feb. 19, 2014). (Year: 2014).

U.S. Appl. No. 17/207,462, Final Office Action mailed Dec. 9, 2024.

U.S. Appl. No. 17/961,442, Non-Final Office Action mailed Mar. 3, 2025.

U.S. Appl. No. 17/217,567, Final Office Action mailed Apr. 14, 2025.

U.S. Appl. No. 17/875,295, Non-Final Office Action mailed Mar. 13, 2025.

Wong et al. (Haematologica. Dec. 2013 98(12):1930-1938, supplemental pages included, document has been renumbered as pp. 1-27). (Year: 2013).

* cited by examiner

ANTI-CD3 ANTIBODIES WITH LOW BINDING AFFINITY

CROSS-REFERENCE TO RELATED APPLICATIONS

This Application is a continuation of U.S. application Ser. No. 15/780,504, filed May 31, 2018, which is a US National Stage Application under 35 USC § 371 of PCT/US2016/053525, filed Sep. 23, 2016, which claims the benefit under 35 USC § 119 (e) of U.S. Provisional Patent Application No. 62/222,605, filed Sep. 23, 2015, each of which is herein incorporated by reference in its entirety.

REFERENCE TO A SEQUENCE LISTING

This application incorporates by reference the Sequence Listing submitted in Computer Readable Form as file 10151WO01_ST25.txt, created on Sep. 22, 2016 and containing 264,418 bytes.

FIELD OF THE INVENTION

The invention related to bispecific antibodies, targeting an effector antigen, such as CD3 antigen, and a tumor associated antigen, and methods of tumor killing. The invention relates to methods of reducing or eliminating tumor burden and controlling the toxic side effects that may be associated with tumor immunotherapy. The present invention provides bispecific antibodies comprising an effector arm which binds to an effector antigen with weak affinity or with no detectable binding affinity, for example, an anti-CD3 antigen-binding arm which binds to CD3 with a KD of greater than about 500 nM, in an in vitro affinity binding assay.

BACKGROUND

The promise of therapeutic bispecific antibodies (bsAbs), particularly in cancer immunotherapies, aims to bridge multiple antigen targets in order to elicit a more robust innate immune response to the unwanted target-bearing cells or organism.

It is now well established that to mediate redirected lysis, a bsAb must cluster a target cell directly to a triggering molecule on an effector cell, such as a T cell. There are many factors to consider in bsAb design, for example, size and composition will affect biodistribution and stability in vivo (Segal, DM, Weiner, G J, and Weiner, LM. Current Opinion in Immunol 1999, 11:558-562; Chames, P. and Baty, D. MAbs. 2009, 1 (6): 539-547). Differential outcomes are difficult to predict depending on the T cell subset being triggered to respond, as well as the state of the T cell being stimulated. It is well-known that bsAbs do not give consistent results (Manzke O, et al. Cancer Immunol Immunother. 1997, 45:198-202). For example, without adequate cytokine production, CD3 crosslinking can induce an apoptotic response in the T cell (Noel PJ, Boise LH, Thompson CB: Regulation of T cell activation by CD28 and CTLA4. Adv Exp Med Biol 1996, 406:209-217). The subset of T cells and differentiation state of such recruited T cells, e.g. naïve T cells, are important for efficacy, since naïve T cells cannot lyse target cells without preactiviation (such as crosslinking with TCR in the presence of IL-2).

Certain bispecific therapies have been successful, yet, as with many cancer therapies, it comes with a price. Toxicity is the leading cause of failure among cancer therapeutics. It is well known that toxicity of so-called chemotherapeutic drugs is the leading cause of patient side effects and secondary maladies. The act of "cell killing" itself is wrought with trouble for the patient. A plethora of cytotoxic responses can be induced by activation of effector cells e.g. T cells, and a cancer target cell, yet which type of response is most beneficial in tumor immunotherapy remains to be seen. A method of identifying anti-CD3 antibodies for use in a bispecific therapy having reduced side effects while maintaining efficacy and desirable pharmacokinetic (PK) properties would be advantageous.

Techniques such as affinity maturation have been described which, based on structure/activity relationship (SAR), utilize mutagenesis to optimize antibodies to have increased and improved binding specificity or affinity for a target antigen compared to the starting antibody (see, e.g. WO2011056997, published May 12, 2011). Modified OKT3 antibodies capable of binding to and interacting with CD3 with varying degrees of affinity while still exhibiting moderate to high T cell activation have been described (U.S. Pat. No. 7,820,166). However, methods of reducing binding affinity of antibody molecules to near or beyond the detectable level of binding have not been described, nor shown to have the requisite efficacy for tumor reduction or suppression.

Thus, there exists a need for alternative bispecific antigen-binding molecules having controlled cytotoxicity and better PK properties. Such cancer therapies would be quite useful in therapeutic settings.

BRIEF SUMMARY OF THE INVENTION

In a first aspect, the present invention provides antibodies and antigen-binding fragments thereof that bind human CD3 having weak or no detectable affinity for human and/or cynomolgus CD3. The antibodies according to this aspect of the invention are useful, inter alia, for targeting T cells expressing CD3, and for stimulating T cell activation, e.g., under circumstances where T cell-mediated killing is beneficial or desirable. The anti-CD3 antibodies of the invention, or antigen-binding portions thereof, may be included as part of a bispecific antibody that directs CD3-mediated T cell activation to specific cell types such as tumor cells or infectious agents.

Exemplary anti-CD3 antibodies of the present invention are listed in Tables 2 and 3 herein. Table 2 sets forth the amino acid sequence identifiers of the heavy chain variable regions (HCVRs), as well as heavy chain complementarity determining regions (HCDR1, HCDR2 and HCDR3). Table 3 sets forth the sequence identifiers of the nucleic acid molecules encoding the HCVRs, HCDR1, HCDR2 and HCDR3 regions of the exemplary anti-CD3 antibodies. Tables 4 and 5 set forth light chain variable regions (LCVRs), as well as complementarity determining regions (LCDR1, LCDR2 and LCDR3) of the exemplary anti-CD3 antibodies.

The present invention provides antibodies, or antigen-binding fragments thereof, comprising an HCVR comprising an amino acid sequence selected from any of the HCVR amino acid sequences listed in Table 2, or a substantially similar sequence thereof having having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 2 paired with any of the LCVR amino acid sequences listed in Table 4, or a common light chain derived from the cognate light chain of the anti-TAA heavy chain, or derived from a known or public domain light chain variable region derived from a light chain exhibiting promiscuity or ability to pair with a wide variety of non-cognate heavy chains, i.e. a universal or common light chain. According to certain embodiments, the present invention provides antibodies, or antigen-binding fragments thereof, comprising an HCVR/ LCVR amino acid sequence pair contained within any of the exemplary anti-CD3 antibodies listed in Table 2 paired with exemplary light chain variable regions listed in Table 4. In certain embodiments, the HCVR/LCVR amino acid sequence pair is selected from the group consisting of SEQ ID NOs: 10/162 (e.g., CD3-VH-G2); 18/162 (e.g., CD3-VH-G3); 26/162 (e.g., CD3-VH-G4); 34/162 (e.g., CD3-VH-G5); 42/162 (e.g., CD3-VH-G8); 50/162 (e.g., CD3-VH-G9); 58/162 (e.g., CD3-VH-G10); 66/162 (e.g., CD3-VH-G11); 74/162 (e.g., CD3-VH-G12); 82/162 (e.g., CD3-VH-G13); 90/162 (e.g., CD3-VH-G14); 98/162 (e.g., CD3-VH-G15); 106/162 (e.g., CD3-VH-G16); 114/162 (e.g., CD3-VH-G17); 122/162 (e.g., CD3-VH-G18); 130/162 (e.g., CD3-VH-G19); 138/162 (e.g., CD3-VH-G20); and 146/162 (e.g., CD3-VH-G21).

The present invention also provides antibodies, or antigen-binding fragments thereof, comprising a heavy chain CDR1 (HCDR1) comprising an amino acid sequence selected from any of the HCDR1 amino acid sequences listed in Table 2 or a substantially similar sequence thereof having at least 95%, at least 98% or at least 99% sequence identity. The present invention also provides antibodies, or antigen-binding fragments thereof, comprising a heavy chain CDR1 (HCDR1) comprising an amino acid sequence set forth in SEQ ID NO: 178.

The present invention also provides antibodies, or antigen-binding fragments thereof, comprising a heavy chain CDR2 (HCDR2) comprising an amino acid sequence selected from any of the HCDR2 amino acid sequences listed in Table 2 or a substantially similar sequence thereof having at least 95%, at least 98% or at least 99% sequence identity. The present invention also provides antibodies, or antigen-binding fragments thereof, comprising a heavy chain CDR2 (HCDR2) comprising an amino acid sequence set forth in SEQ ID NO: 179.

The present invention also provides antibodies, or antigen-binding fragments thereof, comprising a heavy chain CDR3 (HCDR3) comprising an amino acid sequence selected from any of the HCDR3 amino acid sequences listed in Table 2 or a substantially similar sequence thereof having at least 95%, at least 98% or at least 99% sequence identity. The present invention also provides antibodies, or antigen-binding fragments thereof, comprising a heavy chain CDR3 (HCDR3) comprising an amino acid sequence set forth in SEQ ID NO: 180.

The present invention also provides antibodies, or antigen-binding fragments thereof, comprising a light chain CDR1 (LCDR1) comprising an amino acid sequence selected from any of the LCDR1 amino acid sequences listed in Table 4 or a substantially similar sequence thereof having at least 95%, at least 98% or at least 99% sequence identity. The present invention also provides antibodies, or antigen-binding fragments thereof, comprising a light chain CDR1 (LCDR1) derived from a cognate light chain of the anti-TAA heavy chain, or derived from a light chain exhibiting promiscuity or ability to pair with a wide variety of non-cognate heavy chains, i.e. a universal or common light chain.

The present invention also provides antibodies, or antigen-binding fragments thereof, comprising a light chain CDR2 (LCDR2) comprising an amino acid sequence selected from any of the LCDR2 amino acid sequences listed in Table 4 or a substantially similar sequence thereof having at least 95%, at least 98% or at least 99% sequence identity. The present invention also provides antibodies, or antigen-binding fragments thereof, comprising a light chain CDR2 (LCDR2) derived from a cognate light chain of the anti-TAA heavy chain, or derived from a light chain exhibiting promiscuity or ability to pair with a wide variety of non-cognate heavy chains, i.e. a universal or common light chain.

The present invention also provides antibodies, or antigen-binding fragments thereof, comprising a light chain CDR3 (LCDR3) comprising an amino acid sequence selected from any of the LCDR3 amino acid sequences listed in Table 4 or a substantially similar sequence thereof having at least 95%, at least 98% or at least 99% sequence identity. The present invention also provides antibodies, or antigen-binding fragments thereof, comprising a light chain CDR3 (LCDR3) derived from a cognate light chain of the anti-TAA heavy chain, or derived from a light chain exhibiting promiscuity or ability to pair with a wide variety of non-cognate heavy chains, i.e. a universal or common light chain.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 2 paired with any of the LCDR3 amino acid sequences listed in Table 4. According to certain embodiments, the present invention provides antibodies, or antigen-binding fragments thereof, comprising an HCDR3/LCDR3 amino acid sequence pair contained within any of the exemplary anti-CD3 antibodies listed in Table 2. In certain embodiments, the HCDR3/LCDR3 amino acid sequence pair is selected from the group consisting of SEQ ID NOs: 16/168 (e.g., CD3-VH-G2); 24/168 (e.g., CD3-VH-G3); 32/168 (e.g., CD3-VH-G4); 40/168 (e.g., CD3-VH-G5); 48/168 (e.g., CD3-VH-G8); 56/168 (e.g., CD3-VH-G9); 64/168 (e.g., CD3-VH-G10); 72/168 (e.g., CD3-VH-G11); 80/168 (e.g., CD3-VH-G12); 88/168 (e.g., CD3-VH-G13); 96/168 (e.g., CD3-VH-G14); 104/168 (e.g., CD3-VH-G15); 112/168 (e.g., CD3-VH-G16); 120/168 (e.g., CD3-VH-G17); 128/168 (e.g., CD3-VH-G18); 136/168 (e.g., CD3-VH-G19); 144/168 (e.g., CD3-VH-G20); and 152/168 (e.g., CD3-VH-G21).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-CD3 antibodies listed in Tables 2 and 4. In certain embodiments, the HCDR1-HCDR2-HCDR3-LCDR1-LCDR2-LCDR3 amino acid sequences set is selected from the group consisting of SEQ ID NOs:Dec. 14, 2016-164-166-168 (e.g., CD3-VH-G2); 20-22-24-164-166-168 (e.g., CD3-VH-G3); 28-30-32-164-166-168 (e.g., CD3-VH-G4); 36-38-40-164-166-168 (e.g., CD3-VH-G5); 44-46-48-164-166-168 (e.g., CD3-VH-G8); 52-54-56-164-166-168 (e.g., CD3-VH-G9); 60-62-64-164-166-168 (e.g., CD3-VH-G10); 68-70-72-164-166-168 (e.g., CD3-VH-G11); 76-78-80-164-166-168 (e.g., CD3-VH-G12); 84-86-88-164-166-168 (e.g., CD3-VH-G13); 92-94-96-164-166-168 (e.g., CD3-VH-G14); 100-102-104-164-166-168 (e.g., CD3-VH-G15); 108-110-112-164-166-168 (e.g., CD3-VH-G16); 116-118-120-164-166-168 (e.g., CD3-VH-G17); 124-126-128-164-166-168 (e.g., CD3-VH-G18); 132-134-136-164-166-168 (e.g., CD3-VH-G19); 140-142-144-164-166-168 (e.g., CD3-VH-G20); and 148-150-152-164-166-168 (e.g., CD3-VH-G21).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD3 antibodies listed in Tables 2 and 4. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 10/162 (e.g., CD3-VH-G2); 18/162 (e.g., CD3-VH-G3); 26/162 (e.g., CD3-VH-G4); 34/162 (e.g., CD3-VH-G5); 42/162 (e.g., CD3-VH-G8); 50/162 (e.g., CD3-VH-G9); 58/162 (e.g., CD3-VH-G10); 66/162 (e.g., CD3-VH-G11); 74/162 (e.g., CD3-VH-G12); 82/162 (e.g., CD3-VH-G13); 90/162 (e.g., CD3-VH-G14); 98/162 (e.g., CD3-VH-G15); 106/162 (e.g., CD3-VH-G16); 114/162 (e.g., CD3-VH-G17); 122/162 (e.g., CD3-VH-G18); 130/162 (e.g., CD3-VH-G19); 138/162 (e.g., CD3-VH-G20); and 146/162 (e.g., CD3-VH-G21).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

The present invention also provides nucleic acid molecules encoding anti-CD3 antibodies or portions thereof. For example, the present invention provides nucleic acid molecules encoding any of the HCVR amino acid sequences listed in Table 3; in certain embodiments the nucleic acid molecule comprises a polynucleotide sequence selected from any of the HCVR nucleic acid sequences listed in Table 3, or a substantially similar sequence thereof having at least 90%, at least 95%, at least 98% or at least 99% sequence identity thereto.

The present invention also provides nucleic acid molecules encoding any of the LCVR amino acid sequences listed in Table 4; or an LCVR derived from a cognate light chain of the anti-TAA heavy chain, or derived from a light chain exhibiting promiscuity or ability to pair with a wide variety of non-cognate heavy chains, i.e. a universal or common light chain. In certain embodiments, the nucleic acid molecule comprises a polynucleotide sequence selected from any of the LCVR nucleic acid sequences listed in Table 5, or a substantially similar sequence thereof having at least 90%, at least 95%, at least 98% or at least 99% sequence identity thereto.

The present invention also provides nucleic acid molecules encoding any of the HCDR1 amino acid sequences listed in Table 2; in certain embodiments the nucleic acid molecule comprises a polynucleotide sequence selected from any of the HCDR1 nucleic acid sequences listed in Table 3, or a substantially similar sequence thereof having at least 90%, at least 95%, at least 98% or at least 99% sequence identity thereto.

The present invention also provides nucleic acid molecules encoding any of the HCDR2 amino acid sequences listed in Table 2; in certain embodiments the nucleic acid molecule comprises a polynucleotide sequence selected from any of the HCDR2 nucleic acid sequences listed in Table 3, or a substantially similar sequence thereof having at least 90%, at least 95%, at least 98% or at least 99% sequence identity thereto.

The present invention also provides nucleic acid molecules encoding any of the HCDR3 amino acid sequences listed in Table 2; in certain embodiments the nucleic acid molecule comprises a polynucleotide sequence selected from any of the HCDR3 nucleic acid sequences listed in Table 3, or a substantially similar sequence thereof having at least 90%, at least 95%, at least 98% or at least 99% sequence identity thereto.

The present invention also provides nucleic acid molecules encoding any of the LCDR1 amino acid sequences listed in Table 4; or an LCDR1 derived from a cognate light chain of the anti-TAA heavy chain, or derived from a light chain exhibiting promiscuity or ability to pair with a wide variety of non-cognate heavy chains, i.e. a universal or common light chain. In certain embodiments, the nucleic acid molecule comprises a polynucleotide sequence selected from any of the LCDR1 nucleic acid sequences listed in Table 5, or a substantially similar sequence thereof having at least 90%, at least 95%, at least 98% or at least 99% sequence identity thereto.

The present invention also provides nucleic acid molecules encoding any of the LCDR2 amino acid sequences listed in Table 4; or an LCDR2 derived from a cognate light chain of the anti-TAA heavy chain, or derived from a light chain exhibiting promiscuity or ability to pair with a wide variety of non-cognate heavy chains, i.e. a universal or common light chain. In certain embodiments, the nucleic acid molecule comprises a polynucleotide sequence selected from any of the LCDR2 nucleic acid sequences listed in Table 5, or a substantially similar sequence thereof having at least 90%, at least 95%, at least 98% or at least 99% sequence identity thereto.

The present invention also provides nucleic acid molecules encoding any of the LCDR3 amino acid sequences listed in Table 4; or an LCDR3 derived from a cognate light chain of the anti-TAA heavy chain, or derived from a light chain exhibiting promiscuity or ability to pair with a wide variety of non-cognate heavy chains, i.e. a universal or common light chain. In certain embodiments the nucleic acid molecule comprises a polynucleotide sequence selected from any of the LCDR3 nucleic acid sequences listed in Table 5, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD3 antibodies listed in Table 2.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary universal light chain antibodies listed in Table 4; or the LCDR1-LCDR2-LCDR3 is derived from a cognate light chain of the anti-TAA heavy chain, or derived from a light chain exhibiting promiscuity or ability to pair with a wide variety of non-cognate heavy chains, i.e. a universal or common light chain.

The present invention also provides nucleic acid molecules encoding both an HCVR and an LCVR, wherein the HCVR comprises an amino acid sequence of any of the HCVR amino acid sequences listed in Table 2, and wherein the LCVR comprises an amino acid sequence of any of the LCVR amino acid sequences listed in Table 4; or the LCVR is derived from a cognate light chain of the anti-TAA heavy chain, or derived from a light chain exhibiting promiscuity or ability to pair with a wide variety of non-cognate heavy chains, i.e. a universal or common light chain. In certain embodiments, the nucleic acid molecule comprises a poly-nucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 5, or a substantially similar sequence thereof having at least 90%, at least 95%, at least 98% or at least 99% sequence identity thereto. In some embodiments, the nucleic acid molecules encoding both an HCVR and an LCVR are fully human sequences or derived from human germline immunoglobulin sequences.

The present invention also provides recombinant expression vectors capable of expressing a polypeptide comprising a heavy or light chain variable region of an anti-CD3 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2 or 4. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-CD3 antibodies and/or anti-TAA antibodies, as well as bispecific anti-CD3/anti-TAA antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxic-ity (ADCC) function (see Shield et al. (2002) JBC 277: 26733). In other applications, modification of galactosy-lation can be made in order to modify complement dependent cytotoxicity (CDC).

In one aspect, the invention provides a cytotoxic compo-sition comprising a bispecific antigen-binding molecule that i) is not capable of specifically binding to an effector cell, and ii) specifically binds a target tumor cell, wherein specific binding is measured in an in vitro FACS binding assay or an in vitro surface plasmon resonance binding assay. In certain embodiments, the invention provides a cytotoxic composi-tion comprising a bispecific antigen-binding molecule that exhibits no detectable binding to an effector cell, and that specifically binds to a target tumor cell with a measurable binding affinity, wherein the binding affinity value is mea-sured in an in vitro FACS binding assay or an in vitro surface plasmon resonance binding assay.

In other embodiments, the invention provides a cytotoxic composition comprising a bispecific antigen-binding molecule comprising i) a first antigen-binding fragment (Fab1) that exhibits no detectable binding to CD3, and ii) a second antigen-binding fragment (Fab2) that specifically binds to a target tumor cell with a measurable binding affinity, wherein the binding affinity value is measured in an in vitro FACS binding assay or an in vitro surface plasmon resonance binding assay. In some cases, the binding affinity is mon-ovalent binding affinity (e.g., in a bispecific antibody con-struct).

In another aspect the invention provides a cytotoxic composition comprising a bispecific antigen-binding mol-ecule that specifically binds an effector cell with a weak binding affinity, for example exhibiting an $EC_{50}$ value of about or greater than about 100 nM, and that specifically binds a target tumor cell with an appreciable $EC_{50}$ value, or a high affinity $EC_{50}$ value such as less than 50 nM, wherein the $EC_{50}$ binding affinity value is measured in an in vitro FACS binding assay. In certain embodiments, the invention provides a cytotoxic composition comprising a bispecific antigen-binding molecule that specifically binds an effector cell with an $EC_{50}$ value of greater than about 500 nM, and that specifically binds a target tumor cell with an appreciable $EC_{50}$ value, or a high affinity $EC_{50}$ value such as less than 50 nM, wherein the $EC_{50}$ binding affinity value is measured in an in vitro FACS binding assay.

In some examples, the bispecific antigen-binding mol-ecule includes a Fab1 that specifically binds human CD3 with an $EC_{50}$ value of greater than about 40 nM, or greater than about 100 nM, greater than about 200 nM, greater than about 300 nM, greater than about 400 nM, greater than about 500 nM, or greater than about 1 μM (e.g. in a monovalent binding context). In some embodiments, the bispecific anti-gen-binding molecule includes a Fab2 derived from a sec-ond antibody that specifically binds the target tumor cell with high affinity, e.g. an $EC_{50}$ value of less than less than about 50 nM, less than about 40 nM, less than about 20 nM, less than about 10 nM or less than about 6 nM (e.g., in a monovalent binding context). In some cases, the Fab1 specifically binds each of human CD3 and cynomolgus CD3 with an $EC_{50}$ value of greater than about 40 nM, or greater than about 100 nM, greater than about 200 nM, or greater than about 1 μM. In some cases, the Fab1 specifically binds each of human CD3 and cynomolgus CD3 with weak or no measurable affinity.

In some embodiments, the target tumor cell is a human tumor cell. In some embodiments, the Fab1 (or the bispecific antigen-binding molecule) induces T cell-mediated tumor cell killing with an $EC_{50}$ value of less than about 1.3 nM, as measured in an in vitro T cell-mediated tumor cell killing assay.

In some applications, the Fab1 or the bispecific antigen-binding molecule specifically binds human CD3 with an $K_D$ value of greater than about 11 nM, as measured in an in vitro surface plasmon resonance binding assay. In other instances, the Fab1 or the bispecific antigen-binding molecule specifi-cally binds each of human CD3 and cynomolgus CD3 with an $K_D$ value of greater than about 15 nM, or greater than about 30 nM, greater than about 60 nM, greater than about 120 nM, or greater than about 300 nM, as measured in an in vitro surface plasmon resonance binding assay. In still some applications, the Fab1 or the bispecific antigen-binding molecule i) exhibits no detectable binding to human CD3 as measured in each of an in vitro surface plasmon resonance binding assay and a FACS binding assay, and ii) induces T cell-mediated tumor cell killing, as measured in an in vitro T cell-mediated tumor cell killing assay.

In some applications, the bispecific antigen-binding molecule comprises a first heavy chain comprising a HCDR1 region comprising an amino acid sequence set forth in SEQ ID NO: 12 or 20. In some embodiments, the first heavy chain comprises a HCDR2 region comprising an amino acid sequence set forth in SEQ ID NO: 14 or 54. In other embodiments, the first heavy chain comprises a HCDR3 region comprising an amino acid sequence set forth in SEQ ID NO: 16, SEQ ID NO: 24, SEQ ID NO: 32, SEQ ID NO: 40, SEQ ID NO: 48, SEQ ID NO: 56, SEQ ID NO: 64, SEQ ID NO: 72, SEQ ID NO: 80, SEQ ID NO: 88, SEQ ID NO: 96, SEQ ID NO: 104, SEQ ID NO: 112, SEQ ID NO: 120, SEQ ID NO: 128, SEQ ID NO: 136, SEQ ID NO: 144, or SEQ ID NO: 152. In other applications, the first heavy chain comprises a HCVR comprising HCDR1-HCDR2-HCDR3 having the amino acid sequences of SEQ ID NOs: 178-179-180. In other embodiments, a first heavy chain comprises a CDR1 comprising amino acid residues 1-7 of SEQ ID NO:178, a CDR2 comprising amino acid residues 1-7 of SEQ ID NO:179, a CDR3 comprising amino acid residues 4-11 of SEQ ID NO:180.

In more embodiments, the first heavy chain comprises variable domain framework regions having an amino acid sequence selected from FR1 (SEQ ID NO: 174), FR2 (SEQ ID NO: 175), FR3 (SEQ ID NO: 176), and FR4 (SEQ ID NO: 177).

The present invention provides bispecific antigen-binding molecules comprising a Fab1 HCVR and LCVR amino acid sequence pair (HCVR/LCVR) selected from the group consisting of: SEQ ID NOs: 10/162; 18/162; 26/162; 34/162; 42/162; 50/162; 58/162; 66/162; 74/162; 82/162; 90/162; 98/162; 106/162; 114/162; 122/162; 130/162; 138/162; 146/162.

The antibodies, and antigen-binding fragments and bispecific antibodies thereof were made by replacing amino acid residues of a parental in a stepwise manner based on differences between the germline sequence and the parental antibody sequence. The present invention provides a method of making a cytotoxic composition comprising (a) identifying the amino acid sequence of the first heavy chain derived from a first antibody that specifically binds CD3 with high affinity, for example exhibits a binding affinity $EC_{50}$ value of less than about 40 nM, (b) modifying selected amino acid residues in the heavy chain variable region of the first antibody to produce a modified antibody, (c) pairing the modified antibody with a second heavy chain derived from a second antibody that specifically binds a target tumor antigen to produce a bispecific antibody, (d) testing the bispecific antibody in a binding affinity assay, and if the binding affinity to CD3 has an $EC_{50}$ value of greater than about 40 nM, or greater than 100 nM or greater than 300 nM or greater than 500 nM, or no detectable binding, then (e) preparing a composition comprising the bispecific antibody and a pharmaceutically acceptable carrier or diluent. In addition to modifying the heavy chain variable region of selected antibodies to engineer antigen-binding arms having weak or no affinity for, yet specifically target an effector cell, the invention provides methods herein for modifying the heavy chain constant region (e.g. CH3 domain) of each binding arm to prepare and isolate bispecific antibodies.

An exemplary method provides a method of producing a cytotoxic bispecific antibody, comprising: (a) identifying a first human antibody or antigen-binding fragment thereof that interacts with an effector cell antigen from multiple species; (b) identifying the germline amino acid residues of the heavy chain variable region (HCVR) of the human antibody; (c) comparing the amino acid sequence of the HCVR of the first human antibody to the amino acid sequence of the corresponding germline HCVR; (d) identifying amino acids within a modified region of the HCVR of the first antibody, whereby a modified region in the first antibody displays at least one amino acid modification by substitution, deletion or addition of a single amino acid residue compared to the same region in the germline HCVR; (e) producing a plurality of modified antibodies each comprising at least one modified region of the HCVR; (f) screening each of the plurality of modified antibodies for monovalent affinity to the effector cell antigen; (g) selecting those modified antibodies that exhibit weaker binding affinity or no detectable binding affinity to the effector cell antigen compared to the first antibody; and (h) pairing the selected first antibody with a second antibody that interacts with a tumor-associated antigen to produce a cytotoxic bispecific antibody.

In another aspect, the invention provides a pharmaceutical composition comprising a recombinant human bispecific antibody or fragment thereof which specifically binds CD3 and a pharmaceutically acceptable carrier. In a related aspect, the invention features a composition which is a combination of an anti-CD3 antibody and a second therapeutic agent. In one embodiment, the second therapeutic agent is any agent that is advantageously combined with an anti-CD3 antibody. Exemplary agents that may be advantageously combined with an anti-CD3 antibody include, without limitation, other agents that bind and/or activate CD3 signaling (including other antibodies or antigen-binding fragments thereof, etc.) and/or agents which do not directly bind CD3 but nonetheless activate or stimulate immune cell activation. Additional combination therapies and co-formulations involving the anti-CD3 antibodies of the present invention are disclosed elsewhere herein.

In yet another aspect, the invention provides therapeutic methods for stimulating T cell activation using an anti-CD3 antibody or antigen-binding portion of an antibody of the invention, wherein the therapeutic methods comprise administering a therapeutically effective amount of a pharmaceutical composition comprising a bispecific antibody of the invention, or antigen-binding fragment thereof, to a subject in need thereof. The disorder treated is any disease or condition, which is improved, ameliorated, inhibited or prevented by cytotoxic therapy targeted to a tumor-associated antigen, such as cancer.

According to another aspect, the present invention provides bispecific antigen-binding molecules that bind CD3 and a target antigen, especially a tumor-associated antigen (TAA).

The present invention also includes the use of an anti-CD3/anti-TAA bispecific antigen-binding molecule of the invention in the manufacture of a medicament for the treatment of a disease or disorder related to or caused by TAA expression. The present invention also provides use of an anti-CD3/anti-TAA bispecific antigen-binding molecule, exhibiting weak affinity to CD3-expressing effector cells and reduced clearance, in the manufacture of a medicament for the treatment of a disease or disorder related to or caused by TAA expression, compared to an anti-CD3/anti-TAA bispecific antigen-binding molecule exhibiting high affinity to CD3-expressing effector cells.

Other embodiments will become apparent from a review of the ensuing detailed description.

germline hIgHV (SEQ ID NO:181); CD3-VH-P (SEQ ID NO: 154); CD3-VH-G (SEQ ID NO:2); CD3-VH-G2 (SEQ ID NO:10); CD3-VH-G3 (SEQ ID NO: 18); CD3-VH-G4 (SEQ ID NO:26); CD3-VH-G5 (SEQ ID NO: 34); CD3-VH-G8 (SEQ ID NO: 42); CD3-VH-G9 (SEQ ID NO:50); CD3-VH-G10 (SEQ ID NO:58); CD3-VH-G11 (SEQ ID NO: 66); CD3-VH-G12 (SEQ ID NO:74); CD3-VH-G13 (SEQ ID NO:82); CD3-VH-G14 (SEQ ID NO:90); CD3-VH-G15 (SEQ ID NO:98); CD3-VH-G16 (SEQ ID NO:106); CD3-VH-G17 (SEQ ID NO:114); CD3-VH-G18 (SEQ ID NO:122); CD3-VH-G19 (SEQ ID NO: 130); CD3-VH-G20 (SEQ ID NO:138); and CD3-VH-G21 (SEQ ID NO:146). Each derivative HCVR is compared to the parent antibody and germline amino acid residues, with rectangular boxes denoting mutations in the CDRs.

Figure 2A:
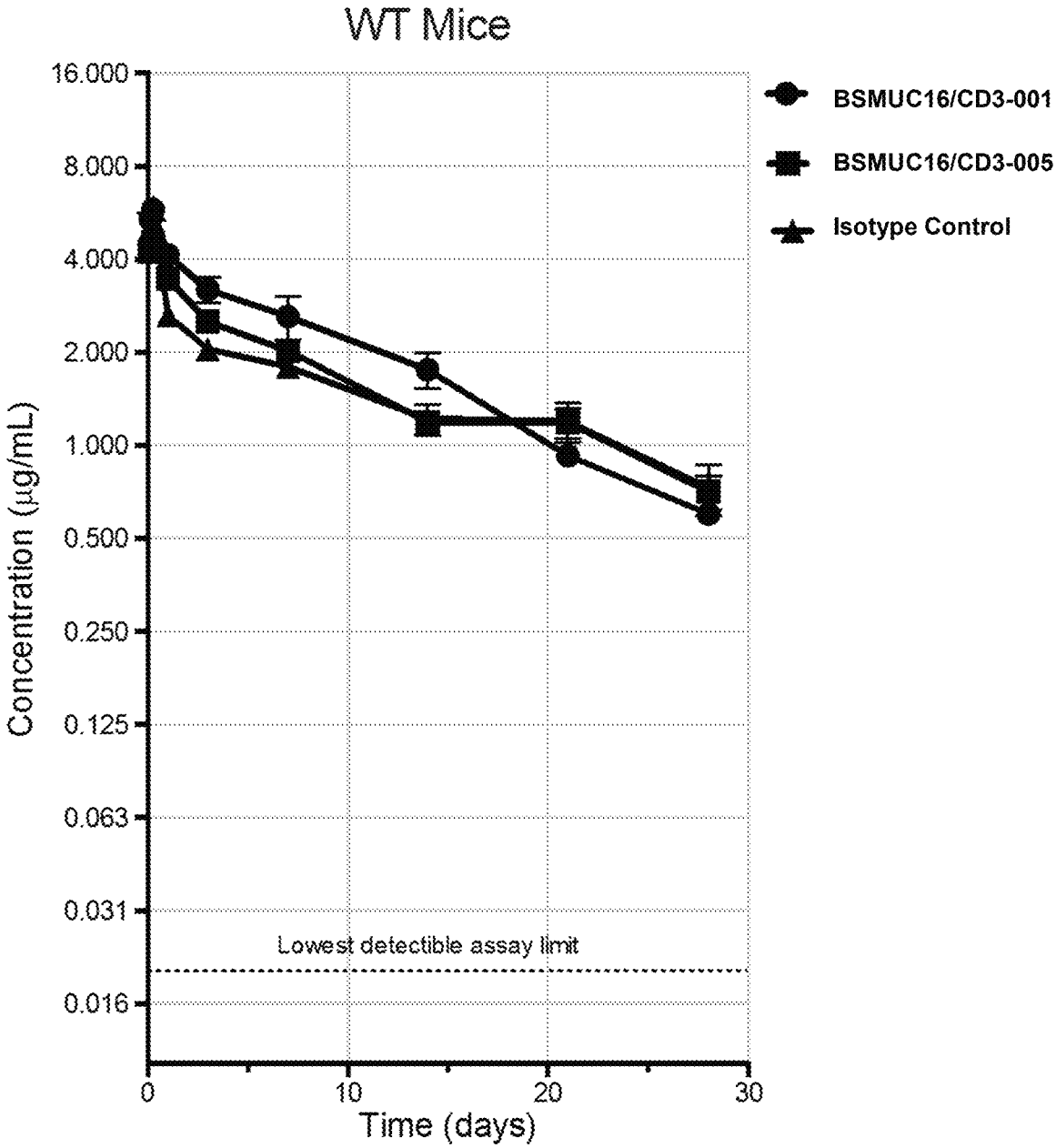
Figure 2B:
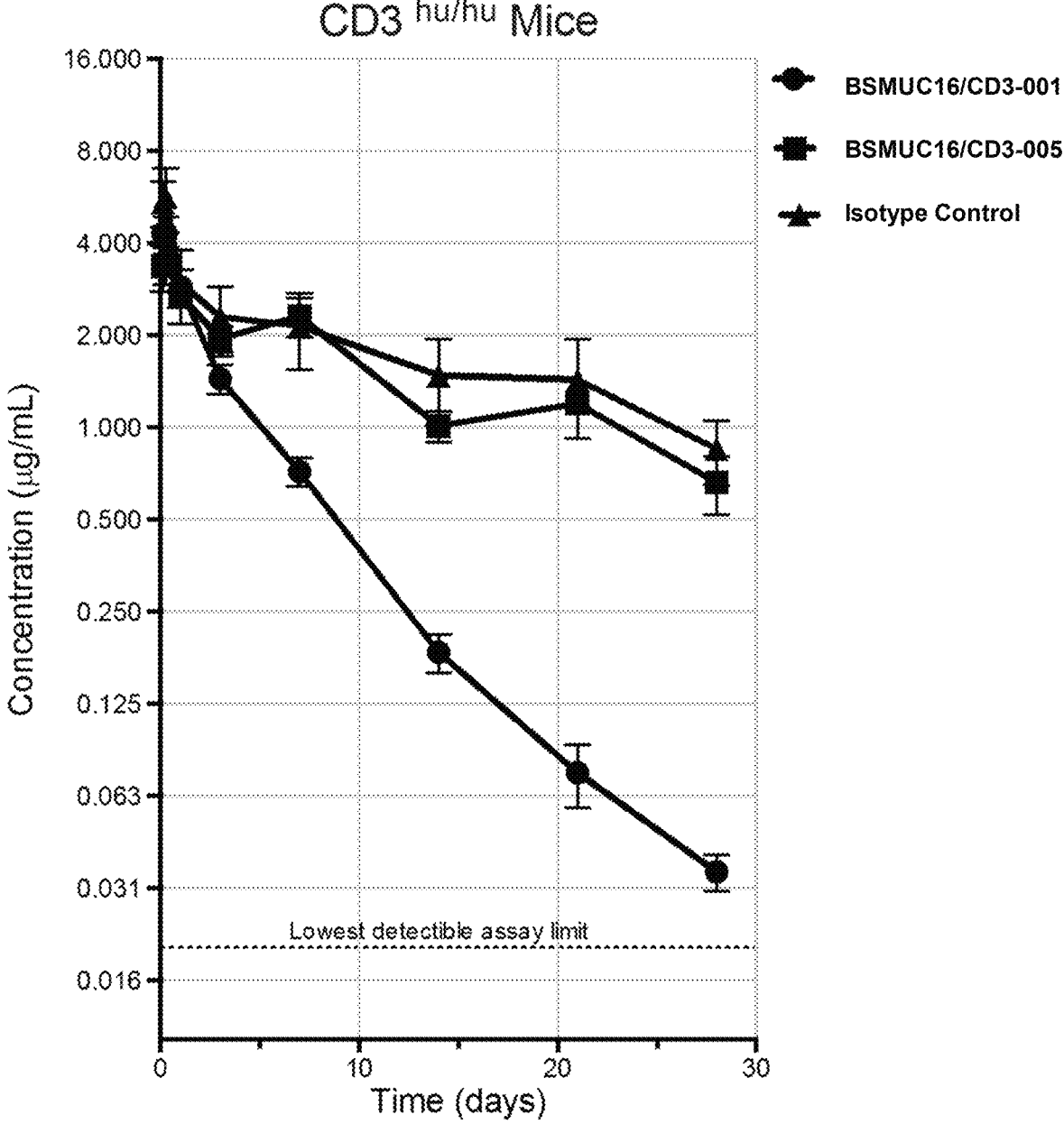
Figure 2C:
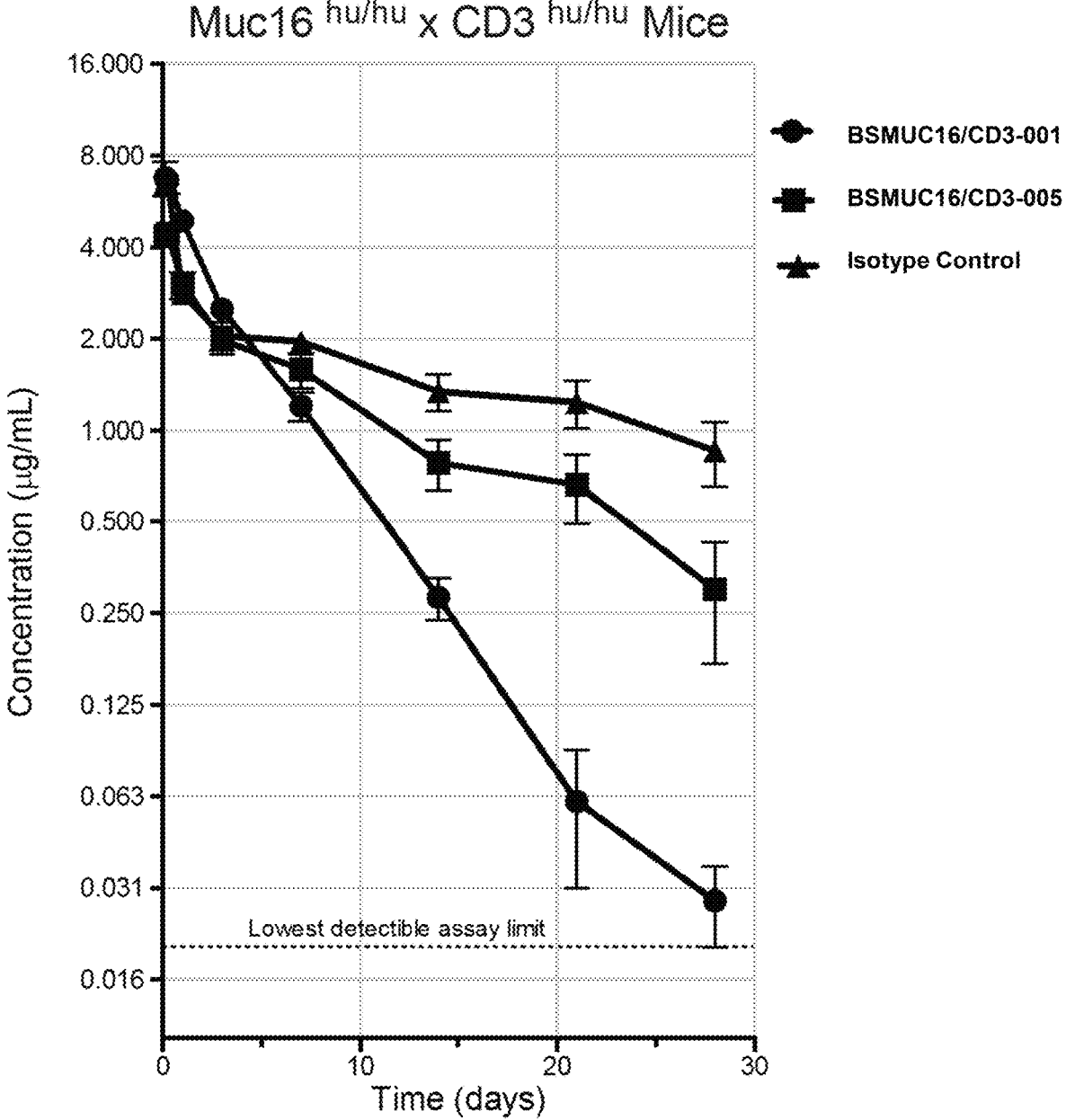

FIGS. 2A, 2B and 2C illustrate mean concentrations of total IgG in serum following a single 0.4 mg/kg intra-peritoneal injection of BSMUC16/CD3-001, BSMUC16/CD3-005 and isotype control antibodies in wild-type mice (FIG. 2A), humanized CD3 mice (FIG. 2B) and humanized MUC16×CD3 mice (FIG. 2C).

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Definitions

The expression "CD3" refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. Human CD3-epsilon (hCD3E) comprises the amino acid sequence as set forth in SEQ ID NO:169 (UniProtKB/Swiss-Prot: P07766.2). Human CD3-delta (hCD38) comprises the amino acid sequence as set forth in SEQ ID NO:170 (UniProtKB/Swiss-Prot: P04234.1). All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

The phrase "an antibody that binds CD3" or an "anti-CD3 antibody" includes antibodies and antigen-binding fragments thereof that specifically recognize and associate with a single CD3 subunit (e.g., epsilon, delta, gamma or zeta), as well as antibodies and antigen-binding fragments thereof that specifically recognize and associate with a dimeric complex of two CD3 subunits (e.g., epsilon/delta, epsilon/gamma, and zeta/zeta CD3 dimers). The antibodies and antigen-binding fragments of the present invention may bind soluble CD3, bound CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane. The present invention provides antibodies that bind and activate human and cynomolgus CD3 with weak or no detectable binding affinity. "Binding to CD3 with no detect-able binding affinity" means that the antibody and or anti-gen-binding fragment interaction with the CD3 target may not be measurable or detectable with a known assay for detection, such as a FACS (cell-based) binding assay as described herein or a surface plasmon resonance binding assay as described herein and well-known in the art. Other binding assays are well-known in the art. The antibody and or antigen-binding fragment may recognize the CD3 target by very weak protein-protein biochemical interaction, how-ever a determination of specific $K_D$ or $EC_{50}$ value cannot be measured since the interaction is beyond the detection limit of the assay, e.g. no measurement can be determined. In another instance, "no detectable binding affinity" is deter-mined if the affinity of an antibody corresponding to a $K_D$ value is equal to or less than ten-fold lower than a non-specific antigen such as, BSA, casein, or the like. "Binding to CD3 with weak binding affinity" includes interactions where binding affinity measurement is at or slightly above the detection limit of the assay, or equivalent to the binding affinity to a non-specific antigen.

The expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., delta/epsilon, gamma/epsilon, and zeta/zeta CD3 dimers). The expression, "cell surface-expressed CD3" also includes a CD3 chain (e.g., CD3-delta, CD3-epsilon or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

Efffector cells include effector T cells (T lymphocytes), for example CD4+T cells, CD8+T cells, Th1, Th2 and regulatory T cells (Tregs). Effector cells may also include natural killer (NK) cells, macrophages, granulocytes, plasma cells or B cells (lymphocytes). It is understood that therapies may mediate a plethora of cell-mediated immune responses, or effector functions, through Ig interaction with effector cell surface receptors, such as CD3 (T cell surface receptor), CD28 (T cells), Fcγ receptors (FcγRs) (NK cells, activated macrophages and the like). Effector functions such as cell killing, complement activation, phagocytosis and opsonisa-tion are subsequently triggered through these interactions. Binding to an effector cell and a tumor target cell allows for a valuable and effective immunotherapy design that propa-gates tumor cell killing and induces endogenous immune functions to fight the tumor or cancer.

The expression "anti-CD3 antibody" includes both mon-ovalent antibodies with a single specificity, as well as bispecific antibodies comprising a first arm that binds CD3 and a second arm that binds a second (target) antigen, wherein the anti-CD3 arm comprises any of the HCVR/LCVR or CDR sequences as set forth in Tables 2, 3, 4 and/or 5 herein. Examples of anti-CD3 bispecific antibodies are described elsewhere herein. The term "antigen-binding mol-ecule" includes antibodies and antigen-binding fragments of antibodies, including, e.g., bispecific antibodies.

The term "antibody" includes any antigen-binding mol-ecule or molecular complex comprising at least one comple-mentarity determining region (CDR) that specifically binds to or interacts with a particular antigen (e.g., CD3). The term "antibody" includes immunoglobulin molecules comprising four polypeptide chains, two heavy (H) chains and two light (L) chains inter-connected by disulfide bonds, as well as multimers thereof (e.g., lgM). Each heavy chain comprises a heavy chain variable region (abbreviated herein as HCVR or VA) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed comple-mentarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD3 antibody (or antigen-binding portion thereof) may be identical to the human germline sequences, or may be naturally or artificially modified. An amino acid consen-sus sequence may be defined based on a side-by-side analy-sis of two or more CDRs.

The term "antibody" also includes antigen-binding frag-ments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that spe-cifically binds an antigen to form a complex. Antigen-binding fragments of an antibody may be derived, e.g., from full antibody molecules using any suitable standard tech-niques such as proteolytic digestion or recombinant genetic engineering techniques involving the manipulation and expression of DNA encoding antibody variable and option-ally constant domains. Such DNA is known and/or is readily available from, e.g., commercial sources, DNA libraries (including, e.g., phage-antibody libraries), or can be synthe-sized. The DNA may be sequenced and manipulated chemi-cally or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F (ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chi-meric antibodies, CDR-grafted antibodies, diabodies, tria-bodies, tetrabodies, minibodies, nanobodies (e.g. monova-lent nanobodies, bivalent nanobodies, etc.), small modular immunopharmaceuticals (SMIPs), and shark variable IgNAR domains, are also encompassed within the expres-sion "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH—VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding frag-ment of an antibody of the present invention include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding frag-ments may be monospecific or multispecific (e.g., bispe-cific). A multispecific antigen-binding fragment of an anti-body will typically comprise at least two different variable domains, wherein each variable domain is capable of spe-cifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or anti-body-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD3 antibodies of the invention (monospecific or bispecific) are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, do not necessarily naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al.

(1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD3. The phrase "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 2 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Germline Mutations

The anti-CD3 antibodies disclosed herein comprise one or more amino acid substitutions, insertions and/or deletions in the framework and/or CDR regions of the heavy chain variable domains as compared to the corresponding germline sequences from which the antibodies were derived.

The present invention also includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable binding to a CD3 antigen. Several such exemplary antibodies that recognize CD3 are described in Table 2 herein.

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

The present invention also includes anti-CD3 antibodies comprising variants of any of the HCVR, LCVR, and/or CDR amino acid sequences disclosed herein having one or more conservative substitutions. For example, the present invention includes anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 2 herein. The antibodies and bispecific antigen-binding molecules of the present invention comprise one or more amino acid substitutions, insertions and/or deletions in the framework and/or CDR regions of the heavy and light chain variable domains as compared to the corresponding germline sequences from which the individual antigen-binding domains were derived, while maintaining or improving the desired weak-to-no detectable binding to CD3 antigen. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein, i.e. the amino acid substitution maintains or improves the desired weak to no detectable binding affinity in the case of anti-CD3 binding molecules. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445. A "moderately conservative" replacement is any change having a nonnegative value in the PAM250 log-likelihood matrix.

The present invention also includes antigen-binding molecules comprising an antigen-binding domain with an HCVR and/or CDR amino acid sequence that is substantially identical to any of the HCVR and/or CDR amino acid sequences disclosed herein, while maintaining or improving the desired weak affinity to CD3 antigen. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Once obtained, antigen-binding domains that contain one or more germline mutations were tested for decreased binding affinity utilizing one or more in vitro assays. Although antibodies that recognize a particular antigen are typically screened for their purpose by testing for high (i.e. strong) binding affinity to the antigen, the antibodies of the present invention exhibit weak binding or no detectable binding. Bispecific antigen-binding molecules comprising one or more antigen-binding domains obtained in this general manner are also encompassed within the present invention and were found to be advantageous as avidity-driven tumor therapies.

Unexpected benefits, for example, improved pharmacokinetic properties and low toxicity to the patient may be realized from the methods described herein.

Binding Properties of the Antibodies

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$M or less, such as about $10^{-8}$M or less, such as about $10^{-9}$M or less when determined by, for instance, surface plasmon resonance (SPR) technology in a BIACORE™3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, CA, J Immunol Methods. 1997, 201 (2): 223-31; Geuijen, CA, et al. J Immunol Methods. 2005, 302 (1-2): 68-77).

Accordingly, the antibody or antigen-binding protein of the invention may bind to the predetermined antigen or cell surface molecule (receptor such as CD3) having an affinity corresponding to a $K_D$ value that is at least ten-fold lower than its affinity for binding to a non-specific antigen (e.g., BSA, casein). According to the present invention, if the affinity of an antibody corresponding to a $K_D$ value is equal to or less than ten-fold lower than a non-specific antigen, this may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be. For example, "low affinity" refers to less strong binding interaction. In some embodiments, the low binding affinity corresponds to greater than about 1 nM Kp, greater than about 2, 3, 4, 5, 6, 7, 8, 9, 10, 11, 12, 13, 14, 15, 16, 17, 18, 19, 20, 25, 30, 35, or greater than about 40 nM Kp, wherein such $K_D$ binding affinity value is measured in an in vitro surface plasmon resonance binding assay, or equivalent biomolecular interaction sensing assay. In some embodiments, the low binding affinity corresponds to greater than about 10 nM $EC_{50}$, greater than about 15 nM $EC_{50}$, 20 nM $EC_{50}$, greater than about 25 nM $EC_{50}$, 30 nM $EC_{50}$, greater than about 35 nM $EC_{50}$, or greater than about 40 nM $EC_{50}$, wherein such $EC_{50}$ binding affinity value is measured in an in vitro FACS binding assay, or equivalent cell-based binding assay. "Weak affinity" refers to weak binding interaction. In some embodiments, the weak binding affinity corresponds to greater than about 100 nM $K_D$ or $EC_{50}$, greater than about 200, 300, or greater than about 500 nM $K_D$ or $EC_{50}$, wherein such $K_D$ binding affinity value is measured in an in vitro surface plasmon resonance binding assay, or equivalent biomolecular interaction sensing assay, and such $EC_{50}$ binding affinity value is measured in an in vitro FACS binding assay, or equivalent cell-based interaction detecting assay to detect monovalent biding. No detectable binding means that the affinity between the two biomolecules, for example, especially between the monovalent antibody binding arm and its target antigen, is beyond the detection limit of the assay being used.

The term "$k_d$" (sec-1 or 1/s) refers to the dissociation rate constant of a particular antibody-antigen interaction, or the dissociation rate constant of an antibody or antibody-binding fragment. Said value is also referred to as the Koff value.

The term "$k_d$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing CD3 or tumor-associated antigen, as determined by e.g. a FACS binding assay. Thus, reduced or weaker binding is observed with an increased $EC_{50}$ value, or half maximal effective concentration value such that 500 nM $EC_{50}$ is indicative of a weaker binding affinity than 50 nM $EC_{50}$.

In one embodiment, decreased binding can be defined as an increased $EC_{50}$ antibody concentration which enables binding to the half-maximal amount of target cells.

In other experimental measurements, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Bispecific Antigen-Binding Molecules

The antibodies of the present invention may be bi-specific, or multispecific. Multispecific antibodies may be specific for one effector molecule, such as CD3, in combination with different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expression "anti-CD3 antibody" herein is intended to include both monospecific anti-CD3 antibodies as well as bispecific antibodies comprising a CD3-binding arm and a second arm that binds a target antigen. Thus, the present invention includes bispecific antibodies wherein one arm of an immunoglobulin binds human CD3, and the other arm of the immunoglobulin is specific for a target antigen. The target antigen that the other arm of the CD3 bispecific antibody binds can be any antigen expressed on or in the vicinity of a cell, tissue, organ, microorganism or virus, against which a targeted immune response is desired. The CD3-binding arm can comprise any of the HCVR or CDR amino acid sequences as set forth in Table 2 herein. In certain embodiments, the CD3-binding arm binds weakly to human CD3 and induces human T cell activation. In other embodiments, the CD3-binding arm binds weakly to human CD3 and induces tumor-associated antigen-expressing cell killing in the context of a bispecific or multispecific antibody. In other embodiments, the CD3-binding arm binds or associated weakly with human and cynomolgus (monkey) CD3, yet the binding interaction is not detectable by in vitro assays known in the art. In some embodiments of the invention, the CD3-binding arm does not bind or associate with human and cynomolgus (monkey) CD3, yet the bispecific molecule still elicits tumor-associated cell killing.

In the context of bispecific antibodies of the present invention wherein one arm of the antibody binds CD3 and the other arm binds a target antigen, the target antigen can be a tumor-associated antigen (TAA). Non-limiting examples of specific tumor-associated antigens include, e.g., AFP, ALK, BAGE proteins, BIRC5 (survivin), BIRC7, β-catenin, brc-abl, BRCA1, BORIS, CA9, carbonic anhydrase IX, caspase-8, CALR, CCR5, CD19, CD20 (MS4A1), CD22, CD30, CD40, CDK4, CEA, CTLA4, cyclin-B1, CYP1B1, EGFR, EGFRvlll, ErbB2/Her2, ErbB3, ErbB4, ETV6-AML, EpCAM, EphA2, Fra-1, FOLR1, GAGE proteins (e.g., GAGE-1,-2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1,-2,-3,-4,-6, and-12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, STEAP1, STEAP2, TAG-72, TGF-β, TMPRSS2, Thompson-nouvelle antigen (Tn), TRP-1, TRP-2, tyrosinase, and uroplakin-3.

The inventors envision that the present invention includes numerous examples of bispecific antibodies having a weak anti-CD3 binding arm made in accordance with the invention.

According to certain exemplary embodiments, the present invention includes bispecific antigen-binding molecules that specifically bind CD3 and PSMA. Such molecules may be referred to herein as, e.g., "anti-CD3/anti-PSMA," or "anti-CD3×PSMA" or "CD3×PSMA" bispecific molecules, and so forth. The term "PSMA," as used herein, refers to the human PSMA protein unless specified as being from a non-human species (e.g., "mouse PSMA," "monkey PSMA," etc.).

The term "PSMA" refers to prostate-specific membrane antigen, also known as folate hydrolase 1 (FOLH1) (Uni-ProtKB/Swiss-Prot. No. Q04609; SEQ ID NO: 171). PSMA is an integral, non-shed membrane glycoprotein that is highly expressed in prostate epithelial cells and is a cell-surface marker for prostate cancer.

According to other exemplary embodiments, the present invention includes bispecific antigen-binding molecules that specifically bind CD3 and EGFRvlll. Such molecules may be referred to herein as, e.g., "anti-CD3/anti-EGFRvlll" or "anti-CD3×EGFRvlll" or "CD3×EGFRvlll" bispecific molecules, and so forth. The term "EGFRvlll" refers to the human EGFRvlll protein unless specified as being from a non-human species (e.g., "mouse EGFRvlll," "monkey EGFRvlll," etc.).

The term "EGFRvlll" refers to the class lll variant of the epidermal growth factor receptor (EGFRvlll; SEQ ID NO: 172) which is the most frequently found EGFR variant in glioblastoma (Bigner et al., 1990, Cancer Res 50:8017-8022; Humphrey et al., 1990, Proc Natl Acad Sci USA 87:4207-4211; Yamazaki et al., 1990, Jap J Cancer Res 81:773-779; Ekstrand et al., 1992, Proc Natl Acad Sci USA 89:4309-4313; Wikstrand et al., 1995, Cancer Res 55:3140-3148; and Frederick et al., 2000, Cancer Res 60:1383-1387). EGFRvlll is characterized by a deletion of exons 2-7 of the EGFR gene, resulting in an in-frame deletion of 801 base pairs of the coding region, i.e., deletion of 6-273 amino acid residues (based on the residue numbers of mature EGFR; see UniProtKB/Swiss-Prot. No. P00533), as well as the generation of a new glycine at the fusion junction (Humphrey et al., 1988, Cancer Res 48:2231-2238; Yamazaki et al., 1990, supra). EGFRvlll has been shown to have a ligand-independent, weak but constitutively active kinase activity as well as enhanced tumorigenicity (Nishikawa et al., 1994, Proc Natl Acad Sci USA 91:7727-7731; and Batra et al., 1995, Cell Growth and Differentiation 6:1251-1259). In addition to gliomas, EGFRvlll has been detected in ductal and intraductal breast carcinoma (Wikstrand et al., 1995, Cancer Res 55:3140-3148), non-small cell lung carcinomas (Garcia de Palazzo et al., 1993, Cancer Res 53:3217-3220), ovarian carcinomas (Moscatello et al., 1995, Cancer Res 55:5536-5539), prostate cancer (Olapade-Olaopa et al., 2000, British J Cancer 82:186-194), and squamous cell carcinoma of the head and neck (Tinhofer et al., 2011, Clin Cancer Res 17 (15): 5197-5204).

In still other exemplary embodiments, the present invention includes bispecific antigen-binding molecules that specifically bind CD3 and MUC16. Such molecules may be referred to herein as, e.g., "anti-CD3/anti-MUC16" or "anti-CD3×MUC16" or "CD3×MUC16" bispecific molecules, and so forth. The term "MUC16" refers to the human MUC16 protein unless specified as being from a non-human species (e.g., "mouse MUC16," "monkey MUC16," etc.).

Mucin 16 (MUC16; NCBI Reference Sequence: NP_078966.2, SEQ ID NO: 173), otherwise known as cancer antigen 125 (CA-125), is a mucin encoded by MUC16 gene in humans. The family of mucin proteins are known to protect the body from infection by pathogen binding to oligosaccharides in the extracellular domain, preventing the pathogen form reaching the cell surface. For many years, overexpression of MUC16/CA125 has been used as a prognostic and diagnostic marker for ovarian cancer (Yin and Lloyd, 2001, J. Biol. Chem. 276 (29), 27371-27375; O'Brien, T J, et al, 2001, Tumour Biol. 22 (6), 348-366; Leggieri, C. et al., 2014, Eur. J. Gynaecol. Oncol. 35 (4), 438-441). MUC16 has been shown to protect tumor cells from the immune system with its heavily glycosylated tandem repeat domain which can bind to galectin-1 (an immunosuppressive protein) (Seelenmeyer, C., et al., 2003, J. Cell. Sci. 116 (Pt 7): 1305-18; O'Brien, T J, et al., 2002, Tumour Biol. 23 (3), 154-169). Natural killer cells and monocytes are unable to attack tumor cells expressing high levels of MUC16. In its normal physiologic role, MUC16-galactin interaction serves as a barrier for bacterial and viral infection, however MUC16 is believed to be immunoprotective in the context of tumor cells, thereby preventing cancer cell cytolysis (Felder, M. et al., 2014, Molecular Cancer, 13:129). MUC16 is therefore a desirable target for immunotherapeutic bispecific antibody molecules administered to treat ovarian cancer by activating immune effector cells.

In still other exemplary embodiments, the present invention includes bispecific antigen-binding molecules that specifically bind CD3 and STEAP2. Such molecules may be referred to herein as, e.g., "anti-CD3/anti-STEAP2" or "anti-CD3×STEAP2" or "CD3×STEAP2" bispecific molecules, and so forth. The term "STEAP2" refers to the human STEAP2 protein unless specified as being from a non-human species (e.g., "mouse STEAP2," "monkey STEAP2," etc.). Six transmembrane epithelial antigen of the prostate 2 (STEAP2; UniProtKB/Swiss-Prot: Q8NFT2.3) is a 490-amino acid protein encoded by STEAP2 gene located at the chromosomal region 7q21 in humans.

The aforementioned bispecific antigen-binding molecules that specifically bind tumor-associated antigen comprise an anti-CD3 antigen-binding molecule which binds to CD3 with a weak or no detectable binding affinity such as exhibiting a $K_D$ of greater than about 100 nM, 300 nM or 500 nM, as measured by an in vitro affinity binding assay.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD3), and the second antigen-binding domain specifically binds a second, distinct antigen (e.g., PSMA, MUC16, EGFRvlll or STEAP2).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin CH3 domain. A non-limiting example of a multimerizing component is an Fc portion of an immunoglobulin (comprising a CH2-CH3 domain), e.g., an Fc domain of an IgG selected from the isotypes lgG1, lgG2, lgG3, and lgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab2 bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a CH2 or a CH3 region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V821 (by IMGT; D356E, L358M, N384S, K392N, V397M, and V4221 by EU) in the case of IgG1 antibodies; N44S, K52N, and V821 (IMGT; N384S, K392N, and V4221 by EU) in the case of IgG2 antibodies; and Q15R, N44S, K52N, V57M, R69K, E79Q, and V821 (by IMGT; Q355R, N384S, K392N, V397M, R409K, E419Q, and V4221 by EU) in the case of IgG4 antibodies.

In certain embodiments, the Fc domain may be chimeric, combining Fc sequences derived from more than one immunoglobulin isotype. For example, a chimeric Fc domain can comprise part or all of a CH2 sequence derived from a human IgG1, human IgG2 or human IgG4 CH2 region, and part or all of a CH3 sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 CH1]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 CH1]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in PCT International Publication No. WO2014/121087 A1, published Aug. 7, 2014, which is herein incorporated by reference in its entirety. Chimeric Fc domains having these general structural arrangements, and variants thereof, can have altered Fc receptor binding, which in turn affects Fc effector function.

In certain embodiments, the invention provides an antibody heavy chain wherein the heavy chain constant region (CH) region comprises an amino acid sequence at least 95%, at least 96%, at least 97%, at least 98%, at least 99% identical to any one of SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190 or SEQ ID NO: 191. In some embodiments, the heavy chain constant region (CH) region comprises an amino acid sequence selected form the group consisting of SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190 and SEQ ID NO: 191.

In other embodiments, the invention provides an antibody heavy chain wherein the Fc domain comprises an amino acid sequence at least 95%, at least 96%, at least 97%, at least 98%, at least 99% identical to any one of SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200 or SEQ ID NO: 201. In some embodiments, the Fc domain comprises an amino acid sequence selected form the group consisting of SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200 and SEQ ID NO: 201.

Other Fc Variants

According to certain embodiments of the present invention, anti-CD3 antibodies, and anti-CD3/anti-TAA bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD3 antibodies, and anti-CD3/anti-TAA bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes bispecific antigen-binding molecules (e.g., bispecific antibodies) which are capable of simultaneously binding to human CD3 and a human TAA. According to certain embodiments, the bispecific antigen-binding molecules of the invention specifically interact with cells that express CD3 and/or TAA, such as PSMA, EGFRvlll or MUC16. The binding arm that interacts with cells that express CD3 may have weak to no detectable binding as measured in a suitable in vitro binding assay. The extent to which a bispecific antigen-binding molecule binds cells that express CD3 and/or TAA can be assessed by fluorescence activated cell sorting (FACS), as illustrated in Example 4 herein.

For example, the present invention includes antibodies, antigen-binding fragments, and bispecific antibodies thereof which specifically bind human T-cell lines which express CD3 but not the TAA (e.g., Jurkat), primate T-cells (e.g., cynomolgus peripheral blood mononuclear cells [PBMCs]), and/or TAA-expressing cells. The present invention includes bispecific antigen-binding molecules which bind any of the aforementioned T cells and T cell lines with an $EC_{50}$ value of from about $1.8 \times 10^{-8}$ (18 nM) to about $2.1 \times 10^{-7}$ (210 nM), or more (i.e. weaker affinity), and includes bispecific antibodies for which $EC_{50}$ is undetectable, as determined using a FACS binding assay as set forth in Example 4 or a substantially similar assay. In certain embodiments, the antibodies, antigen-binding fragments, and bispecific antibodies of the present invention bind CD3 with an $EC_{50}$ of greater than about 30 nM, greater than about 40 nM, greater than about 45 nM, greater than about 50 nM, greater than about 55 nM, greater than about 60 nM, greater than about 65 nM, greater than about 70 nM, greater than about 75 nM, at least 80 nM, greater than about 90 nM, greater than about 100 nM, greater than about 110 nM, at least 120 nM, greater than about 130 nM, greater than about 140 nM, greater than about 150 nM, at least 160 nM, greater than about 170 nM, greater than about 180 nM, greater than about 190 nM, greater than about 200 nM, greater than about 250 nM, greater than about 300 nM, greater than about 500 nM, greater than about 1 μM, greater than about 2 μM, or greater than about 3 μM, or no detectable binding affinity, as measured by FACS binding, e.g., using an assay format as defined in Example 4 herein, or a substantially similar assay.

The present invention also includes antibodies, antigen-binding fragments, and bispecific antibodies thereof which bind to TAA-expressing cells and cell lines, such as PSMA-, EGFRvlll-, STEAP2- and MUC16-expressing cell lines, with an $EC_{50}$ value of less than about 100 nM, or even less concentration necessary for binding (i.e. stronger affinity) such as less than 5.6 nM ($5.6 \times 10^{-9}$), as determined using a FACS binding assay as set forth in Example 4 or a substantially similar cell-based assay. The present invention includes bispecific antigen-binding molecules which bind any of the aforementioned tumor cell lines with an $EC_{50}$ value of less than about 50 nM, less than about 45 nM, less than less 40 nM, less than about 35 nM, less than about 30 nM, less than about 25 nM, less than about 20 nM, less than about 15 nM, less than about 10 nM, less than about 6 nM, less than about 5 nM, or less than about 1 nM, e.g. using the aforementioned assay.

The present invention includes antibodies, antigen-binding fragments, and bispecific antibodies thereof that bind human CD3 with low, weak or even no detectable affinity. According to certain embodiments, the present invention includes antibodies and antigen-binding fragments of antibodies that bind human CD3 (e.g., at 37° C.) with a $K_D$ of greater than about 11 nM, includes antibodies that bind CD3 with a $K_D$ of greater than about 100 nM or 500 nM, and also includes antibodies having no detectable binding affinity, as measured by surface plasmon resonance, e.g., using an assay format as defined in Example 5 herein. In certain embodiments, the antibodies or antigen-binding fragments of the present invention bind CD3 with a $K_D$ of greater than about 15 nM, greater than about 20 nM, greater than about 25 nM, greater than about 30 nM, greater than about 35 nM, greater than about 40 nM, greater than about 45 nM, greater than about 50 nM, greater than about 55 nM, greater than about 60 nM, greater than about 65 nM, greater than about 70 nM, greater than about 75 nM, at least 80 nM, greater than about 90 nM, greater than about 100 nM, greater than about 110 nM, at least 120 nM, greater than about 130 nM, greater than about 140 nM, greater than about 150 nM, at least 160 nM, greater than about 170 nM, greater than about 180 nM, greater than about 190 nM, greater than about 200 nM, greater than about 250 nM, greater than about 300 nM, greater than about 1 μM, greater than about 2 μM, or greater than about 3 $\mu$M, or no detectable affinity, as measured by surface plasmon resonance, e.g., using an assay format as defined in Example 5 herein (e.g., mAb-capture or antigen-capture format), or a substantially similar assay.

The present invention includes antibodies, antigen-binding fragments, and bispecific antibodies thereof that bind monkey (i.e. cynomolgus) CD3 with low, weak, or even no detectable affinity. According to certain embodiments, the present invention includes antibodies, antigen-binding fragments, and bispecific antibodies thereof that bind human CD3 (e.g., at 37° C.) with a $K_D$ of greater than about 10 nM, includes antibodies that bind CD3 with a $K_D$ of greater than about 100 nM or 500 nM, and also includes antibodies having no detectable binding affinity, as measured by surface plasmon resonance, e.g., using an assay format as defined in Example 5 herein. In certain embodiments, the antibodies or antigen-binding fragments of the present invention bind CD3 with a $K_D$ of greater than about 15 nM, greater than about 20 nM, greater than about 25 nM, greater than about 30 nM, greater than about 35 nM, greater than about 40 nM, greater than about 45 nM, greater than about 50 nM, greater than about 55 nM, greater than about 60 nM, greater than about 65 nM, greater than about 70 nM, greater than about 75 nM, at least 80 nM, greater than about 90 nM, greater than about 100 nM, greater than about 110 nM, at least 120 nM, greater than about 130 nM, greater than about 140 nM, greater than about 150 nM, at least 160 nM, greater than about 170 nM, greater than about 180 nM, greater than about 190 nM, greater than about 200 nM, greater than about 250 nM, greater than about 300 nM, greater than about 1 $\mu$M, greater than about 2 $\mu$M, or greater than about 3 $\mu$M, or no detectable affinity, as measured by surface plasmon resonance, e.g., using an assay format as defined in Example 5 herein (e.g., mAb-capture or antigen-capture format), or a substantially similar assay.

The present invention includes antibodies, antigen-binding fragments, and bispecific antibodies thereof that bind human CD3 and induce T cell activation. For example, the present invention includes anti-CD3 antibodies that induce human T cell activation with an $EC_{50}$ value of less than about 113 pM, as measured by an in vitro T cell activation assay, e.g., using the assay format as defined in Example 6 herein [e.g., assessing the percent activated (CD69+) cells out of total T cells (CD2+) in the presence of anti-CD3 antibodies], or a substantially similar assay that assesses T cell in their activated state. In certain embodiments, the antibodies or antigen-binding fragments of the present invention induce human T cell activation [e.g., percent activated (CD69+) T cells] with an $EC_{50}$ value of less than about 100 pM, less than about 50 pM, less than about 20 pM, less than about 19 pM, less than about 18 pM, less than about 17 pM, less than about 16 pM, less than about 15 pM, less than about 14 pM, less than about 13 pM, less than about 12 pM, less than about 11 pM, less than about 10 pM, less than about 9 pM, less than about 8 pM, less than about 7 pM, less than about 6 pM, less than about 5 pM, less than about 4 pM, less than about 3 pM, less than about 2 pM, or less than about 1 pM, as measured by an in vitro T cell activation assay, e.g., using the assay format as defined in Example 6 herein, or a substantially similar assay. Anti-CD3 antibodies that have weak or no detectable binding to CD3 have the ability to induce T cell activation with high potency (i.e. pM range), despite having weak or no detectable binding affinity to CD3, as exemplified in Example 6 herein.

The present invention also includes antibodies, antigen-binding fragments, and bispecific antibodies that bind human CD3 and induce T cell-mediated killing of tumor antigen-expressing cells. For example, the present invention includes anti-CD3 antibodies that induce T cell-mediated killing of tumor cells with an $EC_{50}$ of less than about 1.3 nM, as measured in an in vitro T cell-mediated tumor cell killing assay, e.g., using the assay format as defined in Example 6 herein (e.g., assessing the extent of tumor antigen-expressing cells, such as PSMA-expressing, EGFRvlll-expressing or MUC16-expressing cell killing by human PBMCs in the presence of anti-CD3 antibodies), or a substantially similar assay. In certain embodiments, the antibodies or antigen-binding fragments of the present invention induce T cell-mediated tumor cell killing (e.g., PBMC-mediated killing of OVCAR3 cells) with an $EC_{50}$ value of less than about 1 nM, less than about 400 pM, less than about 250 pM, less than about 100 pM, less than about 50 pM, less than about 40 pM, less than about 30 pM, less than about 20 pM, less than about 10 pM, less than about 9 pM, less than about 8 pM, less than about 7 pM, less than about 6 pM, less than about 5 pM, less than about 4 pM, less than about 3 pM, less than about 2 pM, or less than about 1 pM, as measured by an in vitro T cell-mediated tumor cell killing assay, e.g., using the assay format as defined in Example 6 herein, or a substantially similar assay.

The present invention also includes antibodies, antigen-binding fragments, and bispecific antibodies that bind CD3 with a dissociative half-life (t½) of less than about 10 minutes as measured by surface plasmon resonance at 25° C. or 37° C., e.g., using an assay format as defined in Example 5 herein, or a substantially similar assay. In certain embodiments, the antibodies or antigen-binding fragments of the present invention bind CD3 with a t½ of less than about 9 minutes, of less than about 8 minutes, of less than about 7 minutes, of less than about 6 minutes, of less than about 5 minutes, of less than about 4 minutes, of less than about 3 minutes, of less than about 2 minutes, of less than about 1.9 minutes, or less than about 1.8 minutes, or exhibit very weak or no detectable binding as measured by surface plasmon resonance at 25° C. or 37° C., e.g., using an assay format as defined in Example 5 herein (e.g., mAb-capture or antigen-capture format), or a substantially similar assay.

The anti-CD3/anti-TAA bispecific antigen-binding molecules of the present invention may additionally exhibit one or more characteristics selected from the group consisting of: (a) inducing PBMC proliferation in vitro; (b) activating T-cells via inducing IFN-gamma release and CD25 up-regulation in human whole blood; and (c) inducing T-cell mediated cytotoxicity on anti-TAA-resistant cell lines.

The present invention includes anti-CD3/anti-TAA bispecific antigen-binding molecules which are capable of depleting tumor antigen-expressing cells in a subject (see, e.g., Example 7). For example, according to certain embodiments, anti-CD3/anti-PSMA, anti-CD3/anti-MUC16, or anti-CD3/anti-STEAP2 bispecific antigen-binding molecules are provided, wherein a single administration of 1 $\mu$g, or 10 $\mu$g, or 100 $\mu$g of the bispecific antigen-binding molecule to a subject (e.g., at a dose of about 0.1 mg/kg, about 0.08 mg/kg, about 0.06 mg/kg about 0.04 mg/kg, about 0.04 mg/kg, about 0.02 mg/kg, about 0.01 mg/kg, or less) causes a reduction in the number of tumor antigen-expressing cells in the subject (e.g., tumor growth in the subject is suppressed or inhibited) below detectable levels. In certain embodiments, a single administration of the anti-CD3/anti-PSMA bispecific antigen-binding molecule at a dose of about 0.4 mg/kg causes a reduction in tumor growth in the subject below detectable levels by about day 7, about day 6, about day 5, about day 4, about day 3, about day 2, or about day 1 after administration of the bispecific antigen-binding molecule to the subject. According to certain embodiments, a single administration of an anti-CD3/anti-PSMA bispecific antigen-binding molecule of the invention, at a dose of at least about 0.01 mg/kg, causes the number of PSMA-expressing tumor cells to remain below detectable levels until at least about 7 days, 8 days, 9 days, 10 days, 11 days, 12 days, 13 days, 14 days, 15 days, 16 days, 17 days or more, following the administration. As used herein, the expression "below detectable levels" means that no tumor cells can be directly or indirectly detected growing subcutaneously in a subject using standard caliper measurement methods, e.g., as set forth in Example 7, herein. In certain embodiments, a single administration of the anti-CD3/anti-MUC16 bispecific antigen-binding molecule at a dose of about 10 μg causes a suppression of tumor growth in the subject at about day 6, and maintains tumor suppression until at least day 26 after administration of the bispecific antigen-binding molecule to the subject. In subjects receiving a single administration of the anti-CD3/anti-MUC16 bispecific antigen-binding molecule at a dose of about 10 μg at least 7 days after tumor implantation, the bispecific antigen-binding molecule exhibits efficacy in suppression of established tumors from further growth in the subject at about day 26 after tumor implantation in the subject. According to certain embodiments, a single administration of an anti-CD3/anti-MUC16 bispecific antigen-binding molecule of the invention, at a dose of at least about 0.1 mg/kg, inhibits growth of MUC16-expressing tumor cells for at least about 7 days, 8 days, 9 days, 10 days, 11 days, 12 days, 13 days, 14 days, 15 days, 16 days, 17 days, 18 days, 19 days, 20 days or more, following administration of the bispecific molecule. See, e.g. Example 8.

In certain embodiments, a single administration of the anti-CD3/anti-STEAP2 bispecific antigen-binding molecule at a dose of about 0.1 mg/kg or 0.01 mg/kg maintains a suppression of tumor growth until at least day 46 after administration of the bispecific antigen-binding molecule and tumor to the subject. According to certain embodiments, a single administration of an anti-CD3/anti-STEAP2 bispecific antigen-binding molecule of the invention, at a dose of at least about 0.1 mg/kg, about 0.08 mg/kg, about 0.06 mg/kg, about 0.05 mg/kg, about 0.04 mg/kg, about 0.03 mg/kg, about 0.02 mg/kg, about 0.01 mg/kg, or less inhibits growth of STEAP2-expressing tumor cells for at least about 20 days, 30 days, 35 days, 40 days, 45 days or more, following administration of the bispecific molecule. See, e.g. Example 10.

In other embodiments, anti-CD3/anti-TAA bispecific antigen-binding molecules having a CD3 targeted binding arm having weak binding affinity to effector cells exhibit reduced drug elimination rates compared to the bispecific antibodies comprising the same anti-TAA binding arm and a strong CD3 binding arm administered in an in vivo pharmacokinetic study. The results suggest that the bispecific molecules comprising weaker binding of the CD3 targeting arm may exhibit beneficial drug exposure levels (AUC$_{last}$) and drug elimination profiles (antibody clearance). See, e.g., Example 9.

The present invention provides anti-CD3/anti-PSMA, anti-CD3/anti-MUC16 and anti-CD3/anti-STEAP2 bispecific antigen-binding molecules (i.e. anti-CD3/anti-TAA bispecific antigen-binding molecules) which exhibit one or more characteristics selected from the group consisting of: (a) inhibiting tumor growth in immunocompromised mice bearing human prostate cancer xenografts; (b) inhibiting tumor growth in immunocompetent mice bearing human prostate cancer xenografts; (c) suppressing tumor growth of established tumors in immunocompromised mice bearing human prostate cancer xenografts; and (d) reducing tumor growth of established tumors in immunocompetent mice bearing human prostate cancer xenografts (see, e.g., Examples 7, 8 and 10). The present invention also provides anti-CD3/anti-PSMA, anti-CD3/anti-MUC16 and anti-CD3/anti-STEAP2 bispecific antibodies (i.e. anti-CD3/anti-TAA bispecific antibodies) comprising a first heavy chain directed to an effector T cell (i.e. CD3), and ii) a second heavy chain directed to a target tumor cell, wherein the bispecific antibodies exhibit weak binding or no detectable binding to the effector cells, and exhibit tumor growth suppression and reduced antibody clearance (i.e. elimination) from the body compared to bispecific antibodies that exhibit strong binding to effector cells.

Epitope Mapping and Related Technologies

The epitope on CD3 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 protein. Alternatively, the epitope may consist of a plurality of non-contiguous amino acids (or amino acid sequences) of CD3. The antibodies of the invention may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267 (2): 252-259; Engen and Smith (2001) Anal.

Chem. 73: 256A-265A. X-ray crystallography of the antigen/antibody complex may also be used for epitope mapping purposes.

The present invention further includes anti-PSMA antibodies that bind to the same epitope as any of the specific exemplary antibodies described herein (e.g. antibodies comprising any of the amino acid sequences as set forth in Table 6 herein). Likewise, the present invention also includes anti-PSMA antibodies that compete for binding to PSMA with any of the specific exemplary antibodies described herein (e.g. antibodies comprising any of the amino acid sequences as set forth in Table 6 herein). Anti-PSMA antibodies disclosed in U.S. application Ser. No. 15/223,434 are herein incorporated by reference into this application.

The present invention also includes bispecific antigen-binding molecules comprising a first antigen-binding domain that specifically binds human CD3 and/or cynomolgus CD3 with low or detectable binding affinity, and a second antigen binding domain that specifically binds human tumor-associated antigen (TAA), wherein the first antigen-binding domain binds to the same epitope on CD3 as any of the specific exemplary CD3-specific antigen-binding domains described herein.

Likewise, the present invention also includes bispecific antigen-binding molecules comprising a first antigen-binding domain that specifically binds human CD3 and/or cynomolgus CD3 with low or detectable binding affinity, and a second antigen binding domain that specifically binds human tumor-associated antigen (TAA), wherein the first antigen-binding domain competes for binding to CD3 with any of the specific exemplary CD3-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD3 (or TAA) as a reference bispecific antigen-binding molecule of the present invention, the reference bispecific molecule is first allowed to bind to a CD3 protein (or TAA protein). Next, the ability of a test antibody to bind to the CD3 molecule is assessed. If the test antibody is able to bind to CD3 (or TAA) following saturation binding with the reference bispecific antigen-binding molecule, it can be concluded that the test antibody binds to a different epitope of CD3 (or TAA) than the reference bispecific antigen-binding molecule. On the other hand, if the test antibody is not able to bind to the CD3 (or TAA) molecule following saturation binding with the reference bispecific antigen-binding molecule, then the test antibody may bind to the same epitope of CD3 (or TAA) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. If the reference antibody is one that has no measurable binding as exemplified herein, then the reference antibody may be mutated back to germline sequence in order to determine binding to the CD3 for purpose of comparing epitope interaction, or comparing its binding properties to the test antibody as described herein. Experiments of this sort can be performed using ELISA, RIA, BIACORE™, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD3 protein (or TAA protein) under saturating conditions followed by assessment of binding of the test antibody to the CD3 (or TAA) molecule. In a second orientation, the test antibody is allowed to bind to a CD3 (or TAA) molecule under saturating conditions followed by assessment of binding of the reference antigen-binding molecule to the CD3 (or TAA) molecule. If, in both orientations, only the first (saturating) antigen-binding molecule is capable of binding to the CD3 (or TAA) molecule, then it is concluded that the test antibody and the reference antigen-binding molecule compete for binding to CD3 (or TAA). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope. If the reference antibody is one that has no measurable binding as exemplified herein, then the reference antibody may be mutated back to germline sequence in order to determine binding to the CD3 for purpose of comparing epitope interaction, or comparing its binding properties or blocking interaction with the test antibody as described herein.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and TAA), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or TAA) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa (κ) constant gene at the endogenous mouse kappa (κ) locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules). Antibodies of the invention may comprise immunoglobulin heavy chains associated with a common light chain. The common light chain may be derived from a cognate light chain of the anti-TAA heavy chain, or derived from a known or public domain light chain variable region derived from a light chain exhibiting promiscuity or ability to pair with a wide variety of non-cognate heavy chains, i.e. a universal or common light chain. Antibodies of the invention may comprise immunoglobulin heavy chains associated with a single rearranged light chain. In some embodiments, the light chain a variable domain derived from a human VK1-39 gene segment or a VK3-20 gene segment. In other embodiments, the light chain comprises a variable domain derived from a human VK1-39 gene segment rearranged with a human JK5 or a human JK1 gene segment, or a VK3-20 gene segment rearranged with a human JK1 gene segment, or a VK1-39 gene segment rearranged with a human JK1 gene segment.

Bioequivalents

The present invention encompasses antigen-binding molecules having amino acid sequences that vary from those of the exemplary molecules disclosed herein but that retain the ability to bind or interact with CD3 and/or TAA. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods.

Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which display weak or no interaction with human CD3 and weak or no interaction with CD3 from other species, such as cynomolgous monkey CD3. Also provided are antigen-binding molecules which bind to human TAA but not to TAA from other species. The present invention also includes antigen-binding molecules that bind to human CD3 and to CD3 from one or more non-human species; and/or antigen-binding molecules that bind to human TAA and to TAA from one or more non-human species.

According to certain exemplary embodiments of the invention, antigen-binding molecules are provided which bind weakly to human CD3 and/or human TAA and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or TAA. For example, in certain exemplary embodiments of the present invention bispecific antigen-binding molecules are provided comprising a first antigen-binding domain that weakly binds human CD3 and cynomolgus CD3, and a second antigen-binding domain that specifically binds human PSMA, MUC16, EGFRvlll or STEAP2.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081). Therapeutic Formulation and Administration The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN™ (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-tumor antibody or antigen-binding fragment thereof, or a bispecific antigen-binding molecule that specifically binds weakly or has no detectable binding to CD3 and binds a tumor-associated antigen. The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in tumor activity or a depletion of tumor cells (e.g., PSMA++prostate cancer cells).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the bispecific antigen-binding molecules of the present invention may be used for the treatment, prevention and/or amelioration of any disease or disorder associated with or mediated by a cell expressing a TAA, e.g. PSMA expression or activity or the proliferation of PSMA+ cells. The mechanism of action by which the therapeutic methods of the invention are achieved include killing of the cells expressing tumor-associated antigens, in the presence of effector cells, for example, by CDC, apoptosis, ADCC, phagocytosis, or by a combination of two or more of these mechanisms. Cells expressing tumor-associated antigens, such as PSMA, MUC16, STEAP2 or EGFRvlll, which can be inhibited or killed using the bispecific antigen-binding molecules of the invention include, for example, prostate tumor cells.

The antigen-binding molecules of the present invention may be used to treat, e.g., primary and/or metastatic tumors arising in the brain and meninges, head and neck, oropharynx, lung and bronchial tree, gastrointestinal tract, male and female reproductive tract, muscle, bone, skin and appendages, connective tissue, spleen, immune system, blood forming cells and bone marrow, liver and urinary tract, kidney, bladder and/or special sensory organs such as the eye. In certain embodiments, the bispecific antigen-binding molecules of the invention are used to treat one or more of, but not limited to, the following cancers: pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, melanomaglioma, breast cancer (e.g. ductal or intraductal breast carcinoma, squamous cell carcinoma, esophageal cancer, clear cell renal cell carcinoma, chromophobe renal cell carcinoma, (renal) oncocytoma, (renal) transitional cell carcinoma, urothelial carcinoma, (bladder) adenocarcinoma, or (bladder) small cell carcinoma. According to certain embodiments of the present invention, the bispecific antibodies are useful for treating a patient afflicted with a refractory or treatment-resistant cancer, e.g. castrate-resistant prostate cancer. According to exemplary embodiments of the invention, methods are provided comprising administering an anti-CD3/anti-PSMA bispecific antigen-binding molecule as disclosed herein to a patient who is afflicted with a castrate-resistant prostate cancer. Analytic/diagnostic methods known in the art, such as tumor scanning, etc., may be used to ascertain whether a patient harbors a tumor that is castrate-resistant.

The present invention also includes methods for treating residual cancer in a subject. As used herein, the term "residual cancer" means the existence or persistence of one or more cancerous cells in a subject following treatment with an anti-cancer therapy, such as a first-line or standard therapy.

According to certain aspects, the present invention provides methods for treating a cancer associated with TAA expression (e.g., prostate cancer associated with PSMA expression or STEAP2 expression, glioblastoma associated with EGFRvlll expression, or ovarian cancer associated with MUC16 expression) comprising administering one or more of the bispecific antigen-binding molecules described elsewhere herein to a subject after the subject has been determined to have the cancer. For example, the present invention includes methods for treating prostate cancer comprising administering an anti-CD3/anti-TAA bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received a previous therapy.

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g. an anti-PD-L1 antibody as described in in U.S. Pat. Appln. Pub. No. US2015/0203580A1), an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvlll (e.g., an antibody that specifically binds EGFRvlll), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 (PSMA) antagonist, a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), etc. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD3/anti-PSMA bispecific antigen-binding molecule as disclosed herein) may also be administered as part of a therapeutic regimen comprising one or more therapeutic combinations selected from "ICE": ifosfamide (e.g., Ifex@), carboplatin (e.g., Paraplatin®), etoposide (e.g., Etopophos®, Toposar®, VePesid®, VP-16); "DHAP": dexamethasone (e.g., Decadron@), cytarabine (e.g., Cytosar-U®, cytosine arabinoside, ara-C), cisplatin (e.g., Platinol®-AQ); and "ESHAP": etoposide (e.g., Etopophos®, Toposar®, VePesid@, VP-16), methylprednisolone (e.g., Medrol@), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvlll, cMet, IGF1R, B-raf, PDGFR-α, PDGFR-β, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F (ab') 2 fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of the bispecifc antigen-binding molecule (e.g., an anti-TAA bispecific antigen-binding molecule) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 11/2, 2, 21/2, 3, 31/2, 4, 41/2, 5, 51/2, 6, 61/2, 7, 71/2, 8, 81/2, 9, 91/2, 10, 101/2, 11, 111/2, 12, 121/2, 13, 131/2, 14, 141/2, 15, 151/2, 16, 161/2, 17, 171/2, 18, 181/2, 19, 191/2, 20, 201/2, 21, 211/2, 22, 221/2, 23, 231/2, 24, 241/2, 25, 251/2, 26, 261/2, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-TAA bispecific antigen-binding molecule). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-CD3 Antibodies

The following procedures were aimed at identifying antibodies that specifically recognized CD3 (T cell co-receptor) as an antigen.

A pool of anti-CD3 antibodies were derived by immunizing genetically modified mice. Briefly, mice genetically engineered to express reverse chimeric (human variable, mouse constant) and immunoglobulin heavy chains associated with a single rearranged light chain (e.g., a VK1-39/J or a VK3-20/J), were immunized with a CD3 antigen and generated B cells that comprised a diversity of human VH rearrangements in order to express a diverse repertoire of high-affinity antigen-specific antibodies. Certain exemplified antibodies described in the subject application have been made recombinantly and express the same light chain sequence of VK1-39JK5 (LCVR set forth in SEQ ID NO: 162), while other antibodies made recombinantly express a cognate light chain of one of the heavy chain arms (e.g. the tumor target arm).

Generated antibodies were tested for affinity to human and cynomolgus monkey CD3 antigen in an in vitro binding assay, and e.g. one CD3 antibody: designated CD3-VH-P (HCVR set forth in SEQ ID NO: 154) was identified, amongst a few others, that were found to bind to both human and cyno CD3 having an $EC_{50}$ between 1 and 40 nM affinity (+++), as determined in a FACS titration of Jurkat cells and cynomolgus T cells, respectively. See, e.g. FACS binding experiments outlined in Example 4 herein below.

Figure 1:
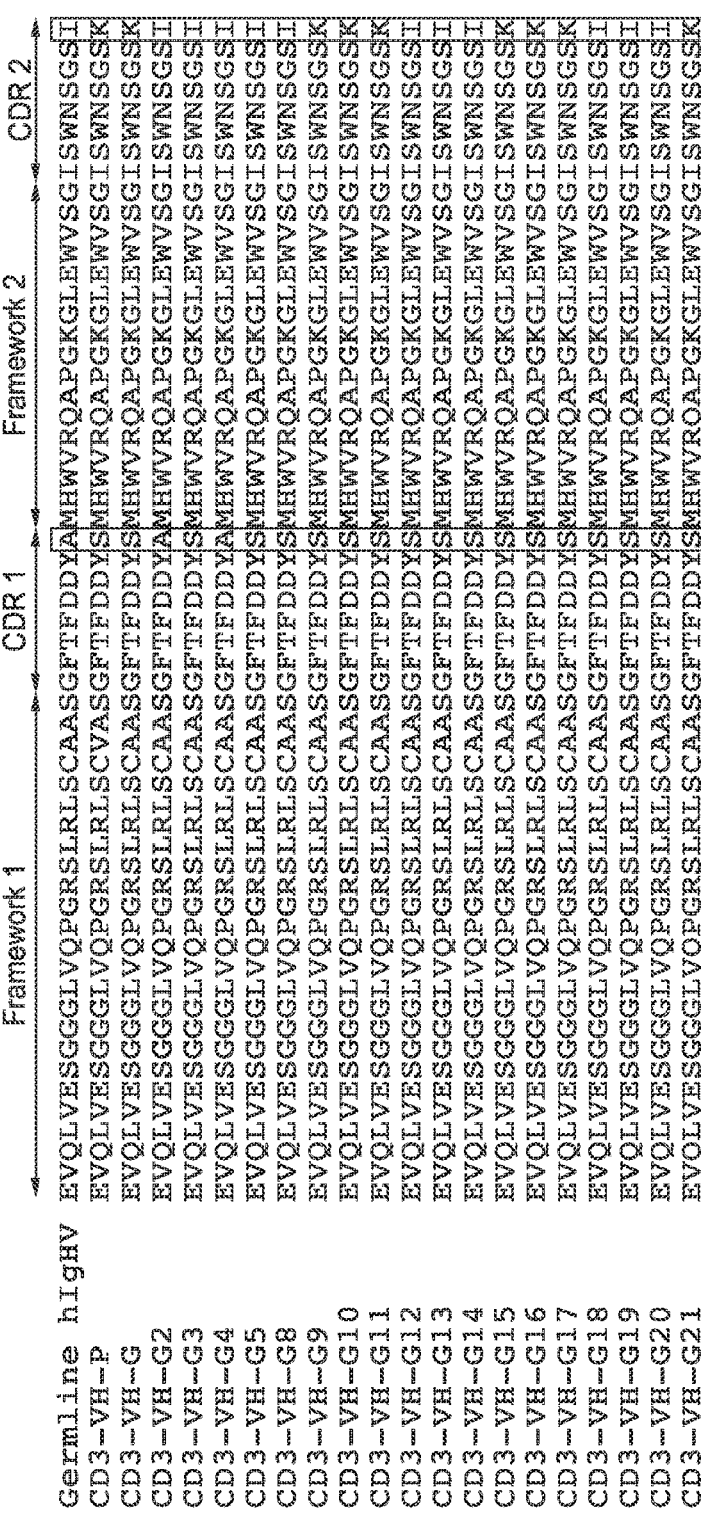
FIG. 1 shows the amino acid alignment of the following antibody heavy chain variable region (HCVR) sequences.
Figure 1:
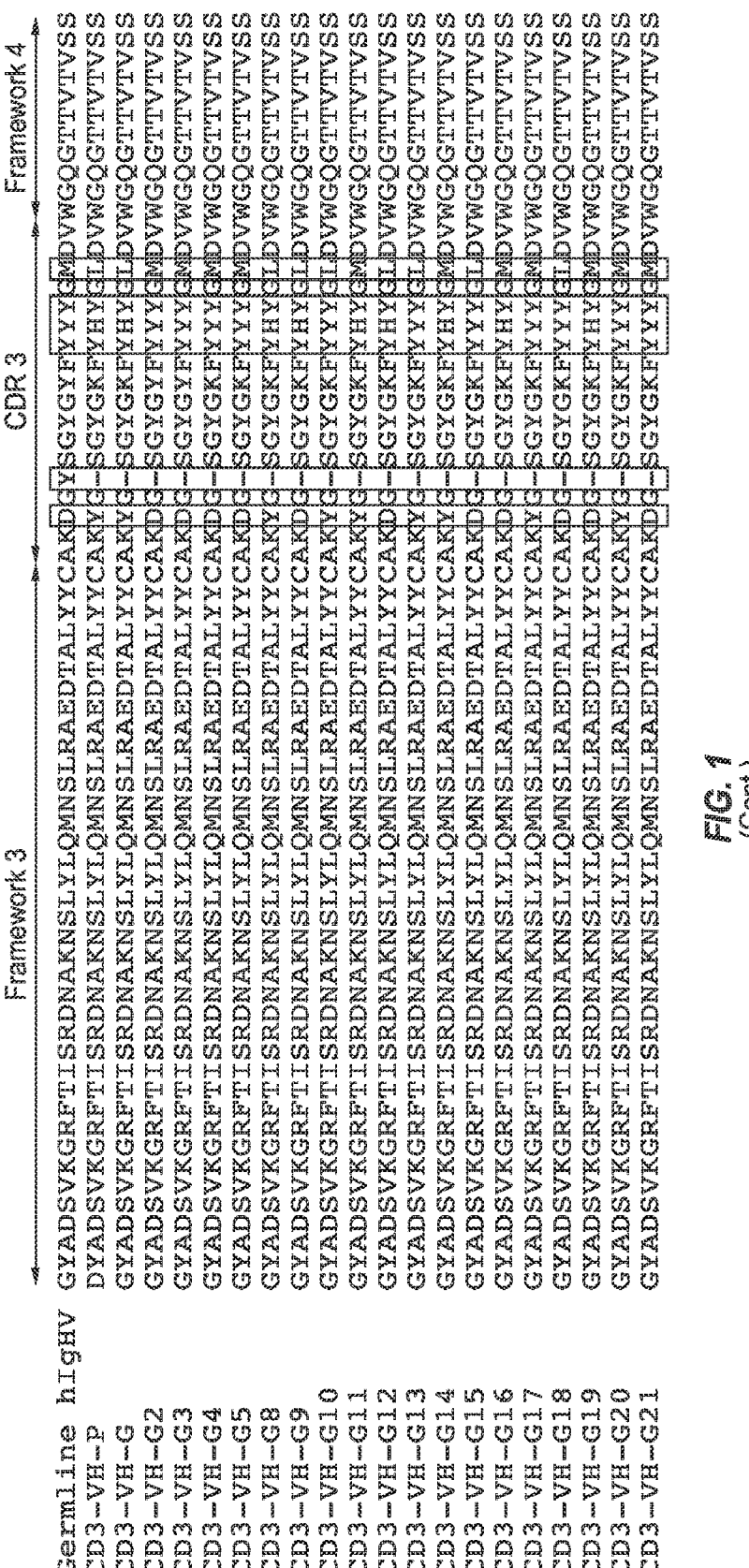

The germline amino acid residues of CD3-VH-P were subsequently identified and an antibody designated "CD3-VH-G" was engineered to contain only germline frameworks. Other antibody derivatives were engineered by well-known molecular cloning techniques to replace amino acid residues in a stepwise manner based on differences between the germline sequence and the CD3-VH-P sequence. Each antibody derivative is given a "CD3-VH-G" number designation. See Table 1 and FIG. 1.

Bispecific antibodies, comprising a first binding arm derived from the engineered anti-CD3 antibodies with the designations and descriptions shown in Table 1, and a second binding arm derived from anti-TAA antibodies, were prepared and tested for monovalent affinity to CD3-bearing cells in a FACS assay (as described in Example 4). The monovalent binding affinity results of these bispecific antibodies are shown in the two right columns of Table 1. In specific examples, bispecific antibodies having a TAA-binding arm and a CD3-binding arm with designations "CD3-VH-G," "CD3-VH-G5," and "CD3-VH-G20," respectively, bound Jurkat cells with an $EC_{50}$ of 2.7E-08, no detectable binding, and 5.5E-07, respectively.

TABLE 1

Mutations to CDRs Based on the Germline Sequence and Corresponding FACS Binding Affinity for Each Engineered Antibody

| Antibody CD3-VH Designation | Description of Mutations compared to antibody CD3-VH-G* | JURKAT | cyno T cells |
|---|---|---|---|
| CD3-VH-G | Germline (GL) only framework regions (FRs); CD3-VHP CDRs | (+ + +) | (+ + +) |
| CD3-VH-G2 | All GL (FRs and CDRs). | (−) | (−) |
| CD3-VH-G3 | All GL (FRs and CDRs). Add back A33S. | (−) | (−) |
| CD3-VH-G4 | All GL (FRs and CDRs). Add back Y105K. | (−) | (−) |
| CD3-VH-G5 | All GL (FRs and CDRs). Add back A33S and Y105K. | (−) | (−) |
| CD3-VH-G8 | Germline frameworks. Add back K58I | (+ + +) | (+) |
| CD3-VH-G9 | Germline frameworks. Add backY99D | (+) | (−) |
| CD3-VH-G10 | Germline frameworks. Add back H108Y | (+) | (−) |
| CD3-VH-G11 | Germline frameworks. Add back L111M | (+ + +) | (+) |
| CD3-VH-G12 | Germline frameworks. Add back K58I, Y99D | (+ +) | (+/−) |
| CD3-VH-G13 | Germline frameworks. Add back K58I, H108Y | (+ +) | (+) |
| CD3-VH-G14 | Germline frameworks. Add back K58I, L111M | (+ + +) | (+ +) |
| CD3-VH-G15 | Germline frameworks. Add back Y99D,-H108Y | (+) | (−) |
| CD3-VH-G16 | Germline frameworks. Add back Y99D, L111M | (+ +) | (+/−) |
| CD3-VH-G17 | Germline frameworks. Add back H108Y , L111M | (+/−) | (+/−) |
| CD3-VH-G18 | Germline frameworks. Add back K58I, Y99D, H108Y | (+/−) | (−) |
| CD3-VH-G19 | Germline frameworks. Add back K58I, Y99D, L111M | (+/−) | (−) |
| CD3-VH-G20 | Germline frameworks. Add back K58I, H108Y, L111M | (+/−) | (+/−) |
| CD3-VH-G21 | Germline frameworks. Add back Y99D, H108Y, −L111M | (+/−) | (−) |

*Sequential numbering based on 7221G (CD3-VH-G) mature protein

While CD3-VH-G and some other engineered antibodies retained their binding affinity as seen in the FACS assays, several anti-CD3 antibodies bound to human or cyno CD3 in vitro with weak (+/−) to no (−) measurable affinity. Binding affinities, binding kinetics, and other biological properties to elucidate toxicity and pharmacokinetic (pK) profiles were subsequently investigated for bispecific antibodies comprising the exemplary anti-CD3 antibodies generated in accordance with the methods of this Example, and are described in detail in the Examples set forth below.

Example 2: Heavy and Light Chain Variable Regions (Amino Acid and Nucleic Acid Sequences of the CDRs)

Amino acid and nucleic acid sequences were determined for each antibody heavy chain sequence. Each antibody heavy chain, as a derivative of the germline sequence IGHV3-9*01/D5-12*01/J6*02 (SEQ ID NO: 181) was assigned a "G" number designation for consistent nomenclature. Table 2 sets forth the amino acid sequence identifiers of the heavy chain variable regions and CDRs of the engineered anti-CD3 antibodies of the invention. The corresponding nucleic acid sequence identifiers are set forth in Table 3. The amino acid and nucleic acid sequence identifiers of the light chain variable region and CDRs to construct each recombinant antibody are also identified below in Tables 4 and 5, respectively.

TABLE 2

Heavy Chain Amino Acid Sequence Identifiers

| Antibody CD3-VH | SEQ ID NOS: | | | |
|---|---|---|---|---|
| Designation | HCVR | CDR1 | CDR2 | CDR3 |
| CD3-VH-G | 2 | 4 | 6 | 8 |
| CD3-VH-G2 | 10 | 12 | 14 | 16 |
| CD3-VH-G3 | 18 | 20 | 22 | 24 |
| CD3-VH-G4 | 26 | 28 | 30 | 32 |
| CD3-VH-G5 | 34 | 36 | 38 | 40 |
| CD3-VH-G8 | 42 | 44 | 46 | 48 |
| CD3-VH-G9 | 50 | 52 | 54 | 56 |
| CD3-VH-G10 | 58 | 60 | 62 | 64 |
| CD3-VH-G11 | 66 | 68 | 70 | 72 |
| CD3-VH-G12 | 74 | 76 | 78 | 80 |
| CD3-VH-G13 | 82 | 84 | 86 | 88 |
| CD3-VH-G14 | 90 | 92 | 94 | 96 |
| CD3-VH-G15 | 98 | 100 | 102 | 104 |
| CD3-VH-G16 | 106 | 108 | 110 | 112 |
| CD3-VH-G17 | 114 | 116 | 118 | 120 |
| CD3-VH-G18 | 122 | 124 | 126 | 128 |
| CD3-VH-G19 | 130 | 132 | 134 | 136 |
| CD3-VH-G20 | 138 | 140 | 142 | 144 |
| CD3-VH-G21 | 146 | 148 | 150 | 152 |
| CD3-VH-P | 154 | 156 | 158 | 160 |

TABLE 3

Heavy Chain Nucleic Acid Sequence Identifiers

| Antibody CD3-VH | SEQ ID NOS: | | | |
|---|---|---|---|---|
| Designation | HCVR | CDR1 | CDR2 | CDR3 |
| CD3-VH-G | 1 | 3 | 5 | 7 |
| CD3-VH-G2 | 9 | 11 | 13 | 15 |
| CD3-VH-G3 | 17 | 19 | 21 | 23 |
| CD3-VH-G4 | 25 | 27 | 29 | 31 |
| CD3-VH-G5 | 33 | 35 | 37 | 39 |
| CD3-VH-G8 | 41 | 43 | 45 | 47 |
| CD3-VH-G9 | 49 | 51 | 53 | 55 |
| CD3-VH-G10 | 57 | 59 | 61 | 63 |
| CD3-VH-G11 | 65 | 67 | 69 | 71 |
| CD3-VH-G12 | 73 | 75 | 77 | 79 |
| CD3-VH-G13 | 81 | 83 | 85 | 87 |
| CD3-VH-G14 | 89 | 91 | 93 | 95 |
| CD3-VH-G15 | 97 | 99 | 101 | 103 |
| CD3-VH-G16 | 105 | 107 | 109 | 111 |

TABLE 3-continued

Heavy Chain Nucleic Acid Sequence Identifiers

| Antibody CD3-VH | SEQ ID NOS: | | | |
|---|---|---|---|---|
| Designation | HCVR | CDR1 | CDR2 | CDR3 |
| CD3-VH-G17 | 113 | 115 | 117 | 119 |
| CD3-VH-G18 | 121 | 123 | 125 | 127 |
| CD3-VH-G19 | 129 | 131 | 133 | 135 |
| CD3-VH-G20 | 137 | 139 | 141 | 143 |
| CD3-VH-G21 | 145 | 147 | 149 | 151 |
| CD3-VH-P | 153 | 155 | 157 | 159 |

TABLE 4

Light Chain Amino Acid Sequence Identifiers

| Antibody ULC | SEQ ID NOS: | | | |
|---|---|---|---|---|
| Designation | LCVR | CDR1 | CDR2 | CDR3 |
| VK1-39JK5 | 162 | 164 | 166 | 168 |

TABLE 5

Light Chain Nucleic Acid Sequence Identifiers

| Antibody ULC | SEQ ID NOS: | | | |
|---|---|---|---|---|
| Designation | LCVR | CDR1 | CDR2 | CDR3 |
| VK1-39JK5 | 161 | 163 | 165 | 167 |

Control 1 antibody designated "CD3-L2K" was constructed based on a known anti-CD3 antibody (i.e., the anti-CD3 antibody "L2K" as set forth in WO2004/106380).

Isotype Control Antibody, referred to in the Examples hereinbelow, is an isotype matched (modified IgG4) antibody that interacts with an irrelevant antigen, i.e. FelD1 antigen.

Example 3: Generation of ULC Bispecific Antibodies that Bind CD3 and Tumor-Associated Antigens (TAA)

Bispecific antibodies comprising an anti-CD3-specific binding domain and an anti-TAA-specific binding domain, such as PSMA, EGFRvIII, MUC16, or STEAP2, were constructed using standard molecular biology methodologies utilizing a heavy chain from an anti-CD3 antibody described herein, a heavy chain from an anti-TAA antibody and a common light chain or a universal light chain (ULC). The anti-TAA antibodies used to construct the bispecific antibodies of this invention were obtained by immunizing genetically modified mice.

A summary of the component parts of the antigen-binding domains of the various bispecific antibodies made in accordance with this Example is set forth below in Tables 6, 7 and 8. All bispecific antibodies were manufactured having a modified (chimeric) IgG4 Fc domain as set forth in US Patent Application Publication No. US20140243504A1, published on Aug. 28, 2014. Exemplary EGFRvIIIxCD3 bispecific antibodies can be prepared using any of the heavy chain and light chain variable regions (or CDRs) of any of the EGFRvIII antibodies discussed in US Patent Application Publication NO. US20150259423, which is hereby incorporated by reference in its entirety, in combination with the variable regions or CDRs of any of the anti-CD3 antibodies discussed herein.

TABLE 6

Construction of PSMAxCD3 Bispecific Antibodies

| Bispecific Antibody Identifier | Anti-PSMA Antigen-Binding Domain Heavy Chain Variable Region | Anti-CD3 Antigen-Binding Domain Heavy Chain Variable Region | Common Light Chain Variable Region |
|---|---|---|---|
| BSPSMA/CD3-003 | PSMA-VH-B | CD3-VH-G | Vκ1-39JK5 |
| BSPSMA/CD3-200 | | CD3-VH-G2 | |
| BSPSMA/CD3-300 | | CD3-VH-G3 | |
| BSPSMA/CD3-400 | | CD3-VH-G4 | |
| BSPSMA/CD3-004 | | CD3-VH-G5 | |
| BSPSMA/CD3-800 | | CD3-VH-G8 | |
| BSPSMA/CD3-900 | | CD3-VH-G9 | |
| BSPSMA/CD3-1000 | | CD3-VH-G10 | |
| BSPSMA/CD3-1100 | | CD3-VH-G11 | |
| BSPSMA/CD3-1200 | | CD3-VH-G12 | |
| BSPSMA/CD3-1300 | | CD3-VH-G13 | |
| BSPSMA/CD3-1400 | | CD3-VH-G14 | |
| BSPSMA/CD3-1500 | | CD3-VH-G15 | |
| BSPSMA/CD3-1600 | | CD3-VH-G16 | |
| BSPSMA/CD3-1700 | | CD3-VH-G17 | |
| BSPSMA/CD3-1800 | | CD3-VH-G18 | |
| BSPSMA/CD3-1900 | | CD3-VH-G19 | |
| BSPSMA/CD3-005 | | CD3-VH-G20 | |
| BSPSMA/CD3-2100 | | CD3-VH-G21 | |

TABLE 7

Construction of EGFRvIII xCD3 Bispecific Antibodies

| Bispecific Antibody Identifier | Anti-EGFRvIII Antigen-Binding Domain Heavy Chain Variable Region | Anti-CD3 Antigen-Binding Domain Heavy Chain Variable Region | Common Light Chain Variable Region |
|---|---|---|---|
| BSV3/CD3-001 | EGFRvIII-VH-A | CD3-VH-G | EGFRvIII-VL-A |
| BSV3/CD3-002 | | CD3-VH-G5 | |
| BSV3/CD3-003 | | CD3-VH-G9 | |
| BSV3/CD3-004 | | CD3-VH-G10 | |

TABLE 8

Construction of MUC16xCD3 Bispecific Antibodies

| Bispecific Antibody Identifier | Anti-MUC16 Antigen-Binding Domain Heavy Chain Variable Region | Anti-CD3 Antigen-Binding Domain Heavy Chain Variable Region | Common Light Chain Variable Region |
|---|---|---|---|
| BSMUC16/CD3-001 | MUC16-VH-A | CD3-VH-G | MUC16-VL-A |
| BSMUC16/CD3-002 | | CD3-VH-G5 | |
| BSMUC16/CD3-003 | | CD3-VH-G9 | |
| BSMUC16/CD3-004 | | CD3-VH-G10 | |
| BSMUC16/CD3-005 | | CD3-VH-G20 | |

TABLE 9

Construction of STEAP2xCD3 Bispecific Antibodies

| Bispecific Antibody Identifier | Anti-STEAP2 Antigen-Binding Domain Heavy Chain Variable Region | Anti-CD3 Antigen-Binding Domain Heavy Chain Variable Region | Common Light Chain Variable Region |
|---|---|---|---|
| BSSTEAP2/CD3-001 | STEAP2-VH-A | CD3-VH-G | STEAP2-VL-A |
| BSSTEAP2/CD3-002 | | CD3-VH-G5 | |
| BSSTEAP2/CD3-003 | | CD3-VH-G20 | |

Each of the exemplary bispecific antibodies were tested in various bioassays as described herein below.

Example 4: Binding Affinities of Exemplified Bispecific Antibodies as Measured by FACS Analysis In this example, the ability of CD3×TAA bispecific antibodies to bind to human and cynomolgus CD3-expressing cell lines via FACS was determined. Additionally, the ability of these bispecific antibodies to bind to target-specific (TAA-specific) cell lines was also confirmed. As described above, the various bispecific antibodies of this invention utilized a single TAA-specific binding arm (PSMA, EGFRvlll, MUC16, or STEAP2; see Example 3, Tables 6, 7 and 8) paired with one of a panel of anti-CD3 binding arms (see Examples 1 and 2 hereinabove) and a common light chain. As is also shown in Example 5, the CD3×TAA bispecific antibodies displayed a range of affinities to human soluble heterodimeric hCD3E/8.mFc protein via surface plasmon resonance.

Briefly, $2 \times 10^5$ cells/well of human CD3-expressing Jurkat, cynomolgus T or TAA-specific expressing cells were incubated with a serial dilution of bispecific antibodies for 30 min at 4° C. After incubation, cells were washed and a goat F (ab')>anti-human Fcγ PE labeled secondary (Jackson Immunolabs) was added to the cells for an additional 30 min. Next, cells were washed, re-suspended in cold PBS+ 1% BSA and analyzed via flow cytometry on a BD FACS CANTO™.

For FACS analysis, cells were gated by forward scatter height vs. forward scatter area for single events selection, followed by side and forward scatters. The $EC_{50}$ for cell binding titration was determined using PRISM™ software (GraphPad Software, Inc., La Jolla, CA). Values were calculated using 4-parameter non-linear regression analysis.

TABLE 10A

FACS Binding on CD3 and PSMA-Specific Cell lines

| Bispecific Antibody Identifier | Anti-CD3-Binding Arm | Jurkat $EC_{50}$ [M] | Cyno T-cells $EC_{50}$ [M] | B16F10.9/PSMA $EC_{50}$ [M] |
|---|---|---|---|---|
| BSPSMA/CD3-003 | CD3-VH-G | 1.65E−08 | 1.42E−08 | 2.26E−09 |
| BSPSMA/CD3-200 | CD3-VH-G2 | NB | NB | 1.88E−09 |
| BSPSMA/CD3-300 | CD3-VH-G3 | NB | NB | 1.90E−09 |
| BSPSMA/CD3-400 | CD3-VH-G4 | NB | NB | 1.72E−09 |
| BSPSMA/CD3-004 | CD3-VH-G5 | Very weak | NB | 1.31E−09 |
| BSPSMA/CD3-800 | CD3-VH-G8 | 1.93E−08 | 1.96E−08 | 1.31E−09 |
| BSPSMA/CD3-900 | CD3-VH-G9 | 2.74E−07 | NB | 1.43E−09 |
| BSPSMA/CD3-1000 | CD3-VH-G10 | 2.77E−07 | NB | 1.19E−09 |
| BSPSMA/CD3-1100 | CD3-VH-G11 | 1.83E−08 | 8.90E−07 | 1.03E−09 |
| BSPSMA/CD3-1200 | CD3-VH-G12 | 4.72E−08 | NB | 1.16E−09 |
| BSPSMA/CD3-1300 | CD3-VH-G13 | 1.02E−07 | 2.17E−06 | 1.25E−09 |
| BSPSMA/CD3-1400 | CD3-VH-G14 | 3.19E−08 | 1.70E−07 | 1.30E−09 |
| BSPSMA/CD3-1500 | CD3-VH-G15 | 9.30E−08 | NB | 1.21E−09 |

TABLE 10A-continued

FACS Binding on CD3 and PSMA-Specific Cell lines

| Bispecific Antibody Identifier | Anti-CD3-Binding Arm | Jurkat EC$_{50}$ [M] | Cyno T-cells EC$_{50}$ [M] | B16F10.9/ PSMA EC$_{50}$ [M] |
|---|---|---|---|---|
| BSPSMA/CD3-1600 | CD3-VH-G16 | 5.68E−08 | NB | 1.03E−09 |
| BSPSMA/CD3-1700 | CD3-VH-G17 | 2.00E−07 | 3.35E−06 | 1.34E−09 |
| BSPSMA/CD3-1800 | CD3-VH-G18 | 1.26E−07 | NB | 2.16E−09 |
| BSPSMA/CD3-1900 | CD3-VH-G19 | 6.07E−08 | NB | 1.35E−09 |
| BSPSMA/CD3-005 | CD3-VH-G20 | 2.10E−07 | 6.14E−06 | 2.09E−09 |
| BSPSMA/CD3-2100 | CD3-VH-G21 | 1.06E−07 | NB | 1.14E−09 |

TABLE 10B

FACS Binding on CD3 and EGFRvIII-Specific Cell lines

| Bispecific Antibody Identifier | Anti-CD3 Binding Arm | Jurkat EC$_{50}$ [M] | Cyno T-Cells EC$_{50}$ [M] | U87/ EGFRvIII EC$_{50}$ [M] |
|---|---|---|---|---|
| BSV3/CD3-001 | CD3-VH-G | 1.46E−09 | NT | 2.40E−09 |
| BSV3/CD3-002 | CD3-VH-G5 | Very weak | NT | 5.60E−09 |

TABLE 10C

FACS Binding on CD3 and MUC16-Specific Cell lines

| Bispecific Antibody Identifier | Anti-CD3 Binding Arm | Jurkat EC$_{50}$ [M] | Cyno T-cells EC$_{50}$ [M] | OVCAR3 (MUC16+) EC$_{50}$ [M] |
|---|---|---|---|---|
| BSMUC16/CD3-001 | CD3-VH-G | 3.21E−09 | NT | 1.20E−09 |
| BSMUC16/CD3-002 | CD3-VH-G5 | Very weak | NT | 2.69E−09 |

As shown in Table 10A, the CD3 binding arms of each CD3×PSMA bispecific antibody displayed a range of cell binding affinity to human CD3 expressing Jurkat cells (15 to 300 nM EC$_{50}$ range). Importantly, the CD3 arms that showed weak-to-no binding to human CD3 heterodimeric protein via surface plasmon resonance (see Table 11 hereinbelow) also correlated with weak to no observable binding on Jurkat cells (i.e. CD3-VH-G2, CD3-VH-G3, CD3-VH-G5). Non-detectable binding, or no detectable binding, in the FACS assay or equivalent assay means that the affinity between the antibody and its target antigen is beyond the detection limit of the assay (e.g. >1 μM). Several CD3-binding arms also displayed cross reactivity to cynomolgus T-cells. All tested bispecific antibodies displayed similar cell binding on respective PSMA, EGFRvIII and MUC16-expressing cell lines, confirming that bispecific pairing with individual CD3 arms did not affect or diminish TAA-specific binding (TAA-specific binding was less than or equal to 5.6 nM (high affinity) in all examples tested).

Antibodies exhibiting weak-to-no detectable binding to human CD3, and also exhibiting weak-to-no binding to cynomolgus CD3, are considered advantageous for avidity-driven bispecific pairing in accordance with the present invention, and were further tested for cytotoxicity in in vitro and in vivo assays.

Example 5: Binding Affinities of Exemplified Antibodies as Measured by a Surface Plasmon Resonance Binding Assay Binding affinities and kinetic constants of anti-TAA ×anti-CD3 bispecific antibodies to soluble heterodimeric hCD3ε/δ.mFc protein (hCD3ε=UniProtKB/Swiss-Prot: P07766.2; SEQ_ID NO: 169; hCD3δ=UniProtKB/Swiss-Prot: P04234.1, SEQ ID NO: 170) were determined by surface plasmon resonance at 37° C. using either an antigen-capture format (Table 11) or an antibody-capture format (data not shown). In this example, BSPSMA/CD3 bispecific antibodies were utilized as these pairings represented the use of a wider panel of antibodies for the CD3 binding arm. Measurements were conducted on a Sierra Sensors MASS-1 instrument.

In the antigen-capture format, the MASS-1 high-density amine sensor surface was derivatized with a goat anti-mouse IgG2a polyclonal antibody (Southern Biotech). Soluble heterodimeric CD3 protein was captured and the respective antibodies were injected over the captured antigen.

Kinetic association (ka) and dissociation (ka) rate constants were determined by processing and fitting the data to a 1:1 binding model using MASS-1 AnalyserR2 curve fitting software. Binding dissociation equilibrium constants (K$_D$) and dissociative half-lives (t½) were calculated from the kinetic rate constants as: K$_D$(M)=k$_d$/k$_a$; and t$_{1/2}$ (min)= (ln2/(60*k$_d$).

TABLE 11

Affinities of anti-CD3 Bispecific Antibodies to Soluble Human CD3

| Bispecific Antibody Identifier | Corresponding anti-CD3 Antigen-Binding HCVR Identifier | ka (Ms⁻¹) | kd (s⁻¹) | K$_D$ (M) | T½ (min) |
|---|---|---|---|---|---|
| | | Binding at 37° C./Antigen-Capture Format | | | |
| BSPSMA/CD3-003 | CD3-VH-G | 1.32E+05 | 7.62E−04 | 5.78E−09 | 15.2 |
| BSPSMA/CD3-200 | CD3-VH-G2 | NB | NB | NB | NB |
| BSPSMA/CD3-300 | CD3-VH-G3 | NB | NB | NB | NB |
| BSPSMA/CD3-400 | CD3-VH-G4 | NB | NB | NB | NB |
| BSPSMA/CD3-004 | CD3-VH-G5 | NB | NB | NB | NB |
| BSPSMA/CD3-800 | CD3-VH-G8 | 5.95E+04 | 1.15E−03 | 1.94E−08 | 10.0 |
| BSPSMA/CD3-900 | CD3-VH-G9 | 4.38E+04 | 4.95E−03 | 1.13E−07 | 2.3 |
| BSPSMA/CD3-1000 | CD3-VH-G10 | 3.44E+04 | 6.37E−03 | 1.85E−07 | 1.8 |
| BSPSMA/CD3-1100 | CD3-VH-G11 | 9.21E+04 | 1.02E−03 | 1.11E−08 | 11.3 |
| BSPSMA/CD3-1200 | CD3-VH-G12 | 3.85E+04 | 2.47E−03 | 6.42E−08 | 4.7 |
| BSPSMA/CD3-1300 | CD3-VH-G13 | 2.03E+04 | 2.48E−03 | 1.22E−07 | 4.7 |
| BSPSMA/CD3-1400 | CD3-VH-G14 | 6.21E+04 | 3.31 E−03 | 5.33E−08 | 3.5 |
| BSPSMA/CD3-1500 | CD3-VH-G15 | 7.36E+04 | 6.11E−03 | 8.29E−08 | 1.9 |
| BSPSMA/CD3-1600 | CD3-VH-G16 | 6.43E+04 | 2.43E−03 | 3.78E−08 | 4.7 |

TABLE 11-continued

Affinities of anti-CD3 Bispecific Antibodies to Soluble Human CD3

Binding at 37° C./Antigen-Capture Format

| Bispecific Antibody Identifier | Corresponding anti-CD3 Antigen-Binding HCVR Identifier | ka (Ms$^{-1}$) | kd (s$^{-1}$) | K$_D$ (M) | T$^{1/2}$ (min) |
|---|---|---|---|---|---|
| BSPSMA/CD3-1700 | CD3-VH-G17 | 4.70E+04 | 3.07E−03 | 6.52E−08 | 3.8 |
| BSPSMA/CD3-1800 | CD3-VH-G18 | NB | NB | NB | NB |
| BSPSMA/CD3-1900 | CD3-VH-G19 | 4.43E+04 | 5.09E−03 | 1.15E−07 | 2.3 |
| BSPSMA/CD3-005 | CD3-VH-G20 | 1.73E+04 | 5.77E−03 | 3.34E−07 | 2.0 |
| BSPSMA/CD3-2100 | CD3-VH-G21 | 3.02E+04 | 2.34E−03 | 7.75E−08 | 4.9 |
| Control 1 | CD3-L2K | 3.68E+05 | 2.66E−03 | 7.22E−09 | 4.3 |

NB: No binding detected

As shown in Table 11, all of the derived anti-CD3×anti-PSMA bispecific antibodies maintained very weak binding to soluble CD3 in the surface plasmon resonance binding assay, e.g. having a K$_D$ value greater than 11 nM up to 334 nM which is weaker than that of the bispecific anti-CD3 arm derived from germline frameworks, CD3-VH-G.

Several bispecific antibodies exhibited greater than 50 nM K$_D$ values, and some were greater than 100 nM (>1×10$^{-7}$) K$_D$ values (i.e. BSPSMA/CD3-900, BSPSMA/CD3-1000, BSPSMA/CD3-1900), greater than 300 nM (>3×10$^{-7}$) K$_D$ values (i.e. BSPSMA/CD3-005) and even beyond the detection limit of the assay (>500 nM; >5×10$^{-7}$), i.e. showed no detectable binding to soluble human CD3 (i.e. BSPSMA/CD3-200, BSPSMA/CD3-300, BSPSMA/CD3-400, BSPSMA/CD3-004 and BSPSMA/CD3-1800).

Example 6: T Cell Activation and Tumor-specific Cytotoxicity Exhibited by Bispecific Antibodies of the Invention as Measured In Vitro In this example, the specific killing of PSMA, EGFRvlll or MUC16-expressing TAA target cells in the presence of CD3-based bispecific antibodies was monitored via flow cytometry. As reported previously, the bispecific antibodies displayed a range of affinity to CD3 protein and CD3-expressing cell lines (i.e. weak, moderate and strong binding). This same panel of bispecific antibodies was tested for the ability to induce naïve human T-cells to re-direct killing toward target-expressing cells.

Briefly, PSMA-expressing (C4-2, 22Rv1 and TRAMPC2_PSMA), EGFRVIII-expressing (U87/EGFRvIII) or MUC16-expressing (OVCAR3) cell lines were labeled with 1 µM of the fluorescent tracking dye CELL TRACKER VIOLET™. After labeling, cells were plated overnight at 37° C. Separately, human PBMCs were plated in supplemented RPMI media at 1×10$^6$ cells/mL and incubated overnight at 37° C. in order to enrich for lymphocytes by depleting adherent macrophages, dendritic cells, and some monocytes. The next day, target cells were co-incubated with adherent cell-depleted naïve PBMC (Effector/Target cell 4:1 ratio) and a serial dilution of relevant bispecific antibodies or Isotype control (concentration range: 66.7 nM to 0.25 pM) for 48 hours at 37° C. Cells were removed from cell culture plates using an enzyme-free cell dissociation buffer, and analyzed by FACS.

For FACS analysis, cells were stained with a LIVE/DEADIMdead/live far red cell tracker (Invitrogen). 5×10$^5$ counting beads were added to each well immediately before FACS analysis. 1×104 beads were collected for each sample. For the assessment of specificity of killing, cells were gated on live Violet labeled populations. Percent of live population was recorded and used for the calculation of normalized survival.

T cell activation was assessed by incubating cells with directly conjugated antibodies to CD2 and CD69, and by reporting the percent of activated (CD69+) T cells out of total T cells (CD2+).

As the results in Tables 12A-12C show, depletion of TAA-expressing cells was observed with anti-PSMA, EGFRvlll or MUC16×CD3 bispecifics. Most of the tested bispecific antibodies activated and directed human T cells to deplete the target cells with ECsos in picomolar range. Additionally, the observed target-cell lysis (depletion) was associated with an up-regulation of CD69 cells on CD2+T cells, with picomolar (pM) EC$_{50}$S.

Importantly, the results of this example demonstrate that several bispecifics which utilized a CD3 binding arm that displayed weak-to-non-observable binding to CD3 protein or CD3-expressing cells (i.e. CD3-VH-G5) still retained the ability to activate T-cells and exhibited potent cytotoxicity of tumor antigen-expressing cells.

TABLE 12A

Cytotoxicity and T-cell activation properties of selected PSMAxCD3 Bispecific Antibodies

| Bispecific Antibody Identifier | Anti-CD3 Binding Arm | C4-2 Cell depletion EC$_{50}$ [M] | 22RV1 Cell depletion EC$_{50}$ [M] | TrampC2. PSMA Cell depletion EC$_{50}$ [M] | T cell activation EC$_{50}$ [M] |
|---|---|---|---|---|---|
| BSPSMA/ CD3-003 | CD3-VH-G | 1.03E−11 | NT | 6.43E−12 | 1.23E−12 |
| BSPSMA/ CD3-200 | CD3-VH-G2 | NT | No activity | NT | No activity |
| BSPSMA/ CD3-300 | CD3-VH-G3 | NT | Very weak | NT | 1.85E−11 |
| BSPSMA/ CD3-400 | CD3-VH-G4 | NT | Very weak | NT | Very weak |
| BSPSMA/ CD3-004 | CD3-VH-G5 | 2.15E−11 | 6.31E−12 | 1.15E−11 | 1.34E−11 |
| BSPSMA/ CD3-800 | CD3-VH-G8 | NT | NT | 9.27E−12 | 1.76E−12 |
| BSPSMA/ CD3-900 | CD3-VH-G9 | NT | NT | 3.50E−12 | 1.12E−12 |
| BSPSMA/ CD3-1000 | CD3-VH-G10 | NT | NT | 5.97E−12 | 1.28E−12 |
| BSPSMA/ CD3-1100 | CD3-VH-G11 | NT | NT | 3.86E−12 | 1.11E−12 |
| BSPSMA/ CD3-1300 | CD3-VH-G13 | 8.74E−12 | NT | NT | 2.31E−12 |
| BSPSMA/ CD3-1700 | CD3-VH-G17 | 7.37E−12 | 2.07E−12 | NT | 3.89E−12 |

TABLE 12A-continued

Cytotoxicity and T-cell activation properties of selected
PSMAxCD3 Bispecific Antibodies

| Bispecific Antibody Identifier | Anti-CD3 Binding Arm | C4-2 Cell depletion EC$_{50}$ [M] | 22RV1 Cell depletion EC$_{50}$ [M] | TrampC2. PSMA Cell depletion EC$_{50}$ [M] | T cell activation EC$_{50}$ [M] |
|---|---|---|---|---|---|
| BSPSMA/ CD3-005 | CD3-VH-G20 | 1.39E–11 | 8.32E–12 | NT | 6.11E–12 |

NT = not tested

TABLE 12B

Cytotoxicity and T-cell activation properties of selected
EGFRvIIIxCD3 Bispecific Antibodies

| Bispecific Antibody Identifier | Anti-CD3 Binding Arm | U87_EGFRvIII cell depletion EC$_{50}$ [M] | T cell activation EC$_{50}$ [M] |
|---|---|---|---|
| BSV3/CD3-001 | CD3-VH-G | 3.64E–10 | 3.33E–11 |
| BSV3/CD3-002 | CD3-VH-G5 | 1.30E–09 | 1.13E–10 |

TABLE 12C

Cytotoxicity and T-cell activation properties of selected
MUC16xCD3 Bispecific Antibodies

| Bispecific Antibody Identifier | Anti-CD3 Binding Arm | OVCAR3 cell depletion EC$_{50}$ [M] | T cell activation EC$_{50}$ [M] |
|---|---|---|---|
| BSV3/CD3-001 | CD3-VH-G | 2.24E–11 | 5.88E–12 |
| BSV3/CD3-002 | CD3-VH-G5 | 3.06E–11 | 1.01E–11 |

Example 7: Anti-PSMA/Anti-CD3 Bispecific Antibodies Display Potent Anti-Tumor Efficacy In Vivo To determine the in vivo efficacy of exemplary anti-PSMA/anti-CD3 bispecific antibodies identified as having weak or no detectable binding affinity to human and cynomolgus CD3, studies were performed in immunocompromised mice bearing human prostate cancer xenografts. Additional studies were also carried out in immunocompetent mice bearing mouse prostate cancer xenografts engineered to express human PSMA.

Efficacy of anti-PSMA/anti-CD3 bispecific antibodies in human tumor xenograft Models To assess the in vivo efficacy of the anti-PSMA/anti-CD3 bispecifics in human tumor xenograft studies, NOD scid gamma (NSG) mice (Jackson Laboratories, Bar Harbor, Maine) were co-implanted with human peripheral blood mononuclear cells (PBMCs) along with 22Rv1 or C4-2 human prostate tumor cells which endogenously express PSMA.

Briefly, 4×10$^6$ 22Rv1 or 5×10$^6$ C4-2 cells (MD Anderson, TX) cells were co-implanted s.c. with 1×10$^6$ human PBMCs (ReachBio, LLC., Seattle, WA) in a 50:50 mix of MATRIGEL™ matrix (BD Biosciences) into the right flank of male NSG mice. In the C4-2 study, mice were treated i.p. on days 0, 4, and 7 post tumor implantation with 0.1 mg/kg BSPSMA/CD3-003 or BSPSMA/CD3-005.

In an additional xenogenic model, anti-PSMA/anti-CD3 bispecifics were tested in mice engrafted with human hematopoietic CD34+ stem cells. Briefly, newborn SIRPa BALB/ c-Rag2-IL2rγ-(BRG) pups were engrafted with hCD34+ fetal liver cells. 3-6 months later hCD34-engrafted SIRPα BRG mice were then implanted with C4-2 cells (5×10$^6$ s.c. in MATRIGEL™). 8 days later, mice were treated with 10 μg of BSPSMA/CD3-004 or an isotype control antibody, followed by 2x/week doses throughout the study.

In all studies, tumor size was measured 2x/week using calipers and tumor volume calculated as Volume=(length× width$^2$)/2.

As the results in Table 13 show, the bispecific antibodies tested in the xenogenic models described above were all effective at suppressing tumor growth compared to treatment with the isotype control.

TABLE 13

Suppression of Tumor Growth by Administering Anti-PSMA/Anti-CD3
Bispecific Antibodies to Xenogenic Mouse Models
Xenogenic model: suppression of tumor growth

| Tumor Model/ Mouse Strain | N # mice/ treatment group | Bispecific Antibody Identifier | Dose | Final Tumor Volume (mm$^3$) Mean ± SD |
|---|---|---|---|---|
| C4-/2 NSG | 5 | BSPSMA/ CD3-003 | 0.1 mg/kg on day | 0 ± 0 |
| | 5 | BSPSMA/ CD3-005 | 0, 4 & 7 | 0 ± 0 |
| | 5 | Isotype Control | | 960 ± 660 |
| C4-2/ SIRPα Balb/ c-Rag2- IL2rγ-BRG engrafted with hCD34+ HSC | 5 | BSPSMA/ CD3-004 | 1.0 μg/ mouse 2x/week | 70 ± 60 |
| | 5 | Isotype Control | | 260 ± 180 |

Efficacy of anti-PSMA/anti-CD3 bispecific antibodies in immune-competent tumor model Additionally, anti-PSMA/anti-CD3 bispecifics were assessed for anti-tumor activity in an immune-competent model (U.S. Provisional Application No. 62/083,653, filed Nov. 24, 2014). Mice humanized for the three chains (8ye) of CD3 were also humanized for PSMA and implanted with a variant murine prostate cancer cell line TRAMP-C2 transfected with human PSMA.

Prior to study initiation, the tumorigenic cell line variant TRAMP-C2_hPSMAv #1 was generated. Briefly, 7.5×106 TRAMP-C2_hPSMA cells were implanted s.c. into the right flank of male mice humanized for CD3 and PSMA. A tumor was excised and cut into 3 mm fragments and subsequently implanted into the right flank of new male humanized mice. A tumor arising from the implanted tumor fragments was then harvested and disaggregated into a single cell suspension. These cells (TRAMP-C2_hPSMAv #1) were then cultured in vitro under G418 selection. 4×106 cells of this variant cell line were then implanted into the right flank of male PSMA/CD3 humanized mice for the bispecific antibody efficacy studies.

Humanized PSMA/CD3 mice implanted with TRAMPC2_hPSMAv #1 were treated with 100 μg or 10 μg of anti-PSMA/anti-CD3 bispecific antibody BSPSMA/CD3-004 or an isotype control 2x/week starting from the day of tumor implantation. Serum cytokine levels 4h post-injection were also examined, as well as spleen T-cell levels. Study was terminated at Day 27.

As the results in Table 14 show, the anti-PSMA/anti-CD3 bispecific molecule tested, BSPSMA/CD3-004, showed efficacy in significantly delaying tumor growth across treatment groups. Minimal cytokine release was observed after administration of BSPSMA/CD3-004, possibly due to the weak binding of the anti-CD3. Both antibodies tested showed anti-tumor efficacy without depleting T cells in the spleen.

luciferase substrate D-luciferin suspended in PBS (150 mg/kg) and imaged under isoflurane anesthesia after 10 min. BLI was performed using the Xenogen IVIS™ system (Perkin Elmer, Hopkinton, MA) and BLI signals were extracted using LIVING IMAGE™ Image software (Xeno-

TABLE 14

Efficacy of anti-PSMA/anti-CD3 Bispecific antibodies in immine-competent syngeneic model

| Tumor Model/ MouseStrain | Bispecific Antibody Identifier | Dose (µg/mouse) 2x/week* | N # mice/ treatment group | Tumor Volume (mm$^3$) at Day 27 (Mean ± SD) | Mean Serum Cytokine Concentrations, (pg/mL) | | | | | Spleen T-cell level %, (mean ± SD)$^#$ | |
|---|---|---|---|---|---|---|---|---|---|---|---|
| | | | | | IFNg | TNFa | IL-2 | IL-12p70 | IL-6 | CD4+ | CD8+ |
| TRAMP-C2/ PSMA$^{Hum/hum}$ CD3$^{Hum}$ | BSPSMA/ CD3-004 | 100 | 4 | 50 ± 60 | 30 | 60 | 60 | 40 | 370 | 8.0 ± 1.0 | 12.0 ± 2.0 |
| | | 10 | 5 | 380 ± 650 | 10 | 50 | 50 | 10 | 330 | 8.0 ± 3.0 | 14.0 ± 4.0 |
| | Isotype Control | 100 | 5 | 1740 ± 560 | 4 | 30 | 30 | 10 | 230 | 5.0 ± 1.0 | 8.0 ± 2.0 |

*Mice were dosed with antibody or isotype control 2x/week starting on the day of tumor implantation
$^#$Measured as the percentage of CD4+ or CD8 cells in spleen out of live mCD45+ cells In summary, the anti-PSMA/anti-CD3 bispecific antibodies of this invention display potent anti-tumor efficacy in both immune-compromised and immune-competent tumor models, despite having low to no detectable binding to CD3 antigen.

Example 8: Anti-MUC16/Anti-CD3 Bispecific Antibodies Display Potent Anti-Tumor Efficacy In Vivo To determine the in vivo efficacy of exemplary anti-MUC16/anti-CD3 bispecific antibodies identified as having weak or no detectable binding affinity to human and cyno-molgus CD3, studies were performed in immunocompro-mised mice bearing human prostate cancer xenografts. The efficacy of selected bispecific antibodies was tested in both immediate treatment and therapeutic treatment dosing mod-els.

Efficacy of anti-MUC16/anti-CD3 bispecific antibodies in human tumor xenograft models To assess the in vivo efficacy of the anti-MUC16/anti-CD3 bispecifics in human tumor xenograft studies, NOD scid gamma (NSG) mice (Jackson Laboratories, Bar Harbor, Maine) were pre-implanted with human peripheral blood mononuclear cells (PBMCs; ReachBio LLC., Seattle, WA) and then given ascites cells from the human ovarian cancer cell line OVCAR-3 (American Type Tissue Culture, Manas-sas, VA) transduced with luciferase (OVCAR-3/Luc). OVCAR-3 cells endogenously express MUC-16.

Briefly, NSG mice were injected intraperitoneally (i.p.) with $5.0 \times 10^6$ human PBMCs. 8d later, $1.5 \times 10^6$ ascites cells from the OVCAR-3/Luc cell line, previously passaged in vivo, were administered i.p. to the NSG mice engrafted with PBMCs. In the immediate treatment group, mice were treated i.p. on the day of OVCAR-3/Luc cell implantation with MUC16/CD3 Bispecific antibodies BSMUC16/CD3-001 or BSMUC16/CD3-005, or an isotype control, at a dose of 10 µg/mouse (N=5 mice/treatment group). In the thera-peutic dose model, mice were treated i.p. 7d post tumor implantation with the MUC16/CD3 Bispecific or control antibodies described above, at a dose of 10 µg/mouse (N=5/treatment group).

In all studies, tumor growth was monitored via biolumi-nescent imaging (BLI). Mice were injected i.p. with the gen/Perkin Elmer). Regions of interest were drawn around each cell mass and photon intensities were recorded as photons (p)/see(s)/cm$^2$/steradian (sr). For the immediate-treatment group, data is shown as BLI levels 26d post tumor implantation (Table 15). For the therapeutic-treatment group, data is shown as fold-change in BLI between day 6 (1 d before treatment) and at study endpoint (26d post tumor implantation; Table 16).

As the results show, both BSMUC16/CD3-001 and BSMUC16/CD3-005 showed similar efficacy in suppressing tumor growth compared to the isotype control when BLI was measured at Day 26 in the immediate dosing model. Both anti-MUC16/anti-CD3 bispecific antibodies also sup-pressed the growth of established tumors when administered 7d post tumor implantation, compared to the control. In summary, the bispecific anti-MUC16/anti-CD3 antibodies of this invention display potent anti-tumor efficacy in several models.

TABLE 15

Efficacy of anti-MUC16/anti-CD3 Bispecific Antibodies in Immune-Compromised Xenograft Model: Immediate Dosing

| Tumor Model/ Mouse Strain/ Dose | Bispecific Antibody Identifier | N | Avg Bioluminescent Radiance (photons/sec/cm$^2$/steradian) Day 26 (mean ± SD) |
|---|---|---|---|
| OVCAR-3/Luc/ | BSMUC16/CD3-001 | 5 | $1.4 \times 10^3 \pm 3.5 \times 10^2$ |
| NSG/ | BSMUC16/CD3-005 | 5 | $1.5 \times 10^3 \pm 9.7 \times 10^2$ |
| 10 ug/mouse | Isotype Control | 5 | $2.0 \times 10^7 \pm 1.0 \times 10^6$ |

TABLE 16

Efficacy of anti-Muc16/anti-CD3 Bispecific Antibodies in Immune-Compromised Xenograft Model: Therapeutic Treatment

| Tumor Model/ Mouse Strain/ Dose | Bispecific Antibody Identifier | N | Fold change in Avg Bioluminescent Radiance [p/s/cm$^2$/sr] at Day 26 relative to Day 6 |
|---|---|---|---|
| OVCAR-3/Luc/ | BSMUC16/CD3-001 | 5 | 2.0 ± 5.0 |
| NSG/ | BSMUC16/CD3-005 | 5 | 0.01 ± 0.02 |
| 10 ug/mouse | Isotype Control | 5 | 21.0 ± 8.0 |

Example 9: Pharmacokinetic Assessment of
anti-MUC16 ×CD3 Bispecific Antibodies

Assessment of the pharmacokinetics of anti-MUC16 ×CD3 bispecific antibodies BSMUC16/CD3-001 and BSMUC16/CD3-005 and an isotype control were conducted in humanized MUC16 ×CD3 mice (mice homozygous for human MUC16 and CD3 expression, MUC16 $^{hu/hu}$ × CD3 $^{hu/hu}$), CD3 humanized mice (mice homozygous for human CD3 expression, CD3 $^{hu/hu}$) and strain-matched (75% C57BL, 25% 129Sv) wild-type (WT) mice. Cohorts contained 4-5 mice per tested antibody and per mouse strain. All mice received a single intra-peritoneal (i.p.) 0.4 mg/kg dose. Blood samples were collected at 3 and 6 hours, 1, 3, 7, 14 and 28 days post dosing. Blood was processed into serum and frozen at –80° C. until analyzed.

Circulating antibody concentrations were determined by total human IgG antibody analysis using the GYROLAB™ XPLORE™ (Gyros, Uppsala, Sweden). Briefly, a biotinylated goat anti-human IgG polyclonal antibody (Jackson ImmunoResearch, West Grove, PA) was captured onto streptavidin coated beads on a GYROLAB™BIOAFFY™ 200 CD (Gyros) in order to capture the human IgG present in the sera. After affinity column capture, bound human IgG antibody in samples was detected with Alexa-647 labeled goat anti-human IgG (Jackson ImmunoResearch). Fluorescent signal on the column allowed for the detection of bound IgG and response units (RU) were read by the instrument. Sample concentrations were determined by interpolation from a standard curve that was fit using a 5-parameter logistic curve fit using the GYROLAB™Evaluator Software.

PK parameters were determined by non-compartmental analysis (NCA) using Phoenix®WinNonlin® software Version 6.3 (Certara, L.P., Princeton, NJ) and an extravascular dosing model. Using the respective mean concentration values for each antibody, all PK parameters including observed maximum concentration in serum ($C_{max}$), estimated half-life observed ($t_{1/2}$), and area under the concentration curve versus time up to the last measureable concentration ($AUC_{last}$) were determined using a linear trapezoidal rule with linear interpolation and uniform weighting Following i.p. administration of antibodies in WT mice, the total IgG concentration-time profiles of BSMUC16/CD3-001, BSMUC16/CD3-005 and the isotype control were all similar, characterized first by a brief drug distribution followed by a single drug elimination phase throughout the remainder of the study. Maximum serum concentrations ($C_{max}$) and calculated drug exposure ($AUC_{last}$) of the three antibodies were comparable (within 1.3-fold of each other). Following i.p. administration of antibodies in CD3$^{hu/hu}$ mice, BSMUC16/CD3-001, BSMUC16/CD3-005 and isotype control had comparable $C_{max}$ concentrations (4.6, 3.6 and 4.1 µg/mL, respectively). BSMUC16/CD3-005 and the isotype control exhibited similar drug elimination curves, while BSMUC16/CD3-001 exhibited steeper drug elimination than both, suggesting that human CD3 target binding drives clearance. Terminal antibody concentration for BSMUC16/CD3-001 was 0.03 µg/mL, which is about 28-fold less than terminal antibody concentrations determined for the isotype control (0.85 µg/mL) and 22-fold less than BSMUC16/CD3-005 (0.66 µg/mL) serum concentrations.

In MUC16 $^{hu/hu}$ ×CD3 $^{hu/hu}$ double-humanized mice, the Muc16×CD3 bispecific and isotype control antibodies had comparable $C_{max}$ concentrations ($C_{max}$ range: 4.5-6.9

µg/mL). Both bispecific antibodies exhibited steeper drug elimination than the isotype control suggesting a target-mediated effect. Terminal antibody concentrations for BSMUC16/CD3-001 and BSMUC16/CD3-005 were about 29-fold and 2.9-fold less, respectively, than terminal antibody concentrations determined for the isotype control (0.86 µg/mL).

A summary of the data for total anti-MUC16 ×CD3 bispecific antibodies and isotype control antibody concentrations are summarized in Table 17. Mean PK parameters are described in Tables 18A and 18B. Mean total antibody concentrations versus time are shown in FIGS. 2A, 2B and 2C. In conclusion, MUC16×CD3 bispecific antibodies exhibited similar $C_{max}$ and drug elimination curves in WT mice, but BSMUC16/CD3-001 displayed steeper elimination rates than BSMUC16/CD3-005 and the isotype control in CD3 single-humanized mice and MUC16/CD3 double humanized mice. Since the bispecific antibodies administered in this PK study are comprised of the same anti-MUC16 binding arm, the results suggest that the strength of binding of the CD3 targeting arm may play a role in drug exposure levels ($AUC_{last}$) and drug elimination rates. Neither BSMUC16/CD3-001 or BSMUC16/CD3-005 bind mouse MUC16 or mouse CD3.

TABLE 17

Mean Concentrations of Total IgG in Serum Following a Single 0.4 mg/kg Intra-peritoneal Injection of BSMUC16/CD3-001, BSMUC16/CD3-005 and Isotype Control Antibodies in WT Mice, Humanized CD3 Mice and Humanized MUC16 × CD3 mice

| | | Total mAb Concentration In Mouse Serum | | | | | |
| --- | --- | --- | --- | --- | --- | --- | --- |
| | | WT | | CD3$^{hu/hu}$ | | MUC16$^{hu/hu}$ × CD3$^{hu/hu}$ | |
| Antibody | Time (d) | Mean (µg/mL) | +/– SD | Mean (µg/mL) | +/– SD | Mean (µg/mL) | +/– SD |
| BSMUC16/ CD3-001 | 0.13 | 5.39 | 0.34 | 4.30 | 0.29 | 6.77 | 1.52 |
| | 0.25 | 5.80 | 0.36 | 4.26 | 1.07 | 6.63 | 1.06 |
| | 1.00 | 4.13 | 0.43 | 2.87 | 0.71 | 4.89 | 0.53 |
| | 3.00 | 3.19 | 0.53 | 1.44 | 0.27 | 2.50 | 0.22 |
| | 7.00 | 2.61 | 0.73 | 0.72 | 0.13 | 1.20 | 0.22 |
| | 14.00 | 1.44 | 0.69 | 0.18 | 0.05 | 0.28 | 0.08 |
| | 21.00 | 0.93 | ND | 0.07 | 0.02 | 0.06 | 0.05 |
| | 28.00 | 0.60 | ND | 0.04 | 0.01 | 0.03 | 0.02 |
| BSMUC16/ CD3-005 | 0.13 | 4.23 | 0.62 | 3.35 | 1.15 | 4.35 | 0.24 |
| | 0.25 | 4.53 | 0.55 | 3.40 | 0.96 | 4.45 | 0.49 |
| | 1.00 | 3.47 | 0.32 | 2.72 | 0.42 | 3.00 | 0.61 |
| | 3.00 | 2.51 | 0.13 | 1.95 | 0.37 | 1.98 | 0.41 |
| | 7.00 | 2.02 | 0.24 | 2.31 | 0.67 | 1.58 | 0.36 |
| | 14.00 | 1.19 | 0.17 | 1.01 | 0.23 | 0.78 | 0.26 |
| | 21.00 | 1.19 | 0.29 | 1.19 | 0.11 | 0.66 | 0.29 |
| | 28.00 | 0.71 | 0.20 | 0.66 | 0.28 | 0.30 | 0.22 |
| Isotype Control | 0.13 | 5.07 | 1.16 | 5.43 | 1.30 | 6.56 | 0.70 |
| | 0.25 | 5.91 | 1.10 | 5.67 | 1.91 | 6.48 | 0.90 |
| | 1.00 | 2.64 | 0.24 | 2.98 | 1.14 | 2.82 | 0.30 |
| | 3.00 | 2.05 | 0.06 | 2.29 | 0.83 | 1.57 | 0.37 |
| | 7.00 | 1.80 | 0.25 | 2.14 | 0.85 | 1.96 | 0.37 |
| | 14.00 | 1.22 | 0.28 | 1.48 | 0.66 | 1.34 | 0.37 |
| | 21.00 | 1.20 | 0.58 | 1.43 | 0.72 | 1.24 | 0.44 |
| | 28.00 | 0.73 | 0.24 | 0.85 | 0.29 | 0.86 | 0.41 |

Time: (h, when noted) = time in hours post single-dose injection;

D = Day of study;

SD = Standard deviation;

ND = Not determined due to exclusion of mice with drug clearing anti-drug titers

TABLE 18A

| | | \multicolumn{3}{c}{WT mice} | | | \multicolumn{3}{c}{$CD3^{hu/hu}$ mice} | | |
| Para-meter | Units | Isotype Control | BSMUC16/CD3-001 | BSMUC16/CD3-005 | Isotype Control | BSMUC16/CD3-001 | BSMUC16/CD3-005 |
|---|---|---|---|---|---|---|---|
| $C_{max}$ | μg/mL | 5 ± 3 | 6 ± 0.4 | 5 ± 0.5 | 4.1 ± 3 | 4.6 ± 0.8 | 3.5 ± 1 |
| $T_{1/2}$ | d | 11 ± 4 | 7 ± 3 | 12 ± 2 | 14 ± 0.5 | 3.9 ± 0.6 | 11 ± 5 |
| $AUC_{last}$ | d · μg/mL | 35 ± 18 | 40 ± 11 | 45 ± 5 | 49 ± 20 | 16 ± 3 | 36 ± 13 |

Summary of Pharmacokinetic Parameters: CD3 $^{hu/hu}$ humanized mice $C_{max}$ = Peak concentration;
AUC = Area under the concentration-time curve;
$AUC_{last}$ = AUC computed from time zero to the time of the last positive concentration;
$T_{1/2}$ = Estimated half-life observed;
d = day

TABLE 18B

Summary of Pharmacokinetic Parameters: MUC16 $^{hu/hu}$ × CD3 $^{hu/hu}$ double-humanized mice

| | | \multicolumn{3}{c}{WT mice} | | | \multicolumn{3}{c}{$MUC16^{hu/hu}$ × $CD3^{hu/hu}$ mice} | | |
| Para-meter | Units | Isotype Control | BSMUC16/CD3-001 | BSMUC16/CD3-005 | Isotype Control | BSMUC16/CD3-001 | BSMUC16/CD3-005 |
|---|---|---|---|---|---|---|---|
| $C_{max}$ | μg/mL | 5 ± 3 | 6 ± 0.4 | 5 ± 0.5 | 6.7 ± 0.7 | 6.9 ± 1 | 4.5 ± 4 |
| $T_{1/2}$ | d | 11 ± 4 | 7 ± 3 | 12 ± 2 | 12.9 ± 4 | 3.3 ± 0.8 | 8.2 ± 4 |
| $AUC_{last}$ | d · μg/mL | 35 ± 18 | 40 ± 11 | 45 ± 5 | 46 ± 10 | 27 ± 3 | 34 ± 11 |

$C_{max}$ = Peak concentration;
AUC = Area under the concentration-time curve;
$AUC_{last}$ = AUC computed from time zero to the time of the last positive concentration;
$T_{1/2}$ = Estimated half-life observed; d = day

Example 10: Anti-STEAP2/Anti-CD3 Bispecific Antibodies Display Potent Anti-Tumor Efficacy In Vivo To determine the in vivo efficacy of exemplary anti-STEAP2/anti-CD3 bispecific antibodies identified as having weak or no detectable binding affinity to human and cynomolgus CD3, studies were performed in immunocompromised mice bearing human prostate cancer xenografts.

To assess the in vivo efficacy of the anti-STEAP2/anti-CD3 bispecifics in human tumor xenograft studies, NOD scid gamma (NSG) mice (Jackson Laboratories, Bar Harbor, Maine) were co-implanted with human peripheral blood mononuclear cells (PBMCs; ReachBio LLC., Seattle, WA) along with human prostate cancer C4-2 cells (MD Anderson Cancer Center, Houston TX) which endogenously express STEAP2.

Briefly, $5.0 \times 10^6$ C4-2 cells were co-implanted subcutaneously (s.c.) with $1.25 \times 10^6$ human PBMCs in a 50:50 mix of MATRIGEL™ matrix (BD Biosciences, San Jose, CA) into the right flank of male NSG mice. Mice were treated intraperitoneally (i.p.) on the day of implantation (immediate treatment model) with anti-STEAP2/anti-CD3 bispecifics BSSTEAP2/CD3-001. BSSTEAP2/CD3-002 or BSSTEAP2/CD3-003, or an isotype control (that dos not bind C4-2 tumor cells), at a dose of 0.1 or 0.01 mg/kg (N=5 mice/group).

Tumor size was measured 2x/week using calipers and tumor volume calculated as Volume=(length×width²)/2. Data is shown as tumor size (mm³) at study endpoint, 46d post-tumor implantation (Table 19).

As the results in Table 19 show, BSSTEAP2/CD3-001, BSSTEAP2/CD3-002 and BSSTEAP2/CD3-003 significantly suppressed tumor growth compared to an isotype control when tumor sizes were measured at study endpoint. Importantly, the anti-STEAP2/anti-CD3 bispecific antibodies were efficacious in inhibiting C4-2 tumor growth even at the lowest dose of 0.1 mg/kg.

TABLE 19

Efficacy of anti-STEAP2/anti-CD3 Bispecific Antibodies in Immune-Compromised Xenograft Model: Immediate Dosing

| Tumor Model/ Mouse Strain | Bispecific Antibody Identifier | Dose (mg/kg) | N | Tumor Size (mm³) 46 d post-tumor implantation (mean + SD) |
|---|---|---|---|---|
| C4-2/NSG | BSSTEAP2/CD3-001 | 0.1 | 5 | 18.0 ± 14.0 |
| | | 0.01 | 5 | 23.0 ± 220 |
| | BSSTEAP2/CD3-002 | 0.1 | 5 | 15.0 ± 12.0 |
| | | 0.01 | 5 | 17.0 ± 8.0 |
| | BSSTEAP2/CD3-003 | 0.1 | 5 | 19.0 ± 12.0 |
| | | 0.01 | 5 | 25.0 ± 21.0 |
| | Control Bispecific | 0.1 | 5 | 1020.0 ± 922.0 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed:

1. An antibody or antigen-binding fragment thereof that binds human CD3, wherein the antibody or antigen-binding fragment comprises a heavy chain variable region (HCVR) comprising the amino acid sequence of SEQ ID NO: 138, and a light chain variable region (LCVR) comprising the amino acid sequence of SEQ ID NO: 162, wherein the antibody or antigen-binding fragment binds a heterodimeric protein comprising human CD3 epsilon and human CD3 delta with a binding dissociation equilibrium constant ($K_D$) of 300 nM to 500 nM, as measured in a surface plasmon resonance assay at 37° C. in an antigen-capture format.

2. The antibody or antigen-binding fragment of claim 1 comprising an antibody.

3. The antibody of claim 2, comprising a human IgG heavy chain constant region.

4. The antibody of claim 3, wherein the heavy chain constant region is human IgG1 or human IgG4 isotype.

5. The antibody of claim 2 comprising a bispecific antibody.

6. An antibody comprising a heavy chain variable region (HCVR) comprising the amino acid sequence of SEQ ID NO: 138 and a light chain variable region (LCVR) comprising the amino acid sequence of SEQ ID NO: 162.

7. The antibody of claim 6, comprising a human IgG heavy chain constant region.

8. The antibody of claim 7, wherein the heavy chain constant region is human IgG1 isotype.

9. The antibody of claim 7, wherein the heavy chain constant region is human IgG4 isotype.

* * * * *

SEQUENCE LISTING

<160> NUMBER OF SEQ ID NOS: 201

<210> SEQ ID NO 1
<211> LENGTH: 372
<212> TYPE: DNA
<213> ORGANISM: Artificial Sequence
<220> FEATURE:
<223> OTHER INFORMATION: synthetic

<400> SEQUENCE: 1

```
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag caagggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagtttta tcattatgga ctggacgtgt ggggacaagg gacaacagtg     360
acagtgagta gc                                                         372
```

<210> SEQ ID NO 2
<211> LENGTH: 124
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
gggtttacat tcgacgatta cagc                                             24
```

<210> SEQ ID NO 4
<211> LENGTH: 8
<212> TYPE: PRT
<213> ORGANISM: Artificial Sequence
<220> FEATURE:
<223> OTHER INFORMATION: synthetic -continued

<400> SEQUENCE: 4

Gly Phe Thr Phe Asp Asp Tyr Ser
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatcatgga actcaggaag caag                                      24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Trp Asn Ser Gly Ser Lys
1               5

<210> SEQ ID NO 7
<211> LENGTH: 51
<212> TYPE: DNA
<213> ORGANISM: Artificial Sequence
<220> FEATURE:
<223> OTHER INFORMATION: synthetic

<400> SEQUENCE: 7
gcaaaatacg gcagtggtta tggcaagttt tatcattatg gactggacgt g         51

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Ala Lys Tyr Gly Ser Gly Tyr Gly Lys Phe Tyr His Tyr Gly Leu Asp
1               5                   10                  15

Val

<210> SEQ ID NO 9
<211> LENGTH: 372
<212> TYPE: DNA
<213> ORGANISM: Artificial Sequence
<220> FEATURE:
<223> OTHER INFORMATION: synthetic

<400> SEQUENCE: 9
gaagtacagt tggtagaatc tggaggagga ctcgtgcaac caggacgatc attgcggttg     60
agttgtgctg ctagtggatt cacattcgac gactatgcta tgcattgggt aagacaggct    120
ccaggaaaag gactcgaatg ggtgtcagga ataagttgga actccggaag cattgggtac    180
gcagattcag tcaaagggcg attcaccata tcccgagata cgctaagaa ctcactttac     240 cttcaaatga actctcttcg agcagaggac actgcacttt attattgcgc taaggacggc    300
tccggttatg gatattttta ttattatgga atggacgtat ggggacaagg cactactgtt    360

-continued accgttagtt cc                                                                                        372

<210> SEQ ID NO 10
<211> LENGTH: 124
<212> TYPE: PRT
<213> ORGANISM: Artificial Sequence
<220> FEATURE:
<223> OTHER INFORMATION: synthetic

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Tyr Phe Tyr Tyr Tyr Gly Met Asp
            100                 105                 110

Val Trp Gly Gln Gly Thr Thr Val Thr Val Ser Ser
        115                 120

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
ggattcacat tcgacgacta tgct                                                                           24

<210> SEQ ID NO 12
<211> LENGTH: 8
<212> TYPE: PRT
<213> ORGANISM: Artificial Sequence
<220> FEATURE:
<223> OTHER INFORMATION: synthetic

<400> SEQUENCE: 12

Gly Phe Thr Phe Asp Asp Tyr Ala
1               5

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ataagttgga actccggaag catt                                                                           24

<210> SEQ ID NO 14
<211> LENGTH: 8
<212> TYPE: PRT
<213> ORGANISM: Artificial Sequence

```
<220> FEATURE:
<223> OTHER INFORMATION: synthetic

<400> SEQUENCE: 14

Ile Ser Trp Asn Ser Gly Ser Ile
1               5

<210> SEQ ID NO 15
<211> LENGTH: 51
<212> TYPE: DNA
<213> ORGANISM: Artificial Sequence
<220> FEATURE:
<223> OTHER INFORMATION: synthetic

<400> SEQUENCE: 15
gctaaggacg gctccggtta tggatatttt tattattatg gaatggacgt a              51

<210> SEQ ID NO 16
<211> LENGTH: 17
<212> TYPE: PRT
<213> ORGANISM: Artificial Sequence
<220> FEATURE:
<223> OTHER INFORMATION: synthetic

<400> SEQUENCE: 16

Ala Lys Asp Gly Ser Gly Tyr Gly Tyr Phe Tyr Tyr Tyr Gly Met Asp
1               5                   10                  15

Val

<210> SEQ ID NO 17
<211> LENGTH: 372
<212> TYPE: DNA
<213> ORGANISM: Artificial Sequence
<220> FEATURE:
<223> OTHER INFORMATION: synthetic

<400> SEQUENCE: 17
gaagtacaac tggtcgaatc tggaggaggt cttgttcaac ctggtcgatc acttcgcctt      60
tcttgtgccg cttctggttt cactttcgac gattatagca tgcattgggt acgacaggct     120
cccggaaaag ggctggaatg ggtgtcagga attagttgga actcaggaag tattggatac     180
gctgattcag tcaaaggacg cttcacaatc tcaagggaca cgctaaaaa ctcactttat      240 ttgcaaatga actctctccg cgctgaagat accgctctct attattgcgc caaagatggg     300
tctggttacg gttattttta ctactatgga atggacgttt ggggccaagg aacaactgtc     360
acagtatcat cc                                                        372

<210> SEQ ID NO 18
<211> LENGTH: 124
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
```

-continued

```
     50              55              60

Lys Gly Arg Phe Thr Ile Ser Arg Asp Asn Ala Lys Asn Ser Leu Tyr
65                  70              75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Tyr Phe Tyr Tyr Tyr Gly Met Asp
            100             105             110

Val Trp Gly Gln Gly Thr Thr Val Thr Val Ser Ser
        115             120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggtttcactt tcgacgatta tagc                                         24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Asp Asp Tyr Ser
1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagttgga actcaggaag tatt                                         24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

```
Ile Ser Trp Asn Ser Gly Ser Ile
1               5
```

<210> SEQ ID NO 23
<211> LENGTH: 51
<212> TYPE: DNA
<213> ORGANISM: Artificial Sequence
<220> FEATURE:
<223> OTHER INFORMATION: synthetic

<400> SEQUENCE: 23
gccaaagatg ggtctggtta cggttatttt tactactatg gaatggacgt t           51

<210> SEQ ID NO 24
<211> LENGTH: 17

```
<212> TYPE: PRT
<213> ORGANISM: Artificial Sequence
<220> FEATURE:
<223> OTHER INFORMATION: synthetic

<400> SEQUENCE: 24

Ala Lys Asp Gly Ser Gly Tyr Gly Tyr Phe Tyr Tyr Tyr Gly Met Asp
1               5                   10                  15

Val

<210> SEQ ID NO 25
<211> LENGTH: 372
<212> TYPE: DNA
<213> ORGANISM: Artificial Sequence
<220> FEATURE:
<223> OTHER INFORMATION: synthetic

<400> SEQUENCE: 25
gaagttcaac ttgtggaaag tggcggagga ttggttcaac caggacgttc attgaggctt      60
tcatgcgcag cttccggatt tacatttgac gattacgcaa tgcactgggt tagacaggca     120
ccaggaaaag gactggagtg ggtgagcggg atttcatgga acagcggcag tatcggttat     180
gcagactcag ttaaaggaag attcaccatc agtagagaca acgcaaaaaa ttcccttat     240 ctccaaatga actctcttag ggccgaagat acagcattgt actactgcgc aaaagacgga     300
tcaggttacg gaaaatttta ctactatggt atggatgtat ggggtcaggg aaccacagta     360
actgtatcaa gc                                                        372

<210> SEQ ID NO 26
<211> LENGTH: 124
<212> TYPE: PRT
<213> ORGANISM: Artificial Sequence
<220> FEATURE:
<223> OTHER INFORMATION: synthetic

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
```
ggatttacat ttgacgatta cgca                                            24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Asp Asp Tyr Ala
1               5

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
atttcatgga acagcggcag tatc                                            24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Ile Ser Trp Asn Ser Gly Ser Ile
1               5

<210> SEQ ID NO 31
<211> LENGTH: 51
<212> TYPE: DNA
<213> ORGANISM: Artificial Sequence
<220> FEATURE:
<223> OTHER INFORMATION: synthetic

<400> SEQUENCE: 31
gcaaaagacg gatcaggtta cggaaaattt tactactatg gtatggatgt a              51

<210> SEQ ID NO 32
<211> LENGTH: 17
<212> TYPE: PRT
<213> ORGANISM: Artificial Sequence
<220> FEATURE:
<223> OTHER INFORMATION: synthetic

<400> SEQUENCE: 32

Ala Lys Asp Gly Ser Gly Tyr Gly Lys Phe Tyr Tyr Tyr Gly Met Asp
1               5                   10                  15

Val

<210> SEQ ID NO 33
<211> LENGTH: 372
<212> TYPE: DNA
<213> ORGANISM: Artificial Sequence
<220> FEATURE:
<223> OTHER INFORMATION: synthetic

<400> SEQUENCE: 33
gaagtgcaac tcgttgaaag cggaggagga ctggtccagc ccggcagatc tctcagattg     60

-continued

```
tcttgcgctg catccggatt tacatttgac gactattcaa tgcactgggt acggcaagcc      120
ccaggtaaag gactcgaatg ggtaagcggc atatcttgga actcaggcag tattggctac      180
gcagattcag taaaaggaag attcactatt tcaagggata tgctaagaa cagtctctac       240 ttgcaaatga atagcttgcg cgcagaagat acagcacttt attattgtgc aaaagatgga      300
agcggttatg ggaaatttta ttattatggt atggatgtat ggggtcaagg tacaacagtt      360
actgtgtcaa gt                                                         372
```

```
<210> SEQ ID NO 34
<211> LENGTH: 124
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

```
<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggatttacat ttgacgacta ttca                                            24
```

```
<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Asp Asp Tyr Ser
1               5
```

```
<210> SEQ ID NO 37
<211> LENGTH: 24
<212> TYPE: DNA
<213> ORGANISM: Artificial Sequence
<220> FEATURE:
<223> OTHER INFORMATION: synthetic
```

-continued

<400> SEQUENCE: 37
atatcttgga actcaggcag tatt                                              24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Trp Asn Ser Gly Ser Ile
1               5

<210> SEQ ID NO 39
<211> LENGTH: 51
<212> TYPE: DNA
<213> ORGANISM: Artificial Sequence
<220> FEATURE:
<223> OTHER INFORMATION: synthetic

<400> SEQUENCE: 39
gcaaaagatg gaagcggtta tgggaaattt tattattatg gtatggatgt a               51

<210> SEQ ID NO 40
<211> LENGTH: 17
<212> TYPE: PRT
<213> ORGANISM: Artificial Sequence
<220> FEATURE:
<223> OTHER INFORMATION: synthetic

<400> SEQUENCE: 40

Ala Lys Asp Gly Ser Gly Tyr Gly Lys Phe Tyr Tyr Tyr Gly Met Asp
1               5                   10                  15

Val

<210> SEQ ID NO 41
<211> LENGTH: 372
<212> TYPE: DNA
<213> ORGANISM: Artificial Sequence
<220> FEATURE:
<223> OTHER INFORMATION: synthetic

<400> SEQUENCE: 41
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag catcggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagttta tcattatgga ctggacgtgt ggggacaagg gacaacagtg      360
acagtgagta gc                                                        372

<210> SEQ ID NO 42
<211> LENGTH: 124
<212> TYPE: PRT
<213> ORGANISM: Artificial Sequence
<220> FEATURE:
<223> OTHER INFORMATION: synthetic

<400> SEQUENCE: 42

-continued

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120
```

```
<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
gggtttacat tcgacgatta cagc                                                24
```

```
<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Asp Asp Tyr Ser
1               5
```

```
<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
atatcatgga actcaggaag catc                                                24
```

```
<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Trp Asn Ser Gly Ser Ile
1               5
```

```
<210> SEQ ID NO 47
<211> LENGTH: 51
<212> TYPE: DNA
<213> ORGANISM: Artificial Sequence
```

-continued

```
<220> FEATURE:
<223> OTHER INFORMATION: synthetic

<400> SEQUENCE: 47
gcaaaatacg gcagtggtta tggcaagttt tatcattatg gactggacgt g          51

<210> SEQ ID NO 48
<211> LENGTH: 17
<212> TYPE: PRT
<213> ORGANISM: Artificial Sequence
<220> FEATURE:
<223> OTHER INFORMATION: synthetic

<400> SEQUENCE: 48

Ala Lys Tyr Gly Ser Gly Tyr Gly Lys Phe Tyr His Tyr Gly Leu Asp
1               5                   10                  15

Val

<210> SEQ ID NO 49
<211> LENGTH: 372
<212> TYPE: DNA
<213> ORGANISM: Artificial Sequence
<220> FEATURE:
<223> OTHER INFORMATION: synthetic

<400> SEQUENCE: 49
gaagtacagc ttgtagaatc cggcggagga ctggtacaac ctggaagaag tcttagactg     60
agttgcgcag ctagtgggtt tacattcgac gattacagca tgcattgggt gaggcaagct    120
cctggtaaag gattggaatg ggttagcggg atatcatgga actcaggaag caagggatac    180
gccgacagcg tgaaaggccg atttacaata tctagggaca cgcaaaaaa ctctctctac    240 cttcaaatga actctcttag ggcagaagac acagcattgt attattgcgc aaaagacggc    300
agtggttatg gcaagtttta tcattatgga ctggacgtgt ggggacaagg gacaacagtg    360
acagtgagta gc                                                       372

<210> SEQ ID NO 50
<211> LENGTH: 124
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ser Met His Trp Val Arg Gln Ala Pro Gly Lys Gly Leu Glu Trp Val
            35                  40                  45

Ser Gly Ile Ser Trp Asn Ser Gly Ser Lys Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr His Tyr Gly Leu Asp
            100                 105                 110

Val Trp Gly Gln Gly Thr Thr Val Thr Val Ser Ser
            115                 120
```

```
<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
gggtttacat tcgacgatta cagc                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Asp Asp Tyr Ser
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatcatgga actcaggaag caag                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Trp Asn Ser Gly Ser Lys
1               5

<210> SEQ ID NO 55
<211> LENGTH: 51
<212> TYPE: DNA
<213> ORGANISM: Artificial Sequence
<220> FEATURE:
<223> OTHER INFORMATION: synthetic

<400> SEQUENCE: 55
gcaaaagacg gcagtggtta tggcaagttt tatcattatg gactggacgt g           51

<210> SEQ ID NO 56
<211> LENGTH: 17
<212> TYPE: PRT
<213> ORGANISM: Artificial Sequence
<220> FEATURE:
<223> OTHER INFORMATION: synthetic

<400> SEQUENCE: 56

Ala Lys Asp Gly Ser Gly Tyr Gly Lys Phe Tyr His Tyr Gly Leu Asp
1               5                   10                  15

Val
```

-continued

```
<210> SEQ ID NO 57
<211> LENGTH: 372
<212> TYPE: DNA
<213> ORGANISM: Artificial Sequence
<220> FEATURE:
<223> OTHER INFORMATION: synthetic

<400> SEQUENCE: 57
gaagtacagc ttgtagaatc cggcggagga ctggtacaac ctggaagaag tcttagactg        60
agttgcgcag ctagtgggtt tacattcgac gattacagca tgcattgggt gaggcaagct       120
cctggtaaag gattggaatg ggttagcggg atatcatgga actcaggaag caagggatac       180
gccgacagcg tgaaaggccg atttacaata tctaggggaca acgcaaaaaa ctctctctac       240
cttcaaatga actctcttag ggcagaagac acagcattgt attattgcgc aaaatacggc       300
agtggttatg gcaagtttta ttattatgga ctggacgtgt ggggacaagg gacaacagtg       360
acagtgagta gc                                                         372

<210> SEQ ID NO 58
<211> LENGTH: 124
<212> TYPE: PRT
<213> ORGANISM: Artificial Sequence
<220> FEATURE:
<223> OTHER INFORMATION: synthetic

<400> SEQUENCE: 58

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120

<210> SEQ ID NO 59
<211> LENGTH: 24
<212> TYPE: DNA
<213> ORGANISM: Artificial Sequence
<220> FEATURE:
<223> OTHER INFORMATION: synthetic

<400> SEQUENCE: 59
gggtttacat tcgacgatta cagc                                             24

<210> SEQ ID NO 60
<211> LENGTH: 8
<212> TYPE: PRT
<213> ORGANISM: Artificial Sequence
<220> FEATURE:
<223> OTHER INFORMATION: synthetic

<400> SEQUENCE: 60
```

-continued

Gly Phe Thr Phe Asp Asp Tyr Ser
1               5

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
atatcatgga actcaggaag caag                                               24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

Ile Ser Trp Asn Ser Gly Ser Lys
1               5

<210> SEQ ID NO 63
<211> LENGTH: 51
<212> TYPE: DNA
<213> ORGANISM: Artificial Sequence
<220> FEATURE:
<223> OTHER INFORMATION: synthetic

<400> SEQUENCE: 63
gcaaaatacg gcagtggtta tggcaagttt tattattatg gactggacgt g               51

<210> SEQ ID NO 64
<211> LENGTH: 17
<212> TYPE: PRT
<213> ORGANISM: Artificial Sequence
<220> FEATURE:
<223> OTHER INFORMATION: synthetic

<400> SEQUENCE: 64

Ala Lys Tyr Gly Ser Gly Tyr Gly Lys Phe Tyr Tyr Tyr Gly Leu Asp
1               5                   10                  15

Val

<210> SEQ ID NO 65
<211> LENGTH: 372
<212> TYPE: DNA
<213> ORGANISM: Artificial Sequence
<220> FEATURE:
<223> OTHER INFORMATION: synthetic

<400> SEQUENCE: 65
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag caagggatac     180
gccgacagcg tgaaaggccg atttacaata tctagggaca cgcaaaaaa ctctctctac      240 cttcaaatga actctcttag ggcagaagac acagcattgt attattgcgc aaaatacggc     300
agtggttatg gcaagtttta tcattatgga atggacgtgt ggggacaagg gacaacagtg     360
acagtgagta gc                                                         372

```
<210> SEQ ID NO 66
<211> LENGTH: 124
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Met Asp
            100                 105                 110

Val Trp Gly Gln Gly Thr Thr Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
gggtttacat tcgacgatta cagc                                          24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Asp Asp Tyr Ser
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atatcatgga actcaggaag caag                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic
```

<400> SEQUENCE: 70

Ile Ser Trp Asn Ser Gly Ser Lys
1               5

<210> SEQ ID NO 71
<211> LENGTH: 51
<212> TYPE: DNA
<213> ORGANISM: Artificial Sequence
<220> FEATURE:
<223> OTHER INFORMATION: synthetic

<400> SEQUENCE: 71
gcaaaatacg gcagtggtta tggcaagttt tatcattatg gaatggacgt g          51

<210> SEQ ID NO 72
<211> LENGTH: 17
<212> TYPE: PRT
<213> ORGANISM: Artificial Sequence
<220> FEATURE:
<223> OTHER INFORMATION: synthetic

<400> SEQUENCE: 72

Ala Lys Tyr Gly Ser Gly Tyr Gly Lys Phe Tyr His Tyr Gly Met Asp
1               5                   10                  15

Val

<210> SEQ ID NO 73
<211> LENGTH: 372
<212> TYPE: DNA
<213> ORGANISM: Artificial Sequence
<220> FEATURE:
<223> OTHER INFORMATION: synthetic

<400> SEQUENCE: 73
gaagtacagc ttgtagaatc cggcggagga ctggtacaac ctggaagaag tcttagactg     60
agttgcgcag ctagtgggtt tacattcgac gattacagca tgcattgggt gaggcaagct    120
cctggtaaag gattggaatg ggttagcggg atatcatgga actcaggaag catcggatac    180
gccgacagcg tgaaaggccg atttacaata tctaggcaca cgcaaaaaa ctctctctac    240 cttcaaatga actctcttag gcagaagac acagcattgt attattgcgc aaaagacggc    300
agtggttatg gcaagtttta tcattatgga ctggacgtgt ggggacaagg dacaacagtg    360
acagtgagta gc                                                       372

<210> SEQ ID NO 74
<211> LENGTH: 124
<212> TYPE: PRT
<213> ORGANISM: Artificial Sequence
<220> FEATURE:
<223> OTHER INFORMATION: synthetic

<400> SEQUENCE: 74

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr

-continued

```
65                    70                    75                    80

Leu Gln Met Asn Ser Leu Arg Ala Glu Asp Thr Ala Leu Tyr Tyr Cys
                85                    90                    95

Ala Lys Asp Gly Ser Gly Tyr Gly Lys Phe Tyr His Tyr Gly Leu Asp
            100                   105                   110

Val Trp Gly Gln Gly Thr Thr Val Thr Val Ser Ser
        115                   120
```

<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75
gggtttacat tcgacgatta cagc                                              24

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Phe Thr Phe Asp Asp Tyr Ser
1               5

<210> SEQ ID NO 77
<211> LENGTH: 24
<212> TYPE: DNA
<213> ORGANISM: Artificial Sequence
<220> FEATURE:
<223> OTHER INFORMATION: synthetic

<400> SEQUENCE: 77
atatcatgga actcaggaag catc                                              24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Ile Ser Trp Asn Ser Gly Ser Ile
1               5

<210> SEQ ID NO 79
<211> LENGTH: 51
<212> TYPE: DNA
<213> ORGANISM: Artificial Sequence
<220> FEATURE:
<223> OTHER INFORMATION: synthetic

<400> SEQUENCE: 79
gcaaaagacg gcagtggtta tggcaagttt tatcattatg gactggacgt g              51

<210> SEQ ID NO 80
<211> LENGTH: 17
<212> TYPE: PRT
<213> ORGANISM: Artificial Sequence
<220> FEATURE:

<223> OTHER INFORMATION: synthetic

<400> SEQUENCE: 80

Ala Lys Asp Gly Ser Gly Tyr Gly Lys Phe Tyr His Tyr Gly Leu Asp
1               5                   10                  15

Val

<210> SEQ ID NO 81
<211> LENGTH: 372
<212> TYPE: DNA
<213> ORGANISM: Artificial Sequence
<220> FEATURE:
<223> OTHER INFORMATION: synthetic

<400> SEQUENCE: 81
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag catcggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagtttta ttattatgga ctggacgtgt ggggacaagg gacaacagtg     360
acagtgagta gc                                                         372

<210> SEQ ID NO 82
<211> LENGTH: 124
<212> TYPE: PRT
<213> ORGANISM: Artificial Sequence
<220> FEATURE:
<223> OTHER INFORMATION: synthetic

<400> SEQUENCE: 82

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
gggtttacat tcgacgatta cagc                                             24

-continued

```
<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Asp Asp Tyr Ser
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
atatcatgga actcaggaag catc                                        24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Trp Asn Ser Gly Ser Ile
1               5

<210> SEQ ID NO 87
<211> LENGTH: 51
<212> TYPE: DNA
<213> ORGANISM: Artificial Sequence
<220> FEATURE:
<223> OTHER INFORMATION: synthetic

<400> SEQUENCE: 87
gcaaaatacg gcagtggtta tggcaagttt tattattatg gactggacgt g          51

<210> SEQ ID NO 88
<211> LENGTH: 17
<212> TYPE: PRT
<213> ORGANISM: Artificial Sequence
<220> FEATURE:
<223> OTHER INFORMATION: synthetic

<400> SEQUENCE: 88

Ala Lys Tyr Gly Ser Gly Tyr Gly Lys Phe Tyr Tyr Tyr Gly Leu Asp
1               5                   10                  15

Val

<210> SEQ ID NO 89
<211> LENGTH: 372
<212> TYPE: DNA
<213> ORGANISM: Artificial Sequence
<220> FEATURE:
<223> OTHER INFORMATION: synthetic

<400> SEQUENCE: 89
gaagtacagc ttgtagaatc cggcggagga ctggtacaac ctggaagaag tcttagactg    60
agttgcgcag ctagtgggtt tacattcgac gattacagca tgcattgggt gaggcaagct   120
```
cctggtaaag gattggaatg ggttagcggg atatcatgga actcaggaag catcggatac      180
gccgacagcg tgaaaggccg atttacaata tctagggaca acgcaaaaaa ctctctctac      240
cttcaaatga actctcttag ggcagaagac acagcattgt attattgcgc aaaatacggc      300
agtggttatg gcaagtttta tcattatgga atggacgtgt ggggacaagg gacaacagtg      360
acagtgagta gc                                                          372

<210> SEQ ID NO 90
<211> LENGTH: 124
<212> TYPE: PRT
<213> ORGANISM: Artificial Sequence
<220> FEATURE:
<223> OTHER INFORMATION: synthetic

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Met Asp
            100                 105                 110

Val Trp Gly Gln Gly Thr Thr Val Thr Val Ser Ser
        115                 120

<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
gggtttacat tcgacgatta cagc                                             24

<210> SEQ ID NO 92
<211> LENGTH: 8
<212> TYPE: PRT
<213> ORGANISM: Artificial Sequence
<220> FEATURE:
<223> OTHER INFORMATION: synthetic

<400> SEQUENCE: 92

Gly Phe Thr Phe Asp Asp Tyr Ser
1               5

<210> SEQ ID NO 93
<211> LENGTH: 24
<212> TYPE: DNA
<213> ORGANISM: Artificial Sequence
<220> FEATURE:
<223> OTHER INFORMATION: synthetic

<400> SEQUENCE: 93

```
atatcatgga actcaggaag catc                                               24

<210> SEQ ID NO 94
<211> LENGTH: 8
<212> TYPE: PRT
<213> ORGANISM: Artificial Sequence
<220> FEATURE:
<223> OTHER INFORMATION: synthetic

<400> SEQUENCE: 94

Ile Ser Trp Asn Ser Gly Ser Ile
1               5

<210> SEQ ID NO 95
<211> LENGTH: 51
<212> TYPE: DNA
<213> ORGANISM: Artificial Sequence
<220> FEATURE:
<223> OTHER INFORMATION: synthetic

<400> SEQUENCE: 95
gcaaaatacg gcagtggtta tggcaagttt tatcattatg gaatggacgt g              51

<210> SEQ ID NO 96
<211> LENGTH: 17
<212> TYPE: PRT
<213> ORGANISM: Artificial Sequence
<220> FEATURE:
<223> OTHER INFORMATION: synthetic

<400> SEQUENCE: 96

Ala Lys Tyr Gly Ser Gly Tyr Gly Lys Phe Tyr His Tyr Gly Met Asp
1               5                   10                  15

Val

<210> SEQ ID NO 97
<211> LENGTH: 372
<212> TYPE: DNA
<213> ORGANISM: Artificial Sequence
<220> FEATURE:
<223> OTHER INFORMATION: synthetic

<400> SEQUENCE: 97
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattggaatg ggttagcggg atatcatgga actcaggaag caagggatac   180
gccgacagcg tgaaaggccg atttacaata tctagggaca acgcaaaaaa ctctctctac   240
cttcaaatga actctcttag gcagaagac acagcattgt attattgcgc aaaagacggc    300
agtggttatg gcaagtttta ttattatgga ctggacgtgt ggggacaagg gacaacagtg   360
acagtgagta gc                                                       372

<210> SEQ ID NO 98
<211> LENGTH: 124
<212> TYPE: PRT
<213> ORGANISM: Artificial Sequence
<220> FEATURE:
<223> OTHER INFORMATION: synthetic

<400> SEQUENCE: 98

Glu Val Gln Leu Val Glu Ser Gly Gly Gly Leu Val Gln Pro Gly Arg
1               5                   10                  15
```

-continued

Ser Leu Arg Leu Ser Cys Ala Ala Ser Gly Phe Thr Phe Asp Asp Tyr
        20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
gggtttacat tcgacgatta cagc                                                                                              24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Asp Asp Tyr Ser
1                   5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atatcatgga actcaggaag caag                                                                                              24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Trp Asn Ser Gly Ser Lys
1                   5

<210> SEQ ID NO 103
<211> LENGTH: 51
<212> TYPE: DNA
<213> ORGANISM: Artificial Sequence
<220> FEATURE:
<223> OTHER INFORMATION: synthetic -continued

<400> SEQUENCE: 103
gcaaaagacg gcagtggtta tggcaagttt tattattatg gactggacgt g          51

<210> SEQ ID NO 104
<211> LENGTH: 17
<212> TYPE: PRT
<213> ORGANISM: Artificial Sequence
<220> FEATURE:
<223> OTHER INFORMATION: synthetic

<400> SEQUENCE: 104

Ala Lys Asp Gly Ser Gly Tyr Gly Lys Phe Tyr Tyr Tyr Gly Leu Asp
1               5                   10                  15

Val

<210> SEQ ID NO 105
<211> LENGTH: 372
<212> TYPE: DNA
<213> ORGANISM: Artificial Sequence
<220> FEATURE:
<223> OTHER INFORMATION: synthetic

<400> SEQUENCE: 105
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag caagggatac     180
gccgacagcg tgaaaggccg atttacaata tctaggggaca acgcaaaaaa ctctctctac     240
cttcaaatga actctcttag ggcagaagac acagcattgt attattgcgc aaaagacggc     300
agtggttatg gcaagtttta tcattatgga atggacgtgt ggggacaagg gacaacagtg     360
acagtgagta gc                                                        372

<210> SEQ ID NO 106
<211> LENGTH: 124
<212> TYPE: PRT
<213> ORGANISM: Artificial Sequence
<220> FEATURE:
<223> OTHER INFORMATION: synthetic

<400> SEQUENCE: 106

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr His Tyr Gly Met Asp
            100                 105                 110

Val Trp Gly Gln Gly Thr Thr Val Thr Val Ser Ser
        115                 120

<210> SEQ ID NO 107

-continued

```
<211> LENGTH: 24
<212> TYPE: DNA
<213> ORGANISM: Artificial Sequence
<220> FEATURE:
<223> OTHER INFORMATION: synthetic

<400> SEQUENCE: 107
gggtttacat tcgacgatta cagc                                           24

<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108

Gly Phe Thr Phe Asp Asp Tyr Ser
1               5

<210> SEQ ID NO 109
<211> LENGTH: 24
<212> TYPE: DNA
<213> ORGANISM: Artificial Sequence
<220> FEATURE:
<223> OTHER INFORMATION: synthetic

<400> SEQUENCE: 109
atatcatgga actcaggaag caag                                           24

<210> SEQ ID NO 110
<211> LENGTH: 8
<212> TYPE: PRT
<213> ORGANISM: Artificial Sequence
<220> FEATURE:
<223> OTHER INFORMATION: synthetic

<400> SEQUENCE: 110

Ile Ser Trp Asn Ser Gly Ser Lys
1               5

<210> SEQ ID NO 111
<211> LENGTH: 51
<212> TYPE: DNA
<213> ORGANISM: Artificial Sequence
<220> FEATURE:
<223> OTHER INFORMATION: synthetic

<400> SEQUENCE: 111
gcaaaagacg gcagtggtta tggcaagttt tatcattatg gaatggacgt g            51

<210> SEQ ID NO 112
<211> LENGTH: 17
<212> TYPE: PRT
<213> ORGANISM: Artificial Sequence
<220> FEATURE:
<223> OTHER INFORMATION: synthetic

<400> SEQUENCE: 112

Ala Lys Asp Gly Ser Gly Tyr Gly Lys Phe Tyr His Tyr Gly Met Asp
1               5                   10                  15

Val

<210> SEQ ID NO 113
<211> LENGTH: 372
<212> TYPE: DNA
```

-continued

<213> ORGANISM: Artificial Sequence
<220> FEATURE:
<223> OTHER INFORMATION: synthetic

<400> SEQUENCE: 113

```
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag caagggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagtttta ttattatgga atggacgtgt ggggacaagg gacaacagtg     360
acagtgagta gc                                                          372
```

<210> SEQ ID NO 114
<211> LENGTH: 124
<212> TYPE: PRT
<213> ORGANISM: Artificial Sequence
<220> FEATURE:
<223> OTHER INFORMATION: synthetic

<400> SEQUENCE: 114

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115

```
gggtttacat tcgacgatta cagc                                             24
```

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Gly Phe Thr Phe Asp Asp Tyr Ser
1               5
```

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atatcatgga actcaggaag caag                                                        24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Trp Asn Ser Gly Ser Lys
1               5

<210> SEQ ID NO 119
<211> LENGTH: 51
<212> TYPE: DNA
<213> ORGANISM: Artificial Sequence
<220> FEATURE:
<223> OTHER INFORMATION: synthetic

<400> SEQUENCE: 119
gcaaaatacg gcagtggtta tggcaagttt tattattatg gaatggacgt g                          51

<210> SEQ ID NO 120
<211> LENGTH: 17
<212> TYPE: PRT
<213> ORGANISM: Artificial Sequence
<220> FEATURE:
<223> OTHER INFORMATION: synthetic

<400> SEQUENCE: 120

Ala Lys Tyr Gly Ser Gly Tyr Gly Lys Phe Tyr Tyr Tyr Gly Met Asp
1               5                   10                  15

Val

<210> SEQ ID NO 121
<211> LENGTH: 372
<212> TYPE: DNA
<213> ORGANISM: Artificial Sequence
<220> FEATURE:
<223> OTHER INFORMATION: synthetic

<400> SEQUENCE: 121
gaagtacagc ttgtagaatc cggcggagga ctggtacaac ctggaagaag tcttagactg      60
agttgcgcag ctagtgggtt tacattcgac gattacagca tgcattgggt gaggcaagct      120
cctggtaaag gattggaatg ggttagcggg atatcatgga actcaggaag catcggatac      180
gccgacagcg tgaaaggccg atttacaata tctagggaca cgcaaaaaa ctctctctac      240 cttcaaatga actctcttag gcagaagac acagcattgt attattgcgc aaaagacggc      300
agtggttatg gcaagtttta ttattatgga ctggacgtgt ggggacaagg gacaacagtg      360
acagtgagta gc                                                          372

<210> SEQ ID NO 122
<211> LENGTH: 124

-continued

```
<212> TYPE: PRT
<213> ORGANISM: Artificial Sequence
<220> FEATURE:
<223> OTHER INFORMATION: synthetic

<400> SEQUENCE: 122

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Leu Asp
                100                 105                 110

Val Trp Gly Gln Gly Thr Thr Val Thr Val Ser Ser
        115                 120

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
gggtttacat tcgacgatta cagc                                                 24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Phe Thr Phe Asp Asp Tyr Ser
1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atatcatgga actcaggaag catc                                                 24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Ile Ser Trp Asn Ser Gly Ser Ile
```

-continued 1                    5

<210> SEQ ID NO 127
<211> LENGTH: 51
<212> TYPE: DNA
<213> ORGANISM: Artificial Sequence
<220> FEATURE:
<223> OTHER INFORMATION: synthetic

<400> SEQUENCE: 127
gcaaaagacg gcagtggtta tggcaagttt tattattatg gactggacgt g                      51

<210> SEQ ID NO 128
<211> LENGTH: 17
<212> TYPE: PRT
<213> ORGANISM: Artificial Sequence
<220> FEATURE:
<223> OTHER INFORMATION: synthetic

<400> SEQUENCE: 128

Ala Lys Asp Gly Ser Gly Tyr Gly Lys Phe Tyr Tyr Tyr Gly Leu Asp
1                    5                   10                  15

Val

<210> SEQ ID NO 129
<211> LENGTH: 372
<212> TYPE: DNA
<213> ORGANISM: Artificial Sequence
<220> FEATURE:
<223> OTHER INFORMATION: synthetic

<400> SEQUENCE: 129
gaagtacagc ttgtagaatc cggcggagga ctggtacaac ctggaagaag tcttagactg       60
agttgcgcag ctagtgggtt tacattcgac gattacagca tgcattgggt gaggcaagct      120
cctggtaaag gattggaatg ggttagcggg atatcatgga actcaggaag catcggatac      180
gccgacagcg tgaaaggccg atttacaata tctagggaca acgcaaaaaa ctctctctac      240
cttcaaatga actctcttag ggcagaagac acagcattgt attattgcgc aaaagacggc      300
agtggttatg gcaagtttta tcattatgga atggacgtgt ggggacaagg gacaacagtg      360
acagtgagta gc                                                         372

<210> SEQ ID NO 130
<211> LENGTH: 124
<212> TYPE: PRT
<213> ORGANISM: Artificial Sequence
<220> FEATURE:
<223> OTHER INFORMATION: synthetic

<400> SEQUENCE: 130

Glu Val Gln Leu Val Glu Ser Gly Gly Gly Leu Val Gln Pro Gly Arg
1                    5                   10                  15

Ser Leu Arg Leu Ser Cys Ala Ala Ser Gly Phe Thr Phe Asp Asp Tyr
               20                  25                  30

Ser Met His Trp Val Arg Gln Ala Pro Gly Lys Gly Leu Glu Trp Val
           35                  40                  45

Ser Gly Ile Ser Trp Asn Ser Gly Ser Ile Gly Tyr Ala Asp Ser Val
       50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys

-continued

```
                85              90              95

Ala Lys Asp Gly Ser Gly Tyr Gly Lys Phe Tyr His Tyr Gly Met Asp
            100             105             110

Val Trp Gly Gln Gly Thr Thr Val Thr Val Ser Ser
        115             120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
gggtttacat tcgacgatta cagc                                                      24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

```
Gly Phe Thr Phe Asp Asp Tyr Ser
1               5
```

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatcatgga actcaggaag catc                                                      24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

```
Ile Ser Trp Asn Ser Gly Ser Ile
1               5
```

<210> SEQ ID NO 135
<211> LENGTH: 51
<212> TYPE: DNA
<213> ORGANISM: Artificial Sequence
<220> FEATURE:
<223> OTHER INFORMATION: synthetic

<400> SEQUENCE: 135
gcaaaagacg gcagtggtta tggcaagttt tatcattatg gaatggacgt g                        51

<210> SEQ ID NO 136
<211> LENGTH: 17
<212> TYPE: PRT
<213> ORGANISM: Artificial Sequence
<220> FEATURE:
<223> OTHER INFORMATION: synthetic

<400> SEQUENCE: 136

Ala Lys Asp Gly Ser Gly Tyr Gly Lys Phe Tyr His Tyr Gly Met Asp
1               5                   10                  15

Val

<210> SEQ ID NO 137
<211> LENGTH: 372
<212> TYPE: DNA
<213> ORGANISM: Artificial Sequence
<220> FEATURE:
<223> OTHER INFORMATION: synthetic

<400> SEQUENCE: 137
gaagtacagc ttgtagaatc cggcggagga ctggtacaac ctggaagaag tcttagactg       60
agttgcgcag ctagtgggtt tacattcgac gattacagca tgcattgggt gaggcaagct      120
cctggtaaag gattggaatg ggttagcggg atatcatgga actcaggaag catcggatac      180
gccgacagcg tgaaaggccg atttacaata tctaggacga cgcaaaaaa ctctctctac      240 cttcaaatga actctcttag gcagaagac acagcattgt attattgcgc aaaatacggc      300
agtggttatg gcaagtttta ttattatgga atggacgtgt ggggacaagg gacaacagtg      360
acagtgagta gc                                                         372

<210> SEQ ID NO 138
<211> LENGTH: 124
<212> TYPE: PRT
<213> ORGANISM: Artificial Sequence
<220> FEATURE:
<223> OTHER INFORMATION: synthetic

<400> SEQUENCE: 138

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ser Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 139
<211> LENGTH: 24
<212> TYPE: DNA
<213> ORGANISM: Artificial Sequence
<220> FEATURE:
<223> OTHER INFORMATION: synthetic

<400> SEQUENCE: 139
gggtttacat tcgacgatta cagc                                             24

<210> SEQ ID NO 140
<211> LENGTH: 8

```
<212> TYPE: PRT
<213> ORGANISM: Artificial Sequence
<220> FEATURE:
<223> OTHER INFORMATION: synthetic

<400> SEQUENCE: 140

Gly Phe Thr Phe Asp Asp Tyr Ser
1               5

<210> SEQ ID NO 141
<211> LENGTH: 24
<212> TYPE: DNA
<213> ORGANISM: Artificial Sequence
<220> FEATURE:
<223> OTHER INFORMATION: synthetic

<400> SEQUENCE: 141
atatcatgga actcaggaag catc                                              24

<210> SEQ ID NO 142
<211> LENGTH: 8
<212> TYPE: PRT
<213> ORGANISM: Artificial Sequence
<220> FEATURE:
<223> OTHER INFORMATION: synthetic

<400> SEQUENCE: 142

Ile Ser Trp Asn Ser Gly Ser Ile
1               5

<210> SEQ ID NO 143
<211> LENGTH: 51
<212> TYPE: DNA
<213> ORGANISM: Artificial Sequence
<220> FEATURE:
<223> OTHER INFORMATION: synthetic

<400> SEQUENCE: 143
gcaaaatacg gcagtggtta tggcaagttt tattattatg gaatggacgt g               51

<210> SEQ ID NO 144
<211> LENGTH: 17
<212> TYPE: PRT
<213> ORGANISM: Artificial Sequence
<220> FEATURE:
<223> OTHER INFORMATION: synthetic

<400> SEQUENCE: 144

Ala Lys Tyr Gly Ser Gly Tyr Gly Lys Phe Tyr Tyr Tyr Gly Met Asp
1               5                   10                  15

Val

<210> SEQ ID NO 145
<211> LENGTH: 372
<212> TYPE: DNA
<213> ORGANISM: Artificial Sequence
<220> FEATURE:
<223> OTHER INFORMATION: synthetic

<400> SEQUENCE: 145
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattgaatg ggttagcggg atatcatgga actcaggaag caagggatac     180
gccgacagcg tgaaaggccg atttacaata tctagggaca acgcaaaaaa ctctctctac     240
```

-continued

```
cttcaaatga actctcttag ggcagaagac acagcattgt attattgcgc aaaagacggc          300
agtggttatg gcaagtttta ttattatgga atggacgtgt ggggacaagg gacaacagtg          360
acagtgagta gc                                                             372

<210> SEQ ID NO 146
<211> LENGTH: 124
<212> TYPE: PRT
<213> ORGANISM: Artificial Sequence
<220> FEATURE:
<223> OTHER INFORMATION: synthetic

<400> SEQUENCE: 146

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
gggtttacat tcgacgatta cagc                                                 24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Phe Asp Asp Tyr Ser
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atatcatgga actcaggaag caag                                                 24
```

```
<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ser Trp Asn Ser Gly Ser Lys
1               5

<210> SEQ ID NO 151
<211> LENGTH: 51
<212> TYPE: DNA
<213> ORGANISM: Artificial Sequence
<220> FEATURE:
<223> OTHER INFORMATION: synthetic

<400> SEQUENCE: 151
gcaaaagacg gcagtggtta tggcaagttt tattattatg gaatggacgt g          51

<210> SEQ ID NO 152
<211> LENGTH: 17
<212> TYPE: PRT
<213> ORGANISM: Artificial Sequence
<220> FEATURE:
<223> OTHER INFORMATION: synthetic

<400> SEQUENCE: 152

Ala Lys Asp Gly Ser Gly Tyr Gly Lys Phe Tyr Tyr Tyr Gly Met Asp
1               5                   10                  15

Val

<210> SEQ ID NO 153
<211> LENGTH: 372
<212> TYPE: DNA
<213> ORGANISM: Artificial Sequence
<220> FEATURE:
<223> OTHER INFORMATION: synthetic

<400> SEQUENCE: 153
gaagtgcagc tggtggagtc tgggggaggc ttggtacagc ctggcaggtc cctgagactc    60
tcctgtgtag cctctggatt caccttttgat gattattcca tgcactgggt ccggcaagct   120
ccagggaagg gcctggagtg ggtctcaggt attagttgga atagtggtag caaagactat    180
gcggactctg tgaagggccg attcaccatc tccagagaca acgccaagaa ctccctgtat    240
ctgcaaatga acagtctgag agctgaagac acggccttgt attactgtgc aaaatatgga    300
agtggctacg ggaagttcta ccactacggt ttggacgtct ggggccaagg gaccacggtc    360
accgtctcct ca                                                        372

<210> SEQ ID NO 154
<211> LENGTH: 124
<212> TYPE: PRT
<213> ORGANISM: Artificial Sequence
<220> FEATURE:
<223> OTHER INFORMATION: synthetic

<400> SEQUENCE: 154

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30
```

```
Ser Met His Trp Val Arg Gln Ala Pro Gly Lys Gly Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120
```

```
<210> SEQ ID NO 155
<211> LENGTH: 24
<212> TYPE: DNA
<213> ORGANISM: Artificial Sequence
<220> FEATURE:
<223> OTHER INFORMATION: synthetic

<400> SEQUENCE: 155
ggattcacct ttgatgatta ttcc                                          24

<210> SEQ ID NO 156
<211> LENGTH: 8
<212> TYPE: PRT
<213> ORGANISM: Artificial Sequence
<220> FEATURE:
<223> OTHER INFORMATION: synthetic

<400> SEQUENCE: 156

Gly Phe Thr Phe Asp Asp Tyr Ser
1               5

<210> SEQ ID NO 157
<211> LENGTH: 24
<212> TYPE: DNA
<213> ORGANISM: Artificial Sequence
<220> FEATURE:
<223> OTHER INFORMATION: synthetic

<400> SEQUENCE: 157
attagttgga atagtggtag caaa                                          24

<210> SEQ ID NO 158
<211> LENGTH: 8
<212> TYPE: PRT
<213> ORGANISM: Artificial Sequence
<220> FEATURE:
<223> OTHER INFORMATION: synthetic

<400> SEQUENCE: 158

Ile Ser Trp Asn Ser Gly Ser Lys
1               5

<210> SEQ ID NO 159
<211> LENGTH: 51
<212> TYPE: DNA
<213> ORGANISM: Artificial Sequence
<220> FEATURE:
<223> OTHER INFORMATION: synthetic

<400> SEQUENCE: 159
gcaaaatatg gaagtggcta cgggaagttc taccactacg gtttggacgt c            51
```

<210> SEQ ID NO 160
<211> LENGTH: 17
<212> TYPE: PRT
<213> ORGANISM: Artificial Sequence
<220> FEATURE:
<223> OTHER INFORMATION: synthetic

<400> SEQUENCE: 160

Ala Lys Tyr Gly Ser Gly Tyr Gly Lys Phe Tyr His Tyr Gly Leu Asp
1               5                   10                  15

Val

<210> SEQ ID NO 161
<211> LENGTH: 324
<212> TYPE: DNA
<213> ORGANISM: Artificial Sequence
<220> FEATURE:
<223> OTHER INFORMATION: synthetic

<400> SEQUENCE: 161
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaa                                              324

<210> SEQ ID NO 162
<211> LENGTH: 108
<212> TYPE: PRT
<213> ORGANISM: Artificial Sequence
<220> FEATURE:
<223> OTHER INFORMATION: synthetic

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 163
<211> LENGTH: 18
<212> TYPE: DNA
<213> ORGANISM: Artificial Sequence
<220> FEATURE:
<223> OTHER INFORMATION: synthetic

<400> SEQUENCE: 163

-continued

```
cagagcatta gcagctat                                                    18

<210> SEQ ID NO 164
<211> LENGTH: 6
<212> TYPE: PRT
<213> ORGANISM: Artificial Sequence
<220> FEATURE:
<223> OTHER INFORMATION: synthetic

<400> SEQUENCE: 164

Gln Ser Ile Ser Ser Tyr
1               5

<210> SEQ ID NO 165
<211> LENGTH: 9
<212> TYPE: DNA
<213> ORGANISM: Artificial Sequence
<220> FEATURE:
<223> OTHER INFORMATION: synthetic

<400> SEQUENCE: 165 gctgcatcc                                                               9

<210> SEQ ID NO 166
<211> LENGTH: 3
<212> TYPE: PRT
<213> ORGANISM: Artificial Sequence
<220> FEATURE:
<223> OTHER INFORMATION: synthetic

<400> SEQUENCE: 166

Ala Ala Ser
1

<210> SEQ ID NO 167
<211> LENGTH: 30
<212> TYPE: DNA
<213> ORGANISM: Artificial Sequence
<220> FEATURE:
<223> OTHER INFORMATION: synthetic

<400> SEQUENCE: 167
caacagagtt acagtacccc tccgatcacc                                        30

<210> SEQ ID NO 168
<211> LENGTH: 10
<212> TYPE: PRT
<213> ORGANISM: Artificial Sequence
<220> FEATURE:
<223> OTHER INFORMATION: synthetic

<400> SEQUENCE: 168

Gln Gln Ser Tyr Ser Thr Pro Pro Ile Thr
1               5                   10

<210> SEQ ID NO 169
<211> LENGTH: 207
<212> TYPE: PRT
<213> ORGANISM: Artificial Sequence
<220> FEATURE:
<223> OTHER INFORMATION: synthetic

<400> SEQUENCE: 169

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
```

-continued

```
                20                25                30

Gln Thr Pro Tyr Lys Val Ser Ile Ser Gly Thr Thr Val Ile Leu Thr
                35                40                45

Cys Pro Gln Tyr Pro Gly Ser Glu Ile Leu Trp Gln His Asn Asp Lys
        50                55                60

Asn Ile Gly Gly Asp Glu Asp Asp Lys Asn Ile Gly Ser Asp Glu Asp
65                70                75                80

His Leu Ser Leu Lys Glu Phe Ser Glu Leu Glu Gln Ser Gly Tyr Tyr
                85                90                95

Val Cys Tyr Pro Arg Gly Ser Lys Pro Glu Asp Ala Asn Phe Tyr Leu
                100               105               110

Tyr Leu Arg Ala Arg Val Cys Glu Asn Cys Met Glu Met Asp Val Met
            115               120               125

Ser Val Ala Thr Ile Val Ile Val Asp Ile Cys Ile Thr Gly Gly Leu
        130               135               140

Leu Leu Leu Val Tyr Tyr Trp Ser Lys Asn Arg Lys Ala Lys Ala Lys
145               150               155               160

Pro Val Thr Arg Gly Ala Gly Ala Gly Gly Arg Gln Arg Gly Gln Asn
            165               170               175

Lys Glu Arg Pro Pro Pro Val Pro Asn Pro Asp Tyr Glu Pro Ile Arg
            180               185               190

Lys Gly Gln Arg Asp Leu Tyr Ser Gly Leu Asn Gln Arg Arg Ile
            195               200               205
```

```
<210> SEQ ID NO 170
<211> LENGTH: 171
<212> TYPE: PRT
<213> ORGANISM: Artificial Sequence
<220> FEATURE:
<223> OTHER INFORMATION: synthetic

<400> SEQUENCE: 170
```

```
Met Glu His Ser Thr Phe Leu Ser Gly Leu Val Leu Ala Thr Leu Leu
1                5                10                15

Ser Gln Val Ser Pro Phe Lys Ile Pro Ile Glu Glu Leu Glu Asp Arg
            20                25                30

Val Phe Val Asn Cys Asn Thr Ser Ile Thr Trp Val Glu Gly Thr Val
        35                40                45

Gly Thr Leu Leu Ser Asp Ile Thr Arg Leu Asp Leu Gly Lys Arg Ile
        50                55                60

Leu Asp Pro Arg Gly Ile Tyr Arg Cys Asn Gly Thr Asp Ile Tyr Lys
65                70                75                80

Asp Lys Glu Ser Thr Val Gln Val His Tyr Arg Met Cys Gln Ser Cys
                85                90                95

Val Glu Leu Asp Pro Ala Thr Val Ala Gly Ile Ile Val Thr Asp Val
            100               105               110

Ile Ala Thr Leu Leu Leu Ala Leu Gly Val Phe Cys Phe Ala Gly His
        115               120               125

Glu Thr Gly Arg Leu Ser Gly Ala Ala Asp Thr Gln Ala Leu Leu Arg
        130               135               140

Asn Asp Gln Val Tyr Gln Pro Leu Arg Asp Arg Asp Asp Ala Gln Tyr
145               150               155               160

Ser His Leu Gly Gly Asn Trp Ala Arg Asn Lys
            165               170
```

```
<210> SEQ ID NO 171
<211> LENGTH: 750
<212> TYPE: PRT
<213> ORGANISM: Artificial Sequence
<220> FEATURE:
<223> OTHER INFORMATION: synthetic

<400> SEQUENCE: 171

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
```

-continued

```
         370              375              380

Gly Ile Asp Pro Gln Ser Gly Ala Ala Val Val His Glu Ile Val Arg
385              390              395              400

Ser Phe Gly Thr Leu Lys Lys Glu Gly Trp Arg Pro Arg Arg Thr Ile
                 405              410              415

Leu Phe Ala Ser Trp Asp Ala Glu Glu Phe Gly Leu Leu Gly Ser Thr
                 420              425              430

Glu Trp Ala Glu Glu Asn Ser Arg Leu Leu Gln Glu Arg Gly Val Ala
         435              440              445

Tyr Ile Asn Ala Asp Ser Ser Ile Glu Gly Asn Tyr Thr Leu Arg Val
         450              455              460

Asp Cys Thr Pro Leu Met Tyr Ser Leu Val His Asn Leu Thr Lys Glu
465              470              475              480

Leu Lys Ser Pro Asp Glu Gly Phe Glu Gly Lys Ser Leu Tyr Glu Ser
                 485              490              495

Trp Thr Lys Lys Ser Pro Ser Pro Glu Phe Ser Gly Met Pro Arg Ile
                 500              505              510

Ser Lys Leu Gly Ser Gly Asn Asp Phe Glu Val Phe Phe Gln Arg Leu
                 515              520              525

Gly Ile Ala Ser Gly Arg Ala Arg Tyr Thr Lys Asn Trp Glu Thr Asn
         530              535              540

Lys Phe Ser Gly Tyr Pro Leu Tyr His Ser Val Tyr Glu Thr Tyr Glu
545              550              555              560

Leu Val Glu Lys Phe Tyr Asp Pro Met Phe Lys Tyr His Leu Thr Val
                 565              570              575

Ala Gln Val Arg Gly Gly Met Val Phe Glu Leu Ala Asn Ser Ile Val
                 580              585              590

Leu Pro Phe Asp Cys Arg Asp Tyr Ala Val Val Leu Arg Lys Tyr Ala
                 595              600              605

Asp Lys Ile Tyr Ser Ile Ser Met Lys His Pro Gln Glu Met Lys Thr
         610              615              620

Tyr Ser Val Ser Phe Asp Ser Leu Phe Ser Ala Val Lys Asn Phe Thr
625              630              635              640

Glu Ile Ala Ser Lys Phe Ser Glu Arg Leu Gln Asp Phe Asp Lys Ser
                 645              650              655

Asn Pro Ile Val Leu Arg Met Met Asn Asp Gln Leu Met Phe Leu Glu
                 660              665              670

Arg Ala Phe Ile Asp Pro Leu Gly Leu Pro Asp Arg Pro Phe Tyr Arg
                 675              680              685

His Val Ile Tyr Ala Pro Ser Ser His Asn Lys Tyr Ala Gly Glu Ser
         690              695              700

Phe Pro Gly Ile Tyr Asp Ala Leu Phe Asp Ile Glu Ser Lys Val Asp
705              710              715              720

Pro Ser Lys Ala Trp Gly Glu Val Lys Arg Gln Ile Tyr Val Ala Ala
                 725              730              735

Phe Thr Val Gln Ala Ala Ala Glu Thr Leu Ser Glu Val Ala
                 740              745              750
```

<210> SEQ ID NO 172
<211> LENGTH: 943
<212> TYPE: PRT
<213> ORGANISM: Artificial Sequence
<220> FEATURE:
<223> OTHER INFORMATION: synthetic

```
<400> SEQUENCE: 172

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
            35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415
```

```
Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
            435                 440                 445

Lys Val Leu Gly Ser Gly Ala Phe Gly Thr Val Tyr Lys Gly Leu Trp
            450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
            515                 520                 525

Gly Cys Leu Leu Asp Tyr Val Arg Glu His Lys Asp Asn Ile Gly Ser
            530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
                580                 585                 590

Lys Leu Leu Gly Ala Glu Glu Lys Glu Tyr His Ala Glu Gly Gly Lys
            595                 600                 605

Val Pro Ile Lys Trp Met Ala Leu Glu Ser Ile Leu His Arg Ile Tyr
            610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
                660                 665                 670

Thr Ile Asp Val Tyr Met Ile Met Val Lys Cys Trp Met Ile Asp Ala
                675                 680                 685

Asp Ser Arg Pro Lys Phe Arg Glu Leu Ile Ile Glu Phe Ser Lys Met
            690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
            755                 760                 765

Ser Ser Leu Ser Ala Thr Ser Asn Asn Ser Thr Val Ala Cys Ile Asp
770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830
```

-continued

```
Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
    930                 935                 940

<210> SEQ ID NO 173
<211> LENGTH: 14507
<212> TYPE: PRT
<213> ORGANISM: Artificial Sequence
<220> FEATURE:
<223> OTHER INFORMATION: synthetic

<400> SEQUENCE: 173

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
                20                  25                  30

Gly Leu Thr Gly Ala Thr Leu Ser Pro Lys Thr Ser Thr Gly Ala Ile
            35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
        195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255
```

```
Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
            290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
            355                 360                 365

Ala Phe Ala Glu Thr Met Asp Ile Pro Ser Thr His Ile Ala Lys Thr
            370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
            450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
            530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
            595                 600                 605

Ile Ser Met Thr Gly Gly Ser Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
```

```
                675              680              685

Ala Phe Arg Glu Gly Thr Ser Leu Gly Leu Thr Pro Leu Asn Thr Arg
    690              695              700

His Pro Phe Ser Ser Pro Glu Pro Asp Ser Ala Gly His Thr Lys Ile
705              710              715              720

Ser Thr Ser Ile Pro Leu Leu Ser Ser Ala Ser Val Leu Glu Asp Lys
                725              730              735

Val Ser Ala Thr Ser Thr Phe Ser His His Lys Ala Thr Ser Ser Ile
                740              745              750

Thr Thr Gly Thr Pro Glu Ile Ser Thr Lys Thr Lys Pro Ser Ser Ala
                755              760              765

Val Leu Ser Ser Met Thr Leu Ser Asn Ala Ala Thr Ser Pro Glu Arg
    770              775              780

Val Arg Asn Ala Thr Ser Pro Leu Thr His Pro Ser Pro Ser Gly Glu
785              790              795              800

Glu Thr Ala Gly Ser Val Leu Thr Leu Ser Thr Ser Ala Glu Thr Thr
                805              810              815

Asp Ser Pro Asn Ile His Pro Thr Gly Thr Leu Thr Ser Glu Ser Ser
                820              825              830

Glu Ser Pro Ser Thr Leu Ser Leu Pro Ser Val Ser Gly Val Lys Thr
                835              840              845

Thr Phe Ser Ser Ser Thr Pro Ser Thr His Leu Phe Thr Ser Gly Glu
    850              855              860

Glu Thr Glu Glu Thr Ser Asn Pro Ser Val Ser Gln Pro Glu Thr Ser
865              870              875              880

Val Ser Arg Val Arg Thr Thr Leu Ala Ser Thr Ser Val Pro Thr Pro
                885              890              895

Val Phe Pro Thr Met Asp Thr Trp Pro Thr Arg Ser Ala Gln Phe Ser
                900              905              910

Ser Ser His Leu Val Ser Glu Leu Arg Ala Thr Ser Ser Thr Ser Val
                915              920              925

Thr Asn Ser Thr Gly Ser Ala Leu Pro Lys Ile Ser His Leu Thr Gly
    930              935              940

Thr Ala Thr Met Ser Gln Thr Asn Arg Asp Thr Phe Asn Asp Ser Ala
945              950              955              960

Ala Pro Gln Ser Thr Thr Trp Pro Glu Thr Ser Pro Arg Phe Lys Thr
                965              970              975

Gly Leu Pro Ser Ala Thr Thr Thr Val Ser Thr Ser Ala Thr Ser Leu
                980              985              990

Ser Ala Thr Val Met Val Ser Lys Phe Thr Ser Pro Ala Thr Ser Ser
    995              1000              1005

Met Glu Ala Thr Ser Ile Arg Glu Pro Ser Thr Thr Ile Leu Thr
    1010              1015              1020

Thr Glu Thr Thr Asn Gly Pro Gly Ser Met Ala Val Ala Ser Thr
    1025              1030              1035

Asn Ile Pro Ile Gly Lys Gly Tyr Ile Thr Glu Gly Arg Leu Asp
    1040              1045              1050

Thr Ser His Leu Pro Ile Gly Thr Thr Ala Ser Ser Glu Thr Ser
    1055              1060              1065

Met Asp Phe Thr Met Ala Lys Glu Ser Val Ser Met Ser Val Ser
    1070              1075              1080

Pro Ser Gln Ser Met Asp Ala Ala Gly Ser Ser Thr Pro Gly Arg
    1085              1090              1095
```

-continued

```
Thr Ser Gln Phe Val Asp Thr Phe Ser Asp Asp Val Tyr His Leu
    1100             1105             1110

Thr Ser Arg Glu Ile Thr Ile Pro Arg Asp Gly Thr Ser Ser Ala
    1115             1120             1125

Leu Thr Pro Gln Met Thr Ala Thr His Pro Pro Ser Pro Asp Pro
    1130             1135             1140

Gly Ser Ala Arg Ser Thr Trp Leu Gly Ile Leu Ser Ser Ser Pro
    1145             1150             1155

Ser Ser Pro Thr Pro Lys Val Thr Met Ser Ser Thr Phe Ser Thr
    1160             1165             1170

Gln Arg Val Thr Thr Ser Met Ile Met Asp Thr Val Glu Thr Ser
    1175             1180             1185

Arg Trp Asn Met Pro Asn Leu Pro Ser Thr Thr Ser Leu Thr Pro
    1190             1195             1200

Ser Asn Ile Pro Thr Ser Gly Ala Ile Gly Lys Ser Thr Leu Val
    1205             1210             1215

Pro Leu Asp Thr Pro Ser Pro Ala Thr Ser Leu Glu Ala Ser Glu
    1220             1225             1230

Gly Gly Leu Pro Thr Leu Ser Thr Tyr Pro Glu Ser Thr Asn Thr
    1235             1240             1245

Pro Ser Ile His Leu Gly Ala His Ala Ser Ser Glu Ser Pro Ser
    1250             1255             1260

Thr Ile Lys Leu Thr Met Ala Ser Val Val Lys Pro Gly Ser Tyr
    1265             1270             1275

Thr Pro Leu Thr Phe Pro Ser Ile Glu Thr His Ile His Val Ser
    1280             1285             1290

Thr Ala Arg Met Ala Tyr Ser Ser Gly Ser Ser Pro Glu Met Thr
    1295             1300             1305

Ala Pro Gly Glu Thr Asn Thr Gly Ser Thr Trp Asp Pro Thr Thr
    1310             1315             1320

Tyr Ile Thr Thr Thr Asp Pro Lys Asp Thr Ser Ser Ala Gln Val
    1325             1330             1335

Ser Thr Pro His Ser Val Arg Thr Leu Arg Thr Thr Glu Asn His
    1340             1345             1350

Pro Lys Thr Glu Ser Ala Thr Pro Ala Ala Tyr Ser Gly Ser Pro
    1355             1360             1365

Lys Ile Ser Ser Ser Pro Asn Leu Thr Ser Pro Ala Thr Lys Ala
    1370             1375             1380

Trp Thr Ile Thr Asp Thr Thr Glu His Ser Thr Gln Leu His Tyr
    1385             1390             1395

Thr Lys Leu Ala Glu Lys Ser Ser Gly Phe Glu Thr Gln Ser Ala
    1400             1405             1410

Pro Gly Pro Val Ser Val Val Ile Pro Thr Ser Pro Thr Ile Gly
    1415             1420             1425

Ser Ser Thr Leu Glu Leu Thr Ser Asp Val Pro Gly Glu Pro Leu
    1430             1435             1440

Val Leu Ala Pro Ser Glu Gln Thr Thr Ile Thr Leu Pro Met Ala
    1445             1450             1455

Thr Trp Leu Ser Thr Ser Leu Thr Glu Glu Met Ala Ser Thr Asp
    1460             1465             1470

Leu Asp Ile Ser Ser Pro Ser Ser Pro Met Ser Thr Phe Ala Ile
    1475             1480             1485
```

-continued

```
Phe Pro  Pro Met Ser Thr Pro  Ser His Glu Leu Ser  Lys Ser Glu
    1490             1495              1500

Ala Asp  Thr Ser Ala Ile Arg  Asn Thr Asp Ser Thr  Thr Leu Asp
    1505             1510              1515

Gln His  Leu Gly Ile Arg Ser  Leu Gly Arg Thr Gly  Asp Leu Thr
    1520             1525              1530

Thr Val  Pro Ile Thr Pro Leu  Thr Thr Thr Trp Thr  Ser Val Ile
    1535             1540              1545

Glu His  Ser Thr Gln Ala Gln  Asp Thr Leu Ser Ala  Thr Met Ser
    1550             1555              1560

Pro Thr  His Val Thr Gln Ser  Leu Lys Asp Gln Thr  Ser Ile Pro
    1565             1570              1575

Ala Ser  Ala Ser Pro Ser His  Leu Thr Glu Val Tyr  Pro Glu Leu
    1580             1585              1590

Gly Thr  Gln Gly Arg Ser Ser  Ser Glu Ala Thr Thr  Phe Trp Lys
    1595             1600              1605

Pro Ser  Thr Asp Thr Leu Ser  Arg Glu Ile Glu Thr  Gly Pro Thr
    1610             1615              1620

Asn Ile  Gln Ser Thr Pro Pro  Met Asp Asn Thr Thr  Thr Gly Ser
    1625             1630              1635

Ser Ser  Ser Gly Val Thr Leu  Gly Ile Ala His Leu  Pro Ile Gly
    1640             1645              1650

Thr Ser  Ser Pro Ala Glu Thr  Ser Thr Asn Met Ala  Leu Glu Arg
    1655             1660              1665

Arg Ser  Ser Thr Ala Thr Val  Ser Met Ala Gly Thr  Met Gly Leu
    1670             1675              1680

Leu Val  Thr Ser Ala Pro Gly  Arg Ser Ile Ser Gln  Ser Leu Gly
    1685             1690              1695

Arg Val  Ser Ser Val Leu Ser  Glu Ser Thr Thr Glu  Gly Val Thr
    1700             1705              1710

Asp Ser  Ser Lys Gly Ser Ser  Pro Arg Leu Asn Thr  Gln Gly Asn
    1715             1720              1725

Thr Ala  Leu Ser Ser Ser Leu  Glu Pro Ser Tyr Ala  Glu Gly Ser
    1730             1735              1740

Gln Met  Ser Thr Ser Ile Pro  Leu Thr Ser Ser Pro  Thr Thr Pro
    1745             1750              1755

Asp Val  Glu Phe Ile Gly Gly  Ser Thr Phe Trp Thr  Lys Glu Val
    1760             1765              1770

Thr Thr  Val Met Thr Ser Asp  Ile Ser Lys Ser Ser  Ala Arg Thr
    1775             1780              1785

Glu Ser  Ser Ser Ala Thr Leu  Met Ser Thr Ala Leu  Gly Ser Thr
    1790             1795              1800

Glu Asn  Thr Gly Lys Glu Lys  Leu Arg Thr Ala Ser  Met Asp Leu
    1805             1810              1815

Pro Ser  Pro Thr Pro Ser Met  Glu Val Thr Pro Trp  Ile Ser Leu
    1820             1825              1830

Thr Leu  Ser Asn Ala Pro Asn  Thr Thr Asp Ser Leu  Asp Leu Ser
    1835             1840              1845

His Gly  Val His Thr Ser Ser  Ala Gly Thr Leu Ala  Thr Asp Arg
    1850             1855              1860

Ser Leu  Asn Thr Gly Val Thr  Arg Ala Ser Arg Leu  Glu Asn Gly
    1865             1870              1875

Ser Asp  Thr Ser Ser Lys Ser  Leu Ser Met Gly Asn  Ser Thr His
```

-continued

```
              1880                   1885                   1890

Thr  Ser  Met  Thr  Tyr  Thr  Glu   Lys  Ser  Glu  Val  Ser   Ser  Ser  Ile
     1895                   1900                   1905

His  Pro  Arg  Pro  Glu  Thr  Ser   Ala  Pro  Gly  Ala  Glu   Thr  Thr  Leu
     1910                   1915                   1920

Thr  Ser  Thr  Pro  Gly  Asn  Arg   Ala  Ile  Ser  Leu  Thr   Leu  Pro  Phe
     1925                   1930                   1935

Ser  Ser  Ile  Pro  Val  Glu  Glu   Val  Ile  Ser  Thr  Gly   Ile  Thr  Ser
     1940                   1945                   1950

Gly  Pro  Asp  Ile  Asn  Ser  Ala   Pro  Met  Thr  His  Ser   Pro  Ile  Thr
     1955                   1960                   1965

Pro  Pro  Thr  Ile  Val  Trp  Thr   Ser  Thr  Gly  Thr  Ile   Glu  Gln  Ser
     1970                   1975                   1980

Thr  Gln  Pro  Leu  His  Ala  Val   Ser  Ser  Glu  Lys  Val   Ser  Val  Gln
     1985                   1990                   1995

Thr  Gln  Ser  Thr  Pro  Tyr  Val   Asn  Ser  Val  Ala  Val   Ser  Ala  Ser
     2000                   2005                   2010

Pro  Thr  His  Glu  Asn  Ser  Val   Ser  Ser  Gly  Ser  Ser   Thr  Ser  Ser
     2015                   2020                   2025

Pro  Tyr  Ser  Ser  Ala  Ser  Leu   Glu  Ser  Leu  Asp  Ser   Thr  Ile  Ser
     2030                   2035                   2040

Arg  Arg  Asn  Ala  Ile  Thr  Ser   Trp  Leu  Trp  Asp  Leu   Thr  Thr  Ser
     2045                   2050                   2055

Leu  Pro  Thr  Thr  Thr  Trp  Pro   Ser  Thr  Ser  Leu  Ser   Glu  Ala  Leu
     2060                   2065                   2070

Ser  Ser  Gly  His  Ser  Gly  Val   Ser  Asn  Pro  Ser  Ser   Thr  Thr  Thr
     2075                   2080                   2085

Glu  Phe  Pro  Leu  Phe  Ser  Ala   Ala  Ser  Thr  Ser  Ala   Ala  Lys  Gln
     2090                   2095                   2100

Arg  Asn  Pro  Glu  Thr  Glu  Thr   His  Gly  Pro  Gln  Asn   Thr  Ala  Ala
     2105                   2110                   2115

Ser  Thr  Leu  Asn  Thr  Asp  Ala   Ser  Ser  Val  Thr  Gly   Leu  Ser  Glu
     2120                   2125                   2130

Thr  Pro  Val  Gly  Ala  Ser  Ile   Ser  Ser  Glu  Val  Pro   Leu  Pro  Met
     2135                   2140                   2145

Ala  Ile  Thr  Ser  Arg  Ser  Asp   Val  Ser  Gly  Leu  Thr   Ser  Glu  Ser
     2150                   2155                   2160

Thr  Ala  Asn  Pro  Ser  Leu  Gly   Thr  Ala  Ser  Ser  Ala   Gly  Thr  Lys
     2165                   2170                   2175

Leu  Thr  Arg  Thr  Ile  Ser  Leu   Pro  Thr  Ser  Glu  Ser   Leu  Val  Ser
     2180                   2185                   2190

Phe  Arg  Met  Asn  Lys  Asp  Pro   Trp  Thr  Val  Ser  Ile   Pro  Leu  Gly
     2195                   2200                   2205

Ser  His  Pro  Thr  Thr  Asn  Thr   Glu  Thr  Ser  Ile  Pro   Val  Asn  Ser
     2210                   2215                   2220

Ala  Gly  Pro  Pro  Gly  Leu  Ser   Thr  Val  Ala  Ser  Asp   Val  Ile  Asp
     2225                   2230                   2235

Thr  Pro  Ser  Asp  Gly  Ala  Glu   Ser  Ile  Pro  Thr  Val   Ser  Phe  Ser
     2240                   2245                   2250

Pro  Ser  Pro  Asp  Thr  Glu  Val   Thr  Thr  Ile  Ser  His   Phe  Pro  Glu
     2255                   2260                   2265

Lys  Thr  Thr  His  Ser  Phe  Arg   Thr  Ile  Ser  Ser  Leu   Thr  His  Glu
     2270                   2275                   2280
```

```
Leu Thr Ser Arg Val Thr Pro  Ile Pro Gly Asp Trp  Met Ser Ser
    2285                2290                2295

Ala Met Ser Thr Lys Pro Thr  Gly Ala Ser Pro Ser  Ile Thr Leu
    2300                2305                2310

Gly Glu Arg Arg Thr Ile Thr  Ser Ala Ala Pro Thr  Thr Ser Pro
    2315                2320                2325

Ile Val Leu Thr Ala Ser Phe  Thr Glu Thr Ser Thr  Val Ser Leu
    2330                2335                2340

Asp Asn Glu Thr Thr Val Lys  Thr Ser Asp Ile Leu  Asp Ala Arg
    2345                2350                2355

Lys Thr Asn Glu Leu Pro Ser  Asp Ser Ser Ser Ser  Ser Asp Leu
    2360                2365                2370

Ile Asn Thr Ser Ile Ala Ser  Ser Thr Met Asp Val  Thr Lys Thr
    2375                2380                2385

Ala Ser Ile Ser Pro Thr Ser  Ile Ser Gly Met Thr  Ala Ser Ser
    2390                2395                2400

Ser Pro Ser Leu Phe Ser Ser  Asp Arg Pro Gln Val  Pro Thr Ser
    2405                2410                2415

Thr Thr Glu Thr Asn Thr Ala  Thr Ser Pro Ser Val  Ser Ser Asn
    2420                2425                2430

Thr Tyr Ser Leu Asp Gly Gly  Ser Asn Val Gly Gly  Thr Pro Ser
    2435                2440                2445

Thr Leu Pro Pro Phe Thr Ile  Thr His Pro Val Glu  Thr Ser Ser
    2450                2455                2460

Ala Leu Leu Ala Trp Ser Arg  Pro Val Arg Thr Phe  Ser Thr Met
    2465                2470                2475

Val Ser Thr Asp Thr Ala Ser  Gly Glu Asn Pro Thr  Ser Ser Asn
    2480                2485                2490

Ser Val Val Thr Ser Val Pro  Ala Pro Gly Thr Trp  Thr Ser Val
    2495                2500                2505

Gly Ser Thr Thr Asp Leu Pro  Ala Met Gly Phe Leu  Lys Thr Ser
    2510                2515                2520

Pro Ala Gly Glu Ala His Ser  Leu Leu Ala Ser Thr  Ile Glu Pro
    2525                2530                2535

Ala Thr Ala Phe Thr Pro His  Leu Ser Ala Ala Val  Val Thr Gly
    2540                2545                2550

Ser Ser Ala Thr Ser Glu Ala  Ser Leu Leu Thr Thr  Ser Glu Ser
    2555                2560                2565

Lys Ala Ile His Ser Ser Pro  Gln Thr Pro Thr Thr  Pro Thr Ser
    2570                2575                2580

Gly Ala Asn Trp Glu Thr Ser  Ala Thr Pro Glu Ser  Leu Leu Val
    2585                2590                2595

Val Thr Glu Thr Ser Asp Thr  Thr Leu Thr Ser Lys  Ile Leu Val
    2600                2605                2610

Thr Asp Thr Ile Leu Phe Ser  Thr Val Ser Thr Pro  Pro Ser Lys
    2615                2620                2625

Phe Pro Ser Thr Gly Thr Leu  Ser Gly Ala Ser Phe  Pro Thr Leu
    2630                2635                2640

Leu Pro Asp Thr Pro Ala Ile  Pro Leu Thr Ala Thr  Glu Pro Thr
    2645                2650                2655

Ser Ser Leu Ala Thr Ser Phe  Asp Ser Thr Pro Leu  Val Thr Ile
    2660                2665                2670
```

-continued

```
Ala Ser  Asp Ser Leu Gly Thr  Val Pro Glu Thr Thr  Leu Thr Met
    2675                 2680              2685

Ser Glu  Thr Ser Asn Gly Asp  Ala Leu Val Leu Lys  Thr Val Ser
    2690                 2695              2700

Asn Pro  Asp Arg Ser Ile Pro  Gly Ile Thr Ile Gln  Gly Val Thr
    2705                 2710              2715

Glu Ser  Pro Leu His Pro Ser  Ser Thr Ser Pro Ser  Lys Ile Val
    2720                 2725              2730

Ala Pro  Arg Asn Thr Thr Tyr  Glu Gly Ser Ile Thr  Val Ala Leu
    2735                 2740              2745

Ser Thr  Leu Pro Ala Gly Thr  Thr Gly Ser Leu Val  Phe Ser Gln
    2750                 2755              2760

Ser Ser  Glu Asn Ser Glu Thr  Thr Ala Leu Val Asp  Ser Ser Ala
    2765                 2770              2775

Gly Leu  Glu Arg Ala Ser Val  Met Pro Leu Thr Thr  Gly Ser Gln
    2780                 2785              2790

Gly Met  Ala Ser Ser Gly Gly  Ile Arg Ser Gly Ser  Thr His Ser
    2795                 2800              2805

Thr Gly  Thr Lys Thr Phe Ser  Ser Leu Pro Leu Thr  Met Asn Pro
    2810                 2815              2820

Gly Glu  Val Thr Ala Met Ser  Glu Ile Thr Thr Asn  Arg Leu Thr
    2825                 2830              2835

Ala Thr  Gln Ser Thr Ala Pro  Lys Gly Ile Pro Val  Lys Pro Thr
    2840                 2845              2850

Ser Ala  Glu Ser Gly Leu Leu  Thr Pro Val Ser Ala  Ser Ser Ser
    2855                 2860              2865

Pro Ser  Lys Ala Phe Ala Ser  Leu Thr Thr Ala Pro  Pro Thr Trp
    2870                 2875              2880

Gly Ile  Pro Gln Ser Thr Leu  Thr Phe Glu Phe Ser  Glu Val Pro
    2885                 2890              2895

Ser Leu  Asp Thr Lys Ser Ala  Ser Leu Pro Thr Pro  Gly Gln Ser
    2900                 2905              2910

Leu Asn  Thr Ile Pro Asp Ser  Asp Ala Ser Thr Ala  Ser Ser Ser
    2915                 2920              2925

Leu Ser  Lys Ser Pro Glu Lys  Asn Pro Arg Ala Arg  Met Met Thr
    2930                 2935              2940

Ser Thr  Lys Ala Ile Ser Ala  Ser Ser Phe Gln Ser  Thr Gly Phe
    2945                 2950              2955

Thr Glu  Thr Pro Glu Gly Ser  Ala Ser Pro Ser Met  Ala Gly His
    2960                 2965              2970

Glu Pro  Arg Val Pro Thr Ser  Gly Thr Gly Asp Pro  Arg Tyr Ala
    2975                 2980              2985

Ser Glu  Ser Met Ser Tyr Pro  Asp Pro Ser Lys Ala  Ser Ser Ala
    2990                 2995              3000

Met Thr  Ser Thr Ser Leu Ala  Ser Lys Leu Thr Thr  Leu Phe Ser
    3005                 3010              3015

Thr Gly  Gln Ala Ala Arg Ser  Gly Ser Ser Ser Ser  Pro Ile Ser
    3020                 3025              3030

Leu Ser  Thr Glu Lys Glu Thr  Ser Phe Leu Ser Pro  Thr Ala Ser
    3035                 3040              3045

Thr Ser  Arg Lys Thr Ser Leu  Phe Leu Gly Pro Ser  Met Ala Arg
    3050                 3055              3060

Gln Pro  Asn Ile Leu Val His  Leu Gln Thr Ser Ala  Leu Thr Leu
```

```
        3065            3070            3075

Ser Pro Thr Ser Thr Leu Asn Met Ser Gln Glu Glu Pro Pro Glu
    3080            3085            3090

Leu Thr Ser Ser Gln Thr Ile Ala Glu Glu Glu Gly Thr Thr Ala
    3095            3100            3105

Glu Thr Gln Thr Leu Thr Phe Thr Pro Ser Glu Thr Pro Thr Ser
    3110            3115            3120

Leu Leu Pro Val Ser Ser Pro Thr Glu Pro Thr Ala Arg Arg Lys
    3125            3130            3135

Ser Ser Pro Glu Thr Trp Ala Ser Ser Ile Ser Val Pro Ala Lys
    3140            3145            3150

Thr Ser Leu Val Glu Thr Thr Asp Gly Thr Leu Val Thr Thr Ile
    3155            3160            3165

Lys Met Ser Ser Gln Ala Ala Gln Gly Asn Ser Thr Trp Pro Ala
    3170            3175            3180

Pro Ala Glu Glu Thr Gly Ser Ser Pro Ala Gly Thr Ser Pro Gly
    3185            3190            3195

Ser Pro Glu Met Ser Thr Thr Leu Lys Ile Met Ser Ser Lys Glu
    3200            3205            3210

Pro Ser Ile Ser Pro Glu Ile Arg Ser Thr Val Arg Asn Ser Pro
    3215            3220            3225

Trp Lys Thr Pro Glu Thr Thr Val Pro Met Glu Thr Thr Val Glu
    3230            3235            3240

Pro Val Thr Leu Gln Ser Thr Ala Leu Gly Ser Gly Ser Thr Ser
    3245            3250            3255

Ile Ser His Leu Pro Thr Gly Thr Thr Ser Pro Thr Lys Ser Pro
    3260            3265            3270

Thr Glu Asn Met Leu Ala Thr Glu Arg Val Ser Leu Ser Pro Ser
    3275            3280            3285

Pro Pro Glu Ala Trp Thr Asn Leu Tyr Ser Gly Thr Pro Gly Gly
    3290            3295            3300

Thr Arg Gln Ser Leu Ala Thr Met Ser Ser Val Ser Leu Glu Ser
    3305            3310            3315

Pro Thr Ala Arg Ser Ile Thr Gly Thr Gly Gln Gln Ser Ser Pro
    3320            3325            3330

Glu Leu Val Ser Lys Thr Thr Gly Met Glu Phe Ser Met Trp His
    3335            3340            3345

Gly Ser Thr Gly Gly Thr Thr Gly Asp Thr His Val Ser Leu Ser
    3350            3355            3360

Thr Ser Ser Asn Ile Leu Glu Asp Pro Val Thr Ser Pro Asn Ser
    3365            3370            3375

Val Ser Ser Leu Thr Asp Lys Ser Lys His Lys Thr Glu Thr Trp
    3380            3385            3390

Val Ser Thr Thr Ala Ile Pro Ser Thr Val Leu Asn Asn Lys Ile
    3395            3400            3405

Met Ala Ala Glu Gln Gln Thr Ser Arg Ser Val Asp Glu Ala Tyr
    3410            3415            3420

Ser Ser Thr Ser Ser Trp Ser Asp Gln Thr Ser Gly Ser Asp Ile
    3425            3430            3435

Thr Leu Gly Ala Ser Pro Asp Val Thr Asn Thr Leu Tyr Ile Thr
    3440            3445            3450

Ser Thr Ala Gln Thr Thr Ser Leu Val Ser Leu Pro Ser Gly Asp
    3455            3460            3465
```

-continued

```
Gln Gly Ile Thr Ser Leu Thr Asn Pro Ser Gly Gly Lys Thr Ser
    3470                3475            3480

Ser Ala Ser Ser Val Thr Ser Pro Ser Ile Gly Leu Glu Thr Leu
    3485                3490            3495

Arg Ala Asn Val Ser Ala Val Lys Ser Asp Ile Ala Pro Thr Ala
    3500                3505            3510

Gly His Leu Ser Gln Thr Ser Ser Pro Ala Glu Val Ser Ile Leu
    3515                3520            3525

Asp Val Thr Thr Ala Pro Thr Pro Gly Ile Ser Thr Thr Ile Thr
    3530                3535            3540

Thr Met Gly Thr Asn Ser Ile Ser Thr Thr Thr Pro Asn Pro Glu
    3545                3550            3555

Val Gly Met Ser Thr Met Asp Ser Thr Pro Ala Thr Glu Arg Arg
    3560                3565            3570

Thr Thr Ser Thr Glu His Pro Ser Thr Trp Ser Ser Thr Ala Ala
    3575                3580            3585

Ser Asp Ser Trp Thr Val Thr Asp Met Thr Ser Asn Leu Lys Val
    3590                3595            3600

Ala Arg Ser Pro Gly Thr Ile Ser Thr Met His Thr Thr Ser Phe
    3605                3610            3615

Leu Ala Ser Ser Thr Glu Leu Asp Ser Met Ser Thr Pro His Gly
    3620                3625            3630

Arg Ile Thr Val Ile Gly Thr Ser Leu Val Thr Pro Ser Ser Asp
    3635                3640            3645

Ala Ser Ala Val Lys Thr Glu Thr Ser Thr Ser Glu Arg Thr Leu
    3650                3655            3660

Ser Pro Ser Asp Thr Thr Ala Ser Thr Pro Ile Ser Thr Phe Ser
    3665                3670            3675

Arg Val Gln Arg Met Ser Ile Ser Val Pro Asp Ile Leu Ser Thr
    3680                3685            3690

Ser Trp Thr Pro Ser Ser Thr Glu Ala Glu Asp Val Pro Val Ser
    3695                3700            3705

Met Val Ser Thr Asp His Ala Ser Thr Lys Thr Asp Pro Asn Thr
    3710                3715            3720

Pro Leu Ser Thr Phe Leu Phe Asp Ser Leu Ser Thr Leu Asp Trp
    3725                3730            3735

Asp Thr Gly Arg Ser Leu Ser Ser Ala Thr Ala Thr Thr Ser Ala
    3740                3745            3750

Pro Gln Gly Ala Thr Thr Pro Gln Glu Leu Thr Leu Glu Thr Met
    3755                3760            3765

Ile Ser Pro Ala Thr Ser Gln Leu Pro Phe Ser Ile Gly His Ile
    3770                3775            3780

Thr Ser Ala Val Thr Pro Ala Ala Met Ala Arg Ser Ser Gly Val
    3785                3790            3795

Thr Phe Ser Arg Pro Asp Pro Thr Ser Lys Lys Ala Glu Gln Thr
    3800                3805            3810

Ser Thr Gln Leu Pro Thr Thr Thr Ser Ala His Pro Gly Gln Val
    3815                3820            3825

Pro Arg Ser Ala Ala Thr Thr Leu Asp Val Ile Pro His Thr Ala
    3830                3835            3840

Lys Thr Pro Asp Ala Thr Phe Gln Arg Gln Gly Gln Thr Ala Leu
    3845                3850            3855
```

-continued

```
Thr Thr  Glu Ala Arg Ala Thr  Ser Asp Ser Trp Asn  Glu Lys Glu
    3860             3865              3870

Lys Ser  Thr Pro Ser Ala Pro  Trp Ile Thr Glu Met  Met Asn Ser
    3875             3880              3885

Val Ser  Glu Asp Thr Ile Lys  Glu Val Thr Ser Ser  Ser Ser Val
    3890             3895              3900

Leu Arg  Thr Leu Asn Thr Leu  Asp Ile Asn Leu Glu  Ser Gly Thr
    3905             3910              3915

Thr Ser  Ser Pro Ser Trp Lys  Ser Ser Pro Tyr Glu  Arg Ile Ala
    3920             3925              3930

Pro Ser  Glu Ser Thr Thr Asp  Lys Glu Ala Ile His  Pro Ser Thr
    3935             3940              3945

Asn Thr  Val Glu Thr Thr Gly  Trp Val Thr Ser Ser  Glu His Ala
    3950             3955              3960

Ser His  Ser Thr Ile Pro Ala  His Ser Ala Ser Ser  Lys Leu Thr
    3965             3970              3975

Ser Pro  Val Val Thr Thr Ser  Thr Arg Glu Gln Ala  Ile Val Ser
    3980             3985              3990

Met Ser  Thr Thr Thr Trp Pro  Glu Ser Thr Arg Ala  Arg Thr Glu
    3995             4000              4005

Pro Asn  Ser Phe Leu Thr Ile  Glu Leu Arg Asp Val  Ser Pro Tyr
    4010             4015              4020

Met Asp  Thr Ser Ser Thr Thr  Gln Thr Ser Ile Ile  Ser Ser Pro
    4025             4030              4035

Gly Ser  Thr Ala Ile Thr Lys  Gly Pro Arg Thr Glu  Ile Thr Ser
    4040             4045              4050

Ser Lys  Arg Ile Ser Ser Ser  Phe Leu Ala Gln Ser  Met Arg Ser
    4055             4060              4065

Ser Asp  Ser Pro Ser Glu Ala  Ile Thr Arg Leu Ser  Asn Phe Pro
    4070             4075              4080

Ala Met  Thr Glu Ser Gly Gly  Met Ile Leu Ala Met  Gln Thr Ser
    4085             4090              4095

Pro Pro  Gly Ala Thr Ser Leu  Ser Ala Pro Thr Leu  Asp Thr Ser
    4100             4105              4110

Ala Thr  Ala Ser Trp Thr Gly  Thr Pro Leu Ala Thr  Thr Gln Arg
    4115             4120              4125

Phe Thr  Tyr Ser Glu Lys Thr  Thr Leu Phe Ser Lys  Gly Pro Glu
    4130             4135              4140

Asp Thr  Ser Gln Pro Ser Pro  Pro Ser Val Glu Glu  Thr Ser Ser
    4145             4150              4155

Ser Ser  Ser Leu Val Pro Ile  His Ala Thr Thr Ser  Pro Ser Asn
    4160             4165              4170

Ile Leu  Leu Thr Ser Gln Gly  His Ser Pro Ser Ser  Thr Pro Pro
    4175             4180              4185

Val Thr  Ser Val Phe Leu Ser  Glu Thr Ser Gly Leu  Gly Lys Thr
    4190             4195              4200

Thr Asp  Met Ser Arg Ile Ser  Leu Glu Pro Gly Thr  Ser Leu Pro
    4205             4210              4215

Pro Asn  Leu Ser Ser Thr Ala  Gly Glu Ala Leu Ser  Thr Tyr Glu
    4220             4225              4230

Ala Ser  Arg Asp Thr Lys Ala  Ile His His Ser Ala  Asp Thr Ala
    4235             4240              4245

Val Thr  Asn Met Glu Ala Thr  Ser Ser Glu Tyr Ser  Pro Ile Pro
```

-continued

```
        4250              4255              4260

Gly His  Thr Lys Pro Ser Lys  Ala Thr Ser Pro Leu  Val Thr Ser
    4265              4270              4275

His Ile  Met Gly Asp Ile Thr  Ser Ser Thr Ser Val  Phe Gly Ser
    4280              4285              4290

Ser Glu  Thr Thr Glu Ile Glu  Thr Val Ser Ser Val  Asn Gln Gly
    4295              4300              4305

Leu Gln  Glu Arg Ser Thr Ser  Gln Val Ala Ser Ser  Ala Thr Glu
    4310              4315              4320

Thr Ser  Thr Val Ile Thr His  Val Ser Ser Gly Asp  Ala Thr Thr
    4325              4330              4335

His Val  Thr Lys Thr Gln Ala  Thr Phe Ser Ser Gly  Thr Ser Ile
    4340              4345              4350

Ser Ser  Pro His Gln Phe Ile  Thr Ser Thr Asn Thr  Phe Thr Asp
    4355              4360              4365

Val Ser  Thr Asn Pro Ser Thr  Ser Leu Ile Met Thr  Glu Ser Ser
    4370              4375              4380

Gly Val  Thr Ile Thr Thr Gln  Thr Gly Pro Thr Gly  Ala Ala Thr
    4385              4390              4395

Gln Gly  Pro Tyr Leu Leu Asp  Thr Ser Thr Met Pro  Tyr Leu Thr
    4400              4405              4410

Glu Thr  Pro Leu Ala Val Thr  Pro Asp Phe Met Gln  Ser Glu Lys
    4415              4420              4425

Thr Thr  Leu Ile Ser Lys Gly  Pro Lys Asp Val Ser  Trp Thr Ser
    4430              4435              4440

Pro Pro  Ser Val Ala Glu Thr  Ser Tyr Pro Ser Ser  Leu Thr Pro
    4445              4450              4455

Phe Leu  Val Thr Thr Ile Pro  Pro Ala Thr Ser Thr  Leu Gln Gly
    4460              4465              4470

Gln His  Thr Ser Ser Pro Val  Ser Ala Thr Ser Val  Leu Thr Ser
    4475              4480              4485

Gly Leu  Val Lys Thr Thr Asp  Met Leu Asn Thr Ser  Met Glu Pro
    4490              4495              4500

Val Thr  Asn Ser Pro Gln Asn  Leu Asn Asn Pro Ser  Asn Glu Ile
    4505              4510              4515

Leu Ala  Thr Leu Ala Ala Thr  Thr Asp Ile Glu Thr  Ile His Pro
    4520              4525              4530

Ser Ile  Asn Lys Ala Val Thr  Asn Met Gly Thr Ala  Ser Ser Ala
    4535              4540              4545

His Val  Leu His Ser Thr Leu  Pro Val Ser Ser Glu  Pro Ser Thr
    4550              4555              4560

Ala Thr  Ser Pro Met Val Pro  Ala Ser Ser Met Gly  Asp Ala Leu
    4565              4570              4575

Ala Ser  Ile Ser Ile Pro Gly  Ser Glu Thr Thr Asp  Ile Glu Gly
    4580              4585              4590

Glu Pro  Thr Ser Ser Leu Thr  Ala Gly Arg Lys Glu  Asn Ser Thr
    4595              4600              4605

Leu Gln  Glu Met Asn Ser Thr  Thr Glu Ser Asn Ile  Ile Leu Ser
    4610              4615              4620

Asn Val  Ser Val Gly Ala Ile  Thr Glu Ala Thr Lys  Met Glu Val
    4625              4630              4635

Pro Ser  Phe Asp Ala Thr Phe  Ile Pro Thr Pro Ala  Gln Ser Thr
    4640              4645              4650
```

-continued

```
Lys Phe Pro Asp Ile Phe Ser  Val Ala Ser Ser Arg  Leu Ser Asn
4655                4660                4665

Ser Pro Pro Met Thr Ile Ser  Thr His Met Thr Thr  Thr Gln Thr
4670                4675                4680

Gly Ser Ser Gly Ala Thr Ser  Lys Ile Pro Leu Ala  Leu Asp Thr
4685                4690                4695

Ser Thr Leu Glu Thr Ser Ala  Gly Thr Pro Ser Val  Val Thr Glu
4700                4705                4710

Gly Phe Ala His Ser Lys Ile  Thr Thr Ala Met Asn  Asn Asp Val
4715                4720                4725

Lys Asp Val Ser Gln Thr Asn  Pro Pro Phe Gln Asp  Glu Ala Ser
4730                4735                4740

Ser Pro Ser Ser Gln Ala Pro  Val Leu Val Thr Thr  Leu Pro Ser
4745                4750                4755

Ser Val Ala Phe Thr Pro Gln  Trp His Ser Thr Ser  Ser Pro Val
4760                4765                4770

Ser Met Ser Ser Val Leu Thr  Ser Ser Leu Val Lys  Thr Ala Gly
4775                4780                4785

Lys Val Asp Thr Ser Leu Glu  Thr Val Thr Ser Ser  Pro Gln Ser
4790                4795                4800

Met Ser Asn Thr Leu Asp Asp  Ile Ser Val Thr Ser  Ala Ala Thr
4805                4810                4815

Thr Asp Ile Glu Thr Thr His  Pro Ser Ile Asn Thr  Val Val Thr
4820                4825                4830

Asn Val Gly Thr Thr Gly Ser  Ala Phe Glu Ser His  Ser Thr Val
4835                4840                4845

Ser Ala Tyr Pro Glu Pro Ser  Lys Val Thr Ser Pro  Asn Val Thr
4850                4855                4860

Thr Ser Thr Met Glu Asp Thr  Thr Ile Ser Arg Ser  Ile Pro Lys
4865                4870                4875

Ser Ser Lys Thr Thr Arg Thr  Glu Thr Glu Thr Thr  Ser Ser Leu
4880                4885                4890

Thr Pro Lys Leu Arg Glu Thr  Ser Ile Ser Gln Glu  Ile Thr Ser
4895                4900                4905

Ser Thr Glu Thr Ser Thr Val  Pro Tyr Lys Glu Leu  Thr Gly Ala
4910                4915                4920

Thr Thr Glu Val Ser Arg Thr  Asp Val Thr Ser Ser  Ser Ser Thr
4925                4930                4935

Ser Phe Pro Gly Pro Asp Gln  Ser Thr Val Ser Leu  Asp Ile Ser
4940                4945                4950

Thr Glu Thr Asn Thr Arg Leu  Ser Thr Ser Pro Ile  Met Thr Glu
4955                4960                4965

Ser Ala Glu Ile Thr Ile Thr  Thr Gln Thr Gly Pro  His Gly Ala
4970                4975                4980

Thr Ser Gln Asp Thr Phe Thr  Met Asp Pro Ser Asn  Thr Thr Pro
4985                4990                4995

Gln Ala Gly Ile His Ser Ala  Met Thr His Gly Phe  Ser Gln Leu
5000                5005                5010

Asp Val Thr Thr Leu Met Ser  Arg Ile Pro Gln Asp  Val Ser Trp
5015                5020                5025

Thr Ser Pro Pro Ser Val Asp  Lys Thr Ser Ser Pro  Ser Ser Phe
5030                5035                5040
```

```
Leu Ser  Ser Pro Ala Met Thr  Thr Pro Ser Leu Ile  Ser Ser Thr
    5045                5050                 5055

Leu Pro  Glu Asp Lys Leu Ser  Ser Pro Met Thr Ser  Leu Leu Thr
    5060                5065                 5070

Ser Gly  Leu Val Lys Ile Thr  Asp Ile Leu Arg Thr  Arg Leu Glu
    5075                5080                 5085

Pro Val  Thr Ser Ser Leu Pro  Asn Phe Ser Ser Thr  Ser Asp Lys
    5090                5095                 5100

Ile Leu  Ala Thr Ser Lys Asp  Ser Lys Asp Thr Lys  Glu Ile Phe
    5105                5110                 5115

Pro Ser  Ile Asn Thr Glu Glu  Thr Asn Val Lys Ala  Asn Asn Ser
    5120                5125                 5130

Gly His  Glu Ser His Ser Pro  Ala Leu Ala Asp Ser  Glu Thr Pro
    5135                5140                 5145

Lys Ala  Thr Thr Gln Met Val  Ile Thr Thr Thr Val  Gly Asp Pro
    5150                5155                 5160

Ala Pro  Ser Thr Ser Met Pro  Val His Gly Ser Ser  Glu Thr Thr
    5165                5170                 5175

Asn Ile  Lys Arg Glu Pro Thr  Tyr Phe Leu Thr Pro  Arg Leu Arg
    5180                5185                 5190

Glu Thr  Ser Thr Ser Gln Glu  Ser Ser Phe Pro Thr  Asp Thr Ser
    5195                5200                 5205

Phe Leu  Leu Ser Lys Val Pro  Thr Gly Thr Ile Thr  Glu Val Ser
    5210                5215                 5220

Ser Thr  Gly Val Asn Ser Ser  Ser Lys Ile Ser Thr  Pro Asp His
    5225                5230                 5235

Asp Lys  Ser Thr Val Pro Pro  Asp Thr Phe Thr Gly  Glu Ile Pro
    5240                5245                 5250

Arg Val  Phe Thr Ser Ser Ile  Lys Thr Lys Ser Ala  Glu Met Thr
    5255                5260                 5265

Ile Thr  Thr Gln Ala Ser Pro  Pro Glu Ser Ala Ser  His Ser Thr
    5270                5275                 5280

Leu Pro  Leu Asp Thr Ser Thr  Thr Leu Ser Gln Gly  Gly Thr His
    5285                5290                 5295

Ser Thr  Val Thr Gln Gly Phe  Pro Tyr Ser Glu Val  Thr Thr Leu
    5300                5305                 5310

Met Gly  Met Gly Pro Gly Asn  Val Ser Trp Met Thr  Thr Pro Pro
    5315                5320                 5325

Val Glu  Glu Thr Ser Ser Val  Ser Ser Leu Met Ser  Ser Pro Ala
    5330                5335                 5340

Met Thr  Ser Pro Ser Pro Val  Ser Ser Thr Ser Pro  Gln Ser Ile
    5345                5350                 5355

Pro Ser  Ser Pro Leu Pro Val  Thr Ala Leu Pro Thr  Ser Val Leu
    5360                5365                 5370

Val Thr  Thr Thr Asp Val Leu  Gly Thr Thr Ser Pro  Glu Ser Val
    5375                5380                 5385

Thr Ser  Ser Pro Pro Asn Leu  Ser Ser Ile Thr His  Glu Arg Pro
    5390                5395                 5400

Ala Thr  Tyr Lys Asp Thr Ala  His Thr Glu Ala Ala  Met His His
    5405                5410                 5415

Ser Thr  Asn Thr Ala Val Thr  Asn Val Gly Thr Ser  Gly Ser Gly
    5420                5425                 5430

His Lys  Ser Gln Ser Ser Val  Leu Ala Asp Ser Glu  Thr Ser Lys
```

-continued

```
        5435              5440               5445

Ala Thr  Pro Leu Met Ser Thr  Thr Ser Thr Leu Gly  Asp Thr Ser
    5450              5455               5460

Val Ser  Thr Ser Thr Pro Asn  Ile Ser Gln Thr Asn  Gln Ile Gln
    5465              5470               5475

Thr Glu  Pro Thr Ala Ser Leu  Ser Pro Arg Leu Arg  Glu Ser Ser
    5480              5485               5490

Thr Ser  Glu Lys Thr Ser Ser  Thr Thr Glu Thr Asn  Thr Ala Phe
    5495              5500               5505

Ser Tyr  Val Pro Thr Gly Ala  Ile Thr Gln Ala Ser  Arg Thr Glu
    5510              5515               5520

Ile Ser  Ser Ser Arg Thr Ser  Ile Ser Asp Leu Asp  Arg Pro Thr
    5525              5530               5535

Ile Ala  Pro Asp Ile Ser Thr  Gly Met Ile Thr Arg  Leu Phe Thr
    5540              5545               5550

Ser Pro  Ile Met Thr Lys Ser  Ala Glu Met Thr Val  Thr Thr Gln
    5555              5560               5565

Thr Thr  Thr Pro Gly Ala Thr  Ser Gln Gly Ile Leu  Pro Trp Asp
    5570              5575               5580

Thr Ser  Thr Thr Leu Phe Gln  Gly Gly Thr His Ser  Thr Val Ser
    5585              5590               5595

Gln Gly  Phe Pro His Ser Glu  Ile Thr Thr Leu Arg  Ser Arg Thr
    5600              5605               5610

Pro Gly  Asp Val Ser Trp Met  Thr Thr Pro Pro Val  Glu Glu Thr
    5615              5620               5625

Ser Ser  Gly Phe Ser Leu Met  Ser Pro Ser Met Thr  Ser Pro Ser
    5630              5635               5640

Pro Val  Ser Ser Thr Ser Pro  Glu Ser Ile Pro Ser  Ser Pro Leu
    5645              5650               5655

Pro Val  Thr Ala Leu Leu Thr  Ser Val Leu Val Thr  Thr Thr Asn
    5660              5665               5670

Val Leu  Gly Thr Thr Ser Pro  Glu Pro Val Thr Ser  Ser Pro Pro
    5675              5680               5685

Asn Leu  Ser Ser Pro Thr Gln  Glu Arg Leu Thr Thr  Tyr Lys Asp
    5690              5695               5700

Thr Ala  His Thr Glu Ala Met  His Ala Ser Met His  Thr Asn Thr
    5705              5710               5715

Ala Val  Ala Asn Val Gly Thr  Ser Ile Ser Gly His  Glu Ser Gln
    5720              5725               5730

Ser Ser  Val Pro Ala Asp Ser  His Thr Ser Lys Ala  Thr Ser Pro
    5735              5740               5745

Met Gly  Ile Thr Phe Ala Met  Gly Asp Thr Ser Val  Ser Thr Ser
    5750              5755               5760

Thr Pro  Ala Phe Phe Glu Thr  Arg Ile Gln Thr Glu  Ser Thr Ser
    5765              5770               5775

Ser Leu  Ile Pro Gly Leu Arg  Asp Thr Arg Thr Ser  Glu Glu Ile
    5780              5785               5790

Asn Thr  Val Thr Glu Thr Ser  Thr Val Leu Ser Glu  Val Pro Thr
    5795              5800               5805

Thr Thr  Thr Thr Glu Val Ser  Arg Thr Glu Val Ile  Thr Ser Ser
    5810              5815               5820

Arg Thr  Thr Ile Ser Gly Pro  Asp His Ser Lys Met  Ser Pro Tyr
    5825              5830               5835
```

-continued

```
Ile Ser  Thr Glu Thr Ile Thr  Arg Leu Ser Thr Phe  Pro Phe Val
    5840                 5845                5850

Thr Gly  Ser Thr Glu Met Ala  Ile Thr Asn Gln Thr  Gly Pro Ile
    5855                 5860                5865

Gly Thr  Ile Ser Gln Ala Thr  Leu Thr Leu Asp Thr  Ser Ser Thr
    5870                 5875                5880

Ala Ser  Trp Glu Gly Thr His  Ser Pro Val Thr Gln  Arg Phe Pro
    5885                 5890                5895

His Ser  Glu Glu Thr Thr Thr  Met Ser Arg Ser Thr  Lys Gly Val
    5900                 5905                5910

Ser Trp  Gln Ser Pro Pro Ser  Val Glu Glu Thr Ser  Ser Pro Ser
    5915                 5920                5925

Ser Pro  Val Pro Leu Pro Ala  Ile Thr Ser His Ser  Ser Leu Tyr
    5930                 5935                5940

Ser Ala  Val Ser Gly Ser Ser  Pro Thr Ser Ala Leu  Pro Val Thr
    5945                 5950                5955

Ser Leu  Leu Thr Ser Gly Arg  Arg Lys Thr Ile Asp  Met Leu Asp
    5960                 5965                5970

Thr His  Ser Glu Leu Val Thr  Ser Ser Leu Pro Ser  Ala Ser Ser
    5975                 5980                5985

Phe Ser  Gly Glu Ile Leu Thr  Ser Glu Ala Ser Thr  Asn Thr Glu
    5990                 5995                6000

Thr Ile  His Phe Ser Glu Asn  Thr Ala Glu Thr Asn  Met Gly Thr
    6005                 6010                6015

Thr Asn  Ser Met His Lys Leu  His Ser Ser Val Ser  Ile His Ser
    6020                 6025                6030

Gln Pro  Ser Gly His Thr Pro  Pro Lys Val Thr Gly  Ser Met Met
    6035                 6040                6045

Glu Asp  Ala Ile Val Ser Thr  Ser Thr Pro Gly Ser  Pro Glu Thr
    6050                 6055                6060

Lys Asn  Val Asp Arg Asp Ser  Thr Ser Pro Leu Thr  Pro Glu Leu
    6065                 6070                6075

Lys Glu  Asp Ser Thr Ala Leu  Val Met Asn Ser Thr  Thr Glu Ser
    6080                 6085                6090

Asn Thr  Val Phe Ser Ser Val  Ser Leu Asp Ala Ala  Thr Glu Val
    6095                 6100                6105

Ser Arg  Ala Glu Val Thr Tyr  Tyr Asp Pro Thr Phe  Met Pro Ala
    6110                 6115                6120

Ser Ala  Gln Ser Thr Lys Ser  Pro Asp Ile Ser Pro  Glu Ala Ser
    6125                 6130                6135

Ser Ser  His Ser Asn Ser Pro  Pro Leu Thr Ile Ser  Thr His Lys
    6140                 6145                6150

Thr Ile  Ala Thr Gln Thr Gly  Pro Ser Gly Val Thr  Ser Leu Gly
    6155                 6160                6165

Gln Leu  Thr Leu Asp Thr Ser  Thr Ile Ala Thr Ser  Ala Gly Thr
    6170                 6175                6180

Pro Ser  Ala Arg Thr Gln Asp  Phe Val Asp Ser Glu  Thr Thr Ser
    6185                 6190                6195

Val Met  Asn Asn Asp Leu Asn  Asp Val Leu Lys Thr  Ser Pro Phe
    6200                 6205                6210

Ser Ala  Glu Glu Ala Asn Ser  Leu Ser Ser Gln Ala  Pro Leu Leu
    6215                 6220                6225
```

```
Val Thr  Thr Ser Pro Ser Pro  Val Thr Ser Thr Leu  Gln Glu His
    6230              6235                  6240

Ser Thr  Ser Ser Leu Val Ser  Val Thr Ser Val Pro  Thr Pro Thr
    6245              6250                  6255

Leu Ala  Lys Ile Thr Asp Met  Asp Thr Asn Leu Glu  Pro Val Thr
    6260              6265                  6270

Arg Ser  Pro Gln Asn Leu Arg  Asn Thr Leu Ala Thr  Ser Glu Ala
    6275              6280                  6285

Thr Thr  Asp Thr His Thr Met  His Pro Ser Ile Asn  Thr Ala Val
    6290              6295                  6300

Ala Asn  Val Gly Thr Thr Ser  Ser Pro Asn Glu Phe  Tyr Phe Thr
    6305              6310                  6315

Val Ser  Pro Asp Ser Asp Pro  Tyr Lys Ala Thr Ser  Ala Val Val
    6320              6325                  6330

Ile Thr  Ser Thr Ser Gly Asp  Ser Ile Val Ser Thr  Ser Met Pro
    6335              6340                  6345

Arg Ser  Ser Ala Met Lys Lys  Ile Glu Ser Glu Thr  Thr Phe Ser
    6350              6355                  6360

Leu Ile  Phe Arg Leu Arg Glu  Thr Ser Thr Ser Gln  Lys Ile Gly
    6365              6370                  6375

Ser Ser  Ser Asp Thr Ser Thr  Val Phe Asp Lys Ala  Phe Thr Ala
    6380              6385                  6390

Ala Thr  Thr Glu Val Ser Arg  Thr Glu Leu Thr Ser  Ser Ser Arg
    6395              6400                  6405

Thr Ser  Ile Gln Gly Thr Glu  Lys Pro Thr Met Ser  Pro Asp Thr
    6410              6415                  6420

Ser Thr  Arg Ser Val Thr Met  Leu Ser Thr Phe Ala  Gly Leu Thr
    6425              6430                  6435

Lys Ser  Glu Glu Arg Thr Ile  Ala Thr Gln Thr Gly  Pro His Arg
    6440              6445                  6450

Ala Thr  Ser Gln Gly Thr Leu  Thr Trp Asp Thr Ser  Ile Thr Thr
    6455              6460                  6465

Ser Gln  Ala Gly Thr His Ser  Ala Met Thr His Gly  Phe Ser Gln
    6470              6475                  6480

Leu Asp  Leu Ser Thr Leu Thr  Ser Arg Val Pro Glu  Tyr Ile Ser
    6485              6490                  6495

Gly Thr  Ser Pro Pro Ser Val  Glu Lys Thr Ser Ser  Ser Ser Ser
    6500              6505                  6510

Leu Leu  Ser Leu Pro Ala Ile  Thr Ser Pro Ser Pro  Val Pro Thr
    6515              6520                  6525

Thr Leu  Pro Glu Ser Arg Pro  Ser Ser Pro Val His  Leu Thr Ser
    6530              6535                  6540

Leu Pro  Thr Ser Gly Leu Val  Lys Thr Thr Asp Met  Leu Ala Ser
    6545              6550                  6555

Val Ala  Ser Leu Pro Pro Asn  Leu Gly Ser Thr Ser  His Lys Ile
    6560              6565                  6570

Pro Thr  Thr Ser Glu Asp Ile  Lys Asp Thr Glu Lys  Met Tyr Pro
    6575              6580                  6585

Ser Thr  Asn Ile Ala Val Thr  Asn Val Gly Thr Thr  Thr Ser Glu
    6590              6595                  6600

Lys Glu  Ser Tyr Ser Ser Val  Pro Ala Tyr Ser Glu  Pro Pro Lys
    6605              6610                  6615

Val Thr  Ser Pro Met Val Thr  Ser Phe Asn Ile Arg  Asp Thr Ile
```

-continued

```
              6620              6625              6630

Val Ser  Thr Ser Met Pro Gly  Ser Ser Glu Ile Thr  Arg Ile Glu
    6635              6640              6645

Met Glu  Ser Thr Phe Ser Leu  Ala His Gly Leu Lys  Gly Thr Ser
    6650              6655              6660

Thr Ser  Gln Asp Pro Ile Val  Ser Thr Glu Lys Ser  Ala Val Leu
    6665              6670              6675

His Lys  Leu Thr Thr Gly Ala  Thr Glu Thr Ser Arg  Thr Glu Val
    6680              6685              6690

Ala Ser  Ser Arg Arg Thr Ser  Ile Pro Gly Pro Asp  His Ser Thr
    6695              6700              6705

Glu Ser  Pro Asp Ile Ser Thr  Glu Val Ile Pro Ser  Leu Pro Ile
    6710              6715              6720

Ser Leu  Gly Ile Thr Glu Ser  Ser Asn Met Thr Ile  Ile Thr Arg
    6725              6730              6735

Thr Gly  Pro Pro Leu Gly Ser  Thr Ser Gln Gly Thr  Phe Thr Leu
    6740              6745              6750

Asp Thr  Pro Thr Thr Ser Ser  Arg Ala Gly Thr His  Ser Met Ala
    6755              6760              6765

Thr Gln  Glu Phe Pro His Ser  Glu Met Thr Thr Val  Met Asn Lys
    6770              6775              6780

Asp Pro  Glu Ile Leu Ser Trp  Thr Ile Pro Pro Ser  Ile Glu Lys
    6785              6790              6795

Thr Ser  Phe Ser Ser Ser Leu  Met Pro Ser Pro Ala  Met Thr Ser
    6800              6805              6810

Pro Pro  Val Ser Ser Thr Leu  Pro Lys Thr Ile His  Thr Thr Pro
    6815              6820              6825

Ser Pro  Met Thr Ser Leu Leu  Thr Pro Ser Leu Val  Met Thr Thr
    6830              6835              6840

Asp Thr  Leu Gly Thr Ser Pro  Glu Pro Thr Thr Ser  Ser Pro Pro
    6845              6850              6855

Asn Leu  Ser Ser Thr Ser His  Glu Ile Leu Thr Thr  Asp Glu Asp
    6860              6865              6870

Thr Thr  Ala Ile Glu Ala Met  His Pro Ser Thr Ser  Thr Ala Ala
    6875              6880              6885

Thr Asn  Val Glu Thr Thr Ser  Ser Gly His Gly Ser  Gln Ser Ser
    6890              6895              6900

Val Leu  Ala Asp Ser Glu Lys  Thr Lys Ala Thr Ala  Pro Met Asp
    6905              6910              6915

Thr Thr  Ser Thr Met Gly His  Thr Thr Val Ser Thr  Ser Met Ser
    6920              6925              6930

Val Ser  Ser Glu Thr Thr Lys  Ile Lys Arg Glu Ser  Thr Tyr Ser
    6935              6940              6945

Leu Thr  Pro Gly Leu Arg Glu  Thr Ser Ile Ser Gln  Asn Ala Ser
    6950              6955              6960

Phe Ser  Thr Asp Thr Ser Ile  Val Leu Ser Glu Val  Pro Thr Gly
    6965              6970              6975

Thr Thr  Ala Glu Val Ser Arg  Thr Glu Val Thr Ser  Ser Gly Arg
    6980              6985              6990

Thr Ser  Ile Pro Gly Pro Ser  Gln Ser Thr Val Leu  Pro Glu Ile
    6995              7000              7005

Ser Thr  Arg Thr Met Thr Arg  Leu Phe Ala Ser Pro  Thr Met Thr
    7010              7015              7020
```

-continued

```
Glu Ser Ala Glu Met Thr Ile Pro Thr Gln Thr Gly Pro Ser Gly
    7025                7030                7035

Ser Thr Ser Gln Asp Thr Leu Thr Leu Asp Thr Ser Thr Thr Lys
    7040                7045                7050

Ser Gln Ala Lys Thr His Ser Thr Leu Thr Gln Arg Phe Pro His
    7055                7060                7065

Ser Glu Met Thr Thr Leu Met Ser Arg Gly Pro Gly Asp Met Ser
    7070                7075                7080

Trp Gln Ser Ser Pro Ser Leu Glu Asn Pro Ser Ser Leu Pro Ser
    7085                7090                7095

Leu Leu Ser Leu Pro Ala Thr Thr Ser Pro Pro Pro Ile Ser Ser
    7100                7105                7110

Thr Leu Pro Val Thr Ile Ser Ser Ser Pro Leu Pro Val Thr Ser
    7115                7120                7125

Leu Leu Thr Ser Ser Pro Val Thr Thr Thr Asp Met Leu His Thr
    7130                7135                7140

Ser Pro Glu Leu Val Thr Ser Ser Pro Pro Lys Leu Ser His Thr
    7145                7150                7155

Ser Asp Glu Arg Leu Thr Thr Gly Lys Asp Thr Thr Asn Thr Glu
    7160                7165                7170

Ala Val His Pro Ser Thr Asn Thr Ala Ala Ser Asn Val Glu Ile
    7175                7180                7185

Pro Ser Ser Gly His Glu Ser Pro Ser Ser Ala Leu Ala Asp Ser
    7190                7195                7200

Glu Thr Ser Lys Ala Thr Ser Pro Met Phe Ile Thr Ser Thr Gln
    7205                7210                7215

Glu Asp Thr Thr Val Ala Ile Ser Thr Pro His Phe Leu Glu Thr
    7220                7225                7230

Ser Arg Ile Gln Lys Glu Ser Ile Ser Ser Leu Ser Pro Lys Leu
    7235                7240                7245

Arg Glu Thr Gly Ser Ser Val Glu Thr Ser Ser Ala Ile Glu Thr
    7250                7255                7260

Ser Ala Val Leu Ser Glu Val Ser Ile Gly Ala Thr Thr Glu Ile
    7265                7270                7275

Ser Arg Thr Glu Val Thr Ser Ser Ser Arg Thr Ser Ile Ser Gly
    7280                7285                7290

Ser Ala Glu Ser Thr Met Leu Pro Glu Ile Ser Thr Thr Arg Lys
    7295                7300                7305

Ile Ile Lys Phe Pro Thr Ser Pro Ile Leu Ala Glu Ser Ser Glu
    7310                7315                7320

Met Thr Ile Lys Thr Gln Thr Ser Pro Pro Gly Ser Thr Ser Glu
    7325                7330                7335

Ser Thr Phe Thr Leu Asp Thr Ser Thr Thr Pro Ser Leu Val Ile
    7340                7345                7350

Thr His Ser Thr Met Thr Gln Arg Leu Pro His Ser Glu Ile Thr
    7355                7360                7365

Thr Leu Val Ser Arg Gly Ala Gly Asp Val Pro Arg Pro Ser Ser
    7370                7375                7380

Leu Pro Val Glu Glu Thr Ser Pro Pro Ser Ser Gln Leu Ser Leu
    7385                7390                7395

Ser Ala Met Ile Ser Pro Ser Pro Val Ser Ser Thr Leu Pro Ala
    7400                7405                7410
```

-continued

```
Ser Ser  His Ser Ser Ser Ala  Ser Val Thr Ser Leu  Leu Thr Pro
    7415              7420              7425

Gly Gln  Val Lys Thr Thr Glu  Val Leu Asp Ala Ser  Ala Glu Pro
    7430              7435              7440

Glu Thr  Ser Ser Pro Pro Ser  Leu Ser Ser Thr Ser  Val Glu Ile
    7445              7450              7455

Leu Ala  Thr Ser Glu Val Thr  Thr Asp Thr Glu Lys  Ile His Pro
    7460              7465              7470

Phe Ser  Asn Thr Ala Val Thr  Lys Val Gly Thr Ser  Ser Ser Gly
    7475              7480              7485

His Glu  Ser Pro Ser Ser Val  Leu Pro Asp Ser Glu  Thr Thr Lys
    7490              7495              7500

Ala Thr  Ser Ala Met Gly Thr  Ile Ser Ile Met Gly  Asp Thr Ser
    7505              7510              7515

Val Ser  Thr Leu Thr Pro Ala  Leu Ser Asn Thr Arg  Lys Ile Gln
    7520              7525              7530

Ser Glu  Pro Ala Ser Ser Leu  Thr Thr Arg Leu Arg  Glu Thr Ser
    7535              7540              7545

Thr Ser  Glu Glu Thr Ser Leu  Ala Thr Glu Ala Asn  Thr Val Leu
    7550              7555              7560

Ser Lys  Val Ser Thr Gly Ala  Thr Thr Glu Val Ser  Arg Thr Glu
    7565              7570              7575

Ala Ile  Ser Phe Ser Arg Thr  Ser Met Ser Gly Pro  Glu Gln Ser
    7580              7585              7590

Thr Met  Ser Gln Asp Ile Ser  Ile Gly Thr Ile Pro  Arg Ile Ser
    7595              7600              7605

Ala Ser  Ser Val Leu Thr Glu  Ser Ala Lys Met Thr  Ile Thr Thr
    7610              7615              7620

Gln Thr  Gly Pro Ser Glu Ser  Thr Leu Glu Ser Thr  Leu Asn Leu
    7625              7630              7635

Asn Thr  Ala Thr Thr Pro Ser  Trp Val Glu Thr His  Ser Ile Val
    7640              7645              7650

Ile Gln  Gly Phe Pro His Pro  Glu Met Thr Thr Ser  Met Gly Arg
    7655              7660              7665

Gly Pro  Gly Gly Val Ser Trp  Pro Ser Pro Pro Phe  Val Lys Glu
    7670              7675              7680

Thr Ser  Pro Pro Ser Ser Pro  Leu Ser Leu Pro Ala  Val Thr Ser
    7685              7690              7695

Pro His  Pro Val Ser Thr Thr  Phe Leu Ala His Ile  Pro Pro Ser
    7700              7705              7710

Pro Leu  Pro Val Thr Ser Leu  Leu Thr Ser Gly Pro  Ala Thr Thr
    7715              7720              7725

Thr Asp  Ile Leu Gly Thr Ser  Thr Glu Pro Gly Thr  Ser Ser Ser
    7730              7735              7740

Ser Ser  Leu Ser Thr Thr Ser  His Glu Arg Leu Thr  Thr Tyr Lys
    7745              7750              7755

Asp Thr  Ala His Thr Glu Ala  Val His Pro Ser Thr  Asn Thr Gly
    7760              7765              7770

Gly Thr  Asn Val Ala Thr Thr  Ser Ser Gly Tyr Lys  Ser Gln Ser
    7775              7780              7785

Ser Val  Leu Ala Asp Ser Ser  Pro Met Cys Thr Thr  Ser Thr Met
    7790              7795              7800

Gly Asp  Thr Ser Val Leu Thr  Ser Thr Pro Ala Phe  Leu Glu Thr
```

-continued

```
         7805              7810              7815

Arg Arg  Ile Gln Thr Glu Leu  Ala Ser Ser Leu Thr  Pro Gly Leu
    7820              7825              7830

Arg Glu  Ser Ser Gly Ser Glu  Gly Thr Ser Ser Gly  Thr Lys Met
    7835              7840              7845

Ser Thr  Val Leu Ser Lys Val  Pro Thr Gly Ala Thr  Thr Glu Ile
    7850              7855              7860

Ser Lys  Glu Asp Val Thr Ser  Ile Pro Gly Pro Ala  Gln Ser Thr
    7865              7870              7875

Ile Ser  Pro Asp Ile Ser Thr  Arg Thr Val Ser Trp  Phe Ser Thr
    7880              7885              7890

Ser Pro  Val Met Thr Glu Ser  Ala Glu Ile Thr Met  Asn Thr His
    7895              7900              7905

Thr Ser  Pro Leu Gly Ala Thr  Thr Gln Gly Thr Ser  Thr Leu Asp
    7910              7915              7920

Thr Ser  Ser Thr Thr Ser Leu  Thr Met Thr His Ser  Thr Ile Ser
    7925              7930              7935

Gln Gly  Phe Ser His Ser Gln  Met Ser Thr Leu Met  Arg Arg Gly
    7940              7945              7950

Pro Glu  Asp Val Ser Trp Met  Ser Pro Pro Leu Leu  Glu Lys Thr
    7955              7960              7965

Arg Pro  Ser Phe Ser Leu Met  Ser Ser Pro Ala Thr  Thr Ser Pro
    7970              7975              7980

Ser Pro  Val Ser Ser Thr Leu  Pro Glu Ser Ile Ser  Ser Ser Pro
    7985              7990              7995

Leu Pro  Val Thr Ser Leu Leu  Thr Ser Gly Leu Ala  Lys Thr Thr
    8000              8005              8010

Asp Met  Leu His Lys Ser Ser  Glu Pro Val Thr Asn  Ser Pro Ala
    8015              8020              8025

Asn Leu  Ser Ser Thr Ser Val  Glu Ile Leu Ala Thr  Ser Glu Val
    8030              8035              8040

Thr Thr  Asp Thr Glu Lys Thr  His Pro Ser Ser Asn  Arg Thr Val
    8045              8050              8055

Thr Asp  Val Gly Thr Ser Ser  Ser Gly His Glu Ser  Thr Ser Phe
    8060              8065              8070

Val Leu  Ala Asp Ser Gln Thr  Ser Lys Val Thr Ser  Pro Met Val
    8075              8080              8085

Ile Thr  Ser Thr Met Glu Asp  Thr Ser Val Ser Thr  Ser Thr Pro
    8090              8095              8100

Gly Phe  Phe Glu Thr Ser Arg  Ile Gln Thr Glu Pro  Thr Ser Ser
    8105              8110              8115

Leu Thr  Leu Gly Leu Arg Lys  Thr Ser Ser Ser Glu  Gly Thr Ser
    8120              8125              8130

Leu Ala  Thr Glu Met Ser Thr  Val Leu Ser Gly Val  Pro Thr Gly
    8135              8140              8145

Ala Thr  Ala Glu Val Ser Arg  Thr Glu Val Thr Ser  Ser Ser Arg
    8150              8155              8160

Thr Ser  Ile Ser Gly Phe Ala  Gln Leu Thr Val Ser  Pro Glu Thr
    8165              8170              8175

Ser Thr  Glu Thr Ile Thr Arg  Leu Pro Thr Ser Ser  Ile Met Thr
    8180              8185              8190

Glu Ser  Ala Glu Met Met Ile  Lys Thr Gln Thr Asp  Pro Pro Gly
    8195              8200              8205
```

-continued

```
Ser Thr Pro Glu Ser Thr His  Thr Val Asp Ile Ser  Thr Thr Pro
    8210              8215              8220

Asn Trp Val Glu Thr His Ser  Thr Val Thr Gln Arg  Phe Ser His
    8225              8230              8235

Ser Glu Met Thr Thr Leu Val  Ser Arg Ser Pro Gly  Asp Met Leu
    8240              8245              8250

Trp Pro Ser Gln Ser Ser Val  Glu Glu Thr Ser Ser  Ala Ser Ser
    8255              8260              8265

Leu Leu Ser Leu Pro Ala Thr  Thr Ser Pro Ser Pro  Val Ser Ser
    8270              8275              8280

Thr Leu Val Glu Asp Phe Pro  Ser Ala Ser Leu Pro  Val Thr Ser
    8285              8290              8295

Leu Leu Asn Pro Gly Leu Val  Ile Thr Thr Asp Arg  Met Gly Ile
    8300              8305              8310

Ser Arg Glu Pro Gly Thr Ser  Ser Thr Ser Asn Leu  Ser Ser Thr
    8315              8320              8325

Ser His Glu Arg Leu Thr Thr  Leu Glu Asp Thr Val  Asp Thr Glu
    8330              8335              8340

Asp Met Gln Pro Ser Thr His  Thr Ala Val Thr Asn  Val Arg Thr
    8345              8350              8355

Ser Ile Ser Gly His Glu Ser  Gln Ser Ser Val Leu  Ser Asp Ser
    8360              8365              8370

Glu Thr Pro Lys Ala Thr Ser  Pro Met Gly Thr Thr  Tyr Thr Met
    8375              8380              8385

Gly Glu Thr Ser Val Ser Ile  Ser Thr Ser Asp Phe  Phe Glu Thr
    8390              8395              8400

Ser Arg Ile Gln Ile Glu Pro  Thr Ser Ser Leu Thr  Ser Gly Leu
    8405              8410              8415

Arg Glu Thr Ser Ser Ser Glu  Arg Ile Ser Ser Ala  Thr Glu Gly
    8420              8425              8430

Ser Thr Val Leu Ser Glu Val  Pro Ser Gly Ala Thr  Thr Glu Val
    8435              8440              8445

Ser Arg Thr Glu Val Ile Ser  Ser Arg Gly Thr Ser  Met Ser Gly
    8450              8455              8460

Pro Asp Gln Phe Thr Ile Ser  Pro Asp Ile Ser Thr  Glu Ala Ile
    8465              8470              8475

Thr Arg Leu Ser Thr Ser Pro  Ile Met Thr Glu Ser  Ala Glu Ser
    8480              8485              8490

Ala Ile Thr Ile Glu Thr Gly  Ser Pro Gly Ala Thr  Ser Glu Gly
    8495              8500              8505

Thr Leu Thr Leu Asp Thr Ser  Thr Thr Thr Phe Trp  Ser Gly Thr
    8510              8515              8520

His Ser Thr Ala Ser Pro Gly  Phe Ser His Ser Glu  Met Thr Thr
    8525              8530              8535

Leu Met Ser Arg Thr Pro Gly  Asp Val Pro Trp Pro  Ser Leu Pro
    8540              8545              8550

Ser Val Glu Glu Ala Ser Ser  Val Ser Ser Ser Leu  Ser Ser Pro
    8555              8560              8565

Ala Met Thr Ser Thr Ser Phe  Phe Ser Thr Leu Pro  Glu Ser Ile
    8570              8575              8580

Ser Ser Ser Pro His Pro Val  Thr Ala Leu Leu Thr  Leu Gly Pro
    8585              8590              8595
```

-continued

```
Val Lys  Thr Thr Asp Met Leu  Arg Thr Ser Ser Glu  Pro Glu Thr
    8600             8605              8610

Ser Ser  Pro Pro Asn Leu Ser  Ser Thr Ser Ala Glu  Ile Leu Ala
    8615             8620              8625

Thr Ser  Glu Val Thr Lys Asp  Arg Glu Lys Ile His  Pro Ser Ser
    8630             8635              8640

Asn Thr  Pro Val Val Asn Val  Gly Thr Val Ile Tyr  Lys His Leu
    8645             8650              8655

Ser Pro  Ser Ser Val Leu Ala  Asp Leu Val Thr Thr  Lys Pro Thr
    8660             8665              8670

Ser Pro  Met Ala Thr Thr Ser  Thr Leu Gly Asn Thr  Ser Val Ser
    8675             8680              8685

Thr Ser  Thr Pro Ala Phe Pro  Glu Thr Met Met Thr  Gln Pro Thr
    8690             8695              8700

Ser Ser  Leu Thr Ser Gly Leu  Arg Glu Ile Ser Thr  Ser Gln Glu
    8705             8710              8715

Thr Ser  Ser Ala Thr Glu Arg  Ser Ala Ser Leu Ser  Gly Met Pro
    8720             8725              8730

Thr Gly  Ala Thr Thr Lys Val  Ser Arg Thr Glu Ala  Leu Ser Leu
    8735             8740              8745

Gly Arg  Thr Ser Thr Pro Gly  Pro Ala Gln Ser Thr  Ile Ser Pro
    8750             8755              8760

Glu Ile  Ser Thr Glu Thr Ile  Thr Arg Ile Ser Thr  Pro Leu Thr
    8765             8770              8775

Thr Thr  Gly Ser Ala Glu Met  Thr Ile Thr Pro Lys  Thr Gly His
    8780             8785              8790

Ser Gly  Ala Ser Ser Gln Gly  Thr Phe Thr Leu Asp  Thr Ser Ser
    8795             8800              8805

Arg Ala  Ser Trp Pro Gly Thr  His Ser Ala Ala Thr  His Arg Ser
    8810             8815              8820

Pro His  Ser Gly Met Thr Thr  Pro Met Ser Arg Gly  Pro Glu Asp
    8825             8830              8835

Val Ser  Trp Pro Ser Arg Pro  Ser Val Glu Lys Thr  Ser Pro Pro
    8840             8845              8850

Ser Ser  Leu Val Ser Leu Ser  Ala Val Thr Ser Pro  Ser Pro Leu
    8855             8860              8865

Tyr Ser  Thr Pro Ser Glu Ser  Ser His Ser Ser Pro  Leu Arg Val
    8870             8875              8880

Thr Ser  Leu Phe Thr Pro Val  Met Met Lys Thr Thr  Asp Met Leu
    8885             8890              8895

Asp Thr  Ser Leu Glu Pro Val  Thr Thr Ser Pro Pro  Ser Met Asn
    8900             8905              8910

Ile Thr  Ser Asp Glu Ser Leu  Ala Thr Ser Lys Ala  Thr Met Glu
    8915             8920              8925

Thr Glu  Ala Ile Gln Leu Ser  Glu Asn Thr Ala Val  Thr Gln Met
    8930             8935              8940

Gly Thr  Ile Ser Ala Arg Gln  Glu Phe Tyr Ser Ser  Tyr Pro Gly
    8945             8950              8955

Leu Pro  Glu Pro Ser Lys Val  Thr Ser Pro Val Val  Thr Ser Ser
    8960             8965              8970

Thr Ile  Lys Asp Ile Val Ser  Thr Thr Ile Pro Ala  Ser Ser Glu
    8975             8980              8985

Ile Thr  Arg Ile Glu Met Glu  Ser Thr Ser Thr Leu  Thr Pro Thr
```

-continued

```
        8990                  8995                 9000

Pro Arg  Glu Thr Ser Thr Ser  Gln Glu Ile His Ser  Ala Thr Lys
    9005              9010                 9015

Pro Ser  Thr Val Pro Tyr Lys  Ala Leu Thr Ser Ala  Thr Ile Glu
    9020              9025                 9030

Asp Ser  Met Thr Gln Val Met  Ser Ser Ser Arg Gly  Pro Ser Pro
    9035              9040                 9045

Asp Gln  Ser Thr Met Ser Gln  Asp Ile Ser Thr Glu  Val Ile Thr
    9050              9055                 9060

Arg Leu  Ser Thr Ser Pro Ile  Lys Thr Glu Ser Thr  Glu Met Thr
    9065              9070                 9075

Ile Thr  Thr Gln Thr Gly Ser  Pro Gly Ala Thr Ser  Arg Gly Thr
    9080              9085                 9090

Leu Thr  Leu Asp Thr Ser Thr  Thr Phe Met Ser Gly  Thr His Ser
    9095              9100                 9105

Thr Ala  Ser Gln Gly Phe Ser  His Ser Gln Met Thr  Ala Leu Met
    9110              9115                 9120

Ser Arg  Thr Pro Gly Asp Val  Pro Trp Leu Ser His  Pro Ser Val
    9125              9130                 9135

Glu Glu  Ala Ser Ser Ala Ser  Phe Ser Leu Ser Ser  Pro Val Met
    9140              9145                 9150

Thr Ser  Ser Ser Pro Val Ser  Ser Thr Leu Pro Asp  Ser Ile His
    9155              9160                 9165

Ser Ser  Ser Leu Pro Val Thr  Ser Leu Leu Thr Ser  Gly Leu Val
    9170              9175                 9180

Lys Thr  Thr Glu Leu Leu Gly  Thr Ser Ser Glu Pro  Glu Thr Ser
    9185              9190                 9195

Ser Pro  Pro Asn Leu Ser Ser  Thr Ser Ala Glu Ile  Leu Ala Ile
    9200              9205                 9210

Thr Glu  Val Thr Thr Asp Thr  Glu Lys Leu Glu Met  Thr Asn Val
    9215              9220                 9225

Val Thr  Ser Gly Tyr Thr His  Glu Ser Pro Ser Ser  Val Leu Ala
    9230              9235                 9240

Asp Ser  Val Thr Thr Lys Ala  Thr Ser Ser Met Gly  Ile Thr Tyr
    9245              9250                 9255

Pro Thr  Gly Asp Thr Asn Val  Leu Thr Ser Thr Pro  Ala Phe Ser
    9260              9265                 9270

Asp Thr  Ser Arg Ile Gln Thr  Lys Ser Lys Leu Ser  Leu Thr Pro
    9275              9280                 9285

Gly Leu  Met Glu Thr Ser Ile  Ser Glu Glu Thr Ser  Ser Ala Thr
    9290              9295                 9300

Glu Lys  Ser Thr Val Leu Ser  Ser Val Pro Thr Gly  Ala Thr Thr
    9305              9310                 9315

Glu Val  Ser Arg Thr Glu Ala  Ile Ser Ser Ser Arg  Thr Ser Ile
    9320              9325                 9330

Pro Gly  Pro Ala Gln Ser Thr  Met Ser Ser Asp Thr  Ser Met Glu
    9335              9340                 9345

Thr Ile  Thr Arg Ile Ser Thr  Pro Leu Thr Arg Lys  Glu Ser Thr
    9350              9355                 9360

Asp Met  Ala Ile Thr Pro Lys  Thr Gly Pro Ser Gly  Ala Thr Ser
    9365              9370                 9375

Gln Gly  Thr Phe Thr Leu Asp  Ser Ser Ser Thr Ala  Ser Trp Pro
    9380              9385                 9390
```

-continued

```
Gly Thr His Ser Ala Thr Thr  Gln Arg Phe Pro Gln  Ser Val Val
9395                9400           9405

Thr Thr Pro Met Ser Arg Gly  Pro Glu Asp Val Ser  Trp Pro Ser
9410                9415           9420

Pro Leu Ser Val Glu Lys Asn  Ser Pro Pro Ser Ser  Leu Val Ser
9425                9430           9435

Ser Ser Ser Val Thr Ser Pro  Ser Pro Leu Tyr Ser  Thr Pro Ser
9440                9445           9450

Gly Ser Ser His Ser Ser Pro  Val Pro Val Thr Ser  Leu Phe Thr
9455                9460           9465

Ser Ile Met Met Lys Ala Thr  Asp Met Leu Asp Ala  Ser Leu Glu
9470                9475           9480

Pro Glu Thr Thr Ser Ala Pro  Asn Met Asn Ile Thr  Ser Asp Glu
9485                9490           9495

Ser Leu Ala Ala Ser Lys Ala  Thr Thr Glu Thr Glu  Ala Ile His
9500                9505           9510

Val Phe Glu Asn Thr Ala Ala  Ser His Val Glu Thr  Thr Ser Ala
9515                9520           9525

Thr Glu Glu Leu Tyr Ser Ser  Ser Pro Gly Phe Ser  Glu Pro Thr
9530                9535           9540

Lys Val Ile Ser Pro Val Val  Thr Ser Ser Ser Ile  Arg Asp Asn
9545                9550           9555

Met Val Ser Thr Thr Met Pro  Gly Ser Ser Gly Ile  Thr Arg Ile
9560                9565           9570

Glu Ile Glu Ser Met Ser Ser  Leu Thr Pro Gly Leu  Arg Glu Thr
9575                9580           9585

Arg Thr Ser Gln Asp Ile Thr  Ser Ser Thr Glu Thr  Ser Thr Val
9590                9595           9600

Leu Tyr Lys Met Pro Ser Gly  Ala Thr Pro Glu Val  Ser Arg Thr
9605                9610           9615

Glu Val Met Pro Ser Ser Arg  Thr Ser Ile Pro Gly  Pro Ala Gln
9620                9625           9630

Ser Thr Met Ser Leu Asp Ile  Ser Asp Glu Val Val  Thr Arg Leu
9635                9640           9645

Ser Thr Ser Pro Ile Met Thr  Glu Ser Ala Glu Ile  Thr Ile Thr
9650                9655           9660

Thr Gln Thr Gly Tyr Ser Leu  Ala Thr Ser Gln Val  Thr Leu Pro
9665                9670           9675

Leu Gly Thr Ser Met Thr Phe  Leu Ser Gly Thr His  Ser Thr Met
9680                9685           9690

Ser Gln Gly Leu Ser His Ser  Glu Met Thr Asn Leu  Met Ser Arg
9695                9700           9705

Gly Pro Glu Ser Leu Ser Trp  Thr Ser Pro Arg Phe  Val Glu Thr
9710                9715           9720

Thr Arg Ser Ser Ser Ser Leu  Thr Ser Leu Pro Leu  Thr Thr Ser
9725                9730           9735

Leu Ser Pro Val Ser Ser Thr  Leu Leu Asp Ser Ser  Pro Ser Ser
9740                9745           9750

Pro Leu Pro Val Thr Ser Leu  Ile Leu Pro Gly Leu  Val Lys Thr
9755                9760           9765

Thr Glu Val Leu Asp Thr Ser  Ser Glu Pro Lys Thr  Ser Ser Ser
9770                9775           9780
```

-continued

```
Pro Asn  Leu Ser Ser Thr Ser  Val Glu Ile Pro Ala  Thr Ser Glu
    9785              9790              9795

Ile Met  Thr Asp Thr Glu Lys  Ile His Pro Ser Ser  Asn Thr Ala
    9800              9805              9810

Val Ala  Lys Val Arg Thr Ser  Ser Ser Val His Glu  Ser His Ser
    9815              9820              9825

Ser Val  Leu Ala Asp Ser Glu  Thr Thr Ile Thr Ile  Pro Ser Met
    9830              9835              9840

Gly Ile  Thr Ser Ala Val Asp  Asp Thr Thr Val Phe  Thr Ser Asn
    9845              9850              9855

Pro Ala  Phe Ser Glu Thr Arg  Arg Ile Pro Thr Glu  Pro Thr Phe
    9860              9865              9870

Ser Leu  Thr Pro Gly Phe Arg  Glu Thr Ser Thr Ser  Glu Glu Thr
    9875              9880              9885

Thr Ser  Ile Thr Glu Thr Ser  Ala Val Leu Tyr Gly  Val Pro Thr
    9890              9895              9900

Ser Ala  Thr Thr Glu Val Ser  Met Thr Glu Ile Met  Ser Ser Asn
    9905              9910              9915

Arg Ile  His Ile Pro Asp Ser  Asp Gln Ser Thr Met  Ser Pro Asp
    9920              9925              9930

Ile Ile  Thr Glu Val Ile Thr  Arg Leu Ser Ser Ser  Ser Met Met
    9935              9940              9945

Ser Glu  Ser Thr Gln Met Thr  Ile Thr Thr Gln Lys  Ser Ser Pro
    9950              9955              9960

Gly Ala  Thr Ala Gln Ser Thr  Leu Thr Leu Ala Thr  Thr Thr Ala
    9965              9970              9975

Pro Leu  Ala Arg Thr His Ser  Thr Val Pro Pro Arg  Phe Leu His
    9980              9985              9990

Ser Glu  Met Thr Thr Leu Met  Ser Arg Ser Pro Glu  Asn Pro Ser
    9995              10000              10005

Trp Lys  Ser Ser Leu Phe Val  Glu Lys Thr Ser Ser  Ser Ser Ser
    10010              10015              10020

Leu Leu  Ser Leu Pro Val Thr  Thr Ser Pro Ser Val  Ser Ser Thr
    10025              10030              10035

Leu Pro  Gln Ser Ile Pro Ser  Ser Ser Phe Ser Val  Thr Ser Leu
    10040              10045              10050

Leu Thr  Pro Gly Met Val Lys  Thr Thr Asp Thr Ser  Thr Glu Pro
    10055              10060              10065

Gly Thr  Ser Leu Ser Pro Asn  Leu Ser Gly Thr Ser  Val Glu Ile
    10070              10075              10080

Leu Ala  Ala Ser Glu Val Thr  Thr Asp Thr Glu Lys  Ile His Pro
    10085              10090              10095

Ser Ser  Ser Met Ala Val Thr  Asn Val Gly Thr Thr  Ser Ser Gly
    10100              10105              10110

His Glu  Leu Tyr Ser Ser Val  Ser Ile His Ser Glu  Pro Ser Lys
    10115              10120              10125

Ala Thr  Tyr Pro Val Gly Thr  Pro Ser Ser Met Ala  Glu Thr Ser
    10130              10135              10140

Ile Ser  Thr Ser Met Pro Ala  Asn Phe Glu Thr Thr  Gly Phe Glu
    10145              10150              10155

Ala Glu  Pro Phe Ser His Leu  Thr Ser Gly Phe Arg  Lys Thr Asn
    10160              10165              10170

Met Ser  Leu Asp Thr Ser Ser  Val Thr Pro Thr Asn  Thr Pro Ser
```

```
     10175              10180              10185

Ser Pro  Gly Ser Thr His Leu  Leu Gln Ser Ser Lys  Thr Asp Phe
     10190              10195              10200

Thr Ser  Ser Ala Lys Thr Ser  Ser Pro Asp Trp Pro  Pro Ala Ser
     10205              10210              10215

Gln Tyr  Thr Glu Ile Pro Val  Asp Ile Ile Thr Pro  Phe Asn Ala
     10220              10225              10230

Ser Pro  Ser Ile Thr Glu Ser  Thr Gly Ile Thr Ser  Phe Pro Glu
     10235              10240              10245

Ser Arg  Phe Thr Met Ser Val  Thr Glu Ser Thr His  His Leu Ser
     10250              10255              10260

Thr Asp  Leu Leu Pro Ser Ala  Glu Thr Ile Ser Thr  Gly Thr Val
     10265              10270              10275

Met Pro  Ser Leu Ser Glu Ala  Met Thr Ser Phe Ala  Thr Thr Gly
     10280              10285              10290

Val Pro  Arg Ala Ile Ser Gly  Ser Gly Ser Pro Phe  Ser Arg Thr
     10295              10300              10305

Glu Ser  Gly Pro Gly Asp Ala  Thr Leu Ser Thr Ile  Ala Glu Ser
     10310              10315              10320

Leu Pro  Ser Ser Thr Pro Val  Pro Phe Ser Ser Ser  Thr Phe Thr
     10325              10330              10335

Thr Thr  Asp Ser Ser Thr Ile  Pro Ala Leu His Glu  Ile Thr Ser
     10340              10345              10350

Ser Ser  Ala Thr Pro Tyr Arg  Val Asp Thr Ser Leu  Gly Thr Glu
     10355              10360              10365

Ser Ser  Thr Thr Glu Gly Arg  Leu Val Met Val Ser  Thr Leu Asp
     10370              10375              10380

Thr Ser  Ser Gln Pro Gly Arg  Thr Ser Ser Ser Pro  Ile Leu Asp
     10385              10390              10395

Thr Arg  Met Thr Glu Ser Val  Glu Leu Gly Thr Val  Thr Ser Ala
     10400              10405              10410

Tyr Gln  Val Pro Ser Leu Ser  Thr Arg Leu Thr Arg  Thr Asp Gly
     10415              10420              10425

Ile Met  Glu His Ile Thr Lys  Ile Pro Asn Glu Ala  Ala His Arg
     10430              10435              10440

Gly Thr  Ile Arg Pro Val Lys  Gly Pro Gln Thr Ser  Thr Ser Pro
     10445              10450              10455

Ala Ser  Pro Lys Gly Leu His  Thr Gly Gly Thr Lys  Arg Met Glu
     10460              10465              10470

Thr Thr  Thr Thr Ala Leu Lys  Thr Thr Thr Thr Ala  Leu Lys Thr
     10475              10480              10485

Thr Ser  Arg Ala Thr Leu Thr  Thr Ser Val Tyr Thr  Pro Thr Leu
     10490              10495              10500

Gly Thr  Leu Thr Pro Leu Asn  Ala Ser Met Gln Met  Ala Ser Thr
     10505              10510              10515

Ile Pro  Thr Glu Met Met Ile  Thr Thr Pro Tyr Val  Phe Pro Asp
     10520              10525              10530

Val Pro  Glu Thr Thr Ser Ser  Leu Ala Thr Ser Leu  Gly Ala Glu
     10535              10540              10545

Thr Ser  Thr Ala Leu Pro Arg  Thr Thr Pro Ser Val  Phe Asn Arg
     10550              10555              10560

Glu Ser  Glu Thr Thr Ala Ser  Leu Val Ser Arg Ser  Gly Ala Glu
     10565              10570              10575
```

-continued

```
Arg Ser   Pro Val Ile Gln Thr   Leu Asp Val Ser Ser   Ser Glu Pro
    10580             10585              10590

Asp Thr   Thr Ala Ser Trp Val   Ile His Pro Ala Glu   Thr Ile Pro
    10595             10600              10605

Thr Val   Ser Lys Thr Thr Pro   Asn Phe Phe His Ser   Glu Leu Asp
    10610             10615              10620

Thr Val   Ser Ser Thr Ala Thr   Ser His Gly Ala Asp   Val Ser Ser
    10625             10630              10635

Ala Ile   Pro Thr Asn Ile Ser   Pro Ser Glu Leu Asp   Ala Leu Thr
    10640             10645              10650

Pro Leu   Val Thr Ile Ser Gly   Thr Asp Thr Ser Thr   Thr Phe Pro
    10655             10660              10665

Thr Leu   Thr Lys Ser Pro His   Glu Thr Glu Thr Arg   Thr Thr Trp
    10670             10675              10680

Leu Thr   His Pro Ala Glu Thr   Ser Ser Thr Ile Pro   Arg Thr Ile
    10685             10690              10695

Pro Asn   Phe Ser His His Glu   Ser Asp Ala Thr Pro   Ser Ile Ala
    10700             10705              10710

Thr Ser   Pro Gly Ala Glu Thr   Ser Ser Ala Ile Pro   Ile Met Thr
    10715             10720              10725

Val Ser   Pro Gly Ala Glu Asp   Leu Val Thr Ser Gln   Val Thr Ser
    10730             10735              10740

Ser Gly   Thr Asp Arg Asn Met   Thr Ile Pro Thr Leu   Thr Leu Ser
    10745             10750              10755

Pro Gly   Glu Pro Lys Thr Ile   Ala Ser Leu Val Thr   His Pro Glu
    10760             10765              10770

Ala Gln   Thr Ser Ser Ala Ile   Pro Thr Ser Thr Ile   Ser Pro Ala
    10775             10780              10785

Val Ser   Arg Leu Val Thr Ser   Met Val Thr Ser Leu   Ala Ala Lys
    10790             10795              10800

Thr Ser   Thr Thr Asn Arg Ala   Leu Thr Asn Ser Pro   Gly Glu Pro
    10805             10810              10815

Ala Thr   Thr Val Ser Leu Val   Thr His Pro Ala Gln   Thr Ser Pro
    10820             10825              10830

Thr Val   Pro Trp Thr Thr Ser   Ile Phe Phe His Ser   Lys Ser Asp
    10835             10840              10845

Thr Thr   Pro Ser Met Thr Thr   Ser His Gly Ala Glu   Ser Ser Ser
    10850             10855              10860

Ala Val   Pro Thr Pro Thr Val   Ser Thr Glu Val Pro   Gly Val Val
    10865             10870              10875

Thr Pro   Leu Val Thr Ser Ser   Arg Ala Val Ile Ser   Thr Thr Ile
    10880             10885              10890

Pro Ile   Leu Thr Leu Ser Pro   Gly Glu Pro Glu Thr   Thr Pro Ser
    10895             10900              10905

Met Ala   Thr Ser His Gly Glu   Glu Ala Ser Ser Ala   Ile Pro Thr
    10910             10915              10920

Pro Thr   Val Ser Pro Gly Val   Pro Gly Val Val Thr   Ser Leu Val
    10925             10930              10935

Thr Ser   Ser Arg Ala Val Thr   Ser Thr Thr Ile Pro   Ile Leu Thr
    10940             10945              10950

Phe Ser   Leu Gly Glu Pro Glu   Thr Thr Pro Ser Met   Ala Thr Ser
    10955             10960              10965
```

-continued

```
His Gly   Thr Glu Ala Gly Ser   Ala Val Pro Thr Val   Leu Pro Glu
    10970                 10975              10980

Val Pro   Gly Met Val Thr Ser   Leu Val Ala Ser Ser   Arg Ala Val
    10985                 10990              10995

Thr Ser   Thr Thr Leu Pro Thr   Leu Thr Leu Ser Pro   Gly Glu Pro
    11000                 11005              11010

Glu Thr   Thr Pro Ser Met Ala   Thr Ser His Gly Ala   Glu Ala Ser
    11015                 11020              11025

Ser Thr   Val Pro Thr Val Ser   Pro Glu Val Pro Gly   Val Val Thr
    11030                 11035              11040

Ser Leu   Val Thr Ser Ser Ser   Gly Val Asn Ser Thr   Ser Ile Pro
    11045                 11050              11055

Thr Leu   Ile Leu Ser Pro Gly   Glu Leu Glu Thr Thr   Pro Ser Met
    11060                 11065              11070

Ala Thr   Ser His Gly Ala Glu   Ala Ser Ser Ala Val   Pro Thr Pro
    11075                 11080              11085

Thr Val   Ser Pro Gly Val Ser   Gly Val Val Thr Pro   Leu Val Thr
    11090                 11095              11100

Ser Ser   Arg Ala Val Thr Ser   Thr Thr Ile Pro Ile   Leu Thr Leu
    11105                 11110              11115

Ser Ser   Ser Glu Pro Glu Thr   Thr Pro Ser Met Ala   Thr Ser His
    11120                 11125              11130

Gly Val   Glu Ala Ser Ser Ala   Val Leu Thr Val Ser   Pro Glu Val
    11135                 11140              11145

Pro Gly   Met Val Thr Ser Leu   Val Thr Ser Ser Arg   Ala Val Thr
    11150                 11155              11160

Ser Thr   Thr Ile Pro Thr Leu   Thr Ile Ser Ser Asp   Glu Pro Glu
    11165                 11170              11175

Thr Thr   Thr Ser Leu Val Thr   His Ser Glu Ala Lys   Met Ile Ser
    11180                 11185              11190

Ala Ile   Pro Thr Leu Ala Val   Ser Pro Thr Val Gln   Gly Leu Val
    11195                 11200              11205

Thr Ser   Leu Val Thr Ser Ser   Gly Ser Glu Thr Ser   Ala Phe Ser
    11210                 11215              11220

Asn Leu   Thr Val Ala Ser Ser   Gln Pro Glu Thr Ile   Asp Ser Trp
    11225                 11230              11235

Val Ala   His Pro Gly Thr Glu   Ala Ser Ser Val Val   Pro Thr Leu
    11240                 11245              11250

Thr Val   Ser Thr Gly Glu Pro   Phe Thr Asn Ile Ser   Leu Val Thr
    11255                 11260              11265

His Pro   Ala Glu Ser Ser Ser   Thr Leu Pro Arg Thr   Thr Ser Arg
    11270                 11275              11280

Phe Ser   His Ser Glu Leu Asp   Thr Met Pro Ser Thr   Val Thr Ser
    11285                 11290              11295

Pro Glu   Ala Glu Ser Ser Ser   Ala Ile Ser Thr Thr   Ile Ser Pro
    11300                 11305              11310

Gly Ile   Pro Gly Val Leu Thr   Ser Leu Val Thr Ser   Ser Gly Arg
    11315                 11320              11325

Asp Ile   Ser Ala Thr Phe Pro   Thr Val Pro Glu Ser   Pro His Glu
    11330                 11335              11340

Ser Glu   Ala Thr Ala Ser Trp   Val Thr His Pro Ala   Val Thr Ser
    11345                 11350              11355

Thr Thr   Val Pro Arg Thr Thr   Pro Asn Tyr Ser His   Ser Glu Pro
```

-continued

```
    11360              11365              11370

Asp Thr  Thr Pro Ser Ile Ala  Thr Ser Pro Gly Ala  Glu Ala Thr
    11375              11380              11385

Ser Asp  Phe Pro Thr Ile Thr  Val Ser Pro Asp Val  Pro Asp Met
    11390              11395              11400

Val Thr  Ser Gln Val Thr Ser  Ser Gly Thr Asp Thr  Ser Ile Thr
    11405              11410              11415

Ile Pro  Thr Leu Thr Leu Ser  Ser Gly Glu Pro Glu  Thr Thr Thr
    11420              11425              11430

Ser Phe  Ile Thr Tyr Ser Glu  Thr His Thr Ser Ser  Ala Ile Pro
    11435              11440              11445

Thr Leu  Pro Val Ser Pro Gly  Ala Ser Lys Met Leu  Thr Ser Leu
    11450              11455              11460

Val Ile  Ser Ser Gly Thr Asp  Ser Thr Thr Thr Phe  Pro Thr Leu
    11465              11470              11475

Thr Glu  Thr Pro Tyr Glu Pro  Glu Thr Thr Ala Ile  Gln Leu Ile
    11480              11485              11490

His Pro  Ala Glu Thr Asn Thr  Met Val Pro Arg Thr  Thr Pro Lys
    11495              11500              11505

Phe Ser  His Ser Lys Ser Asp  Thr Thr Leu Pro Val  Ala Ile Thr
    11510              11515              11520

Ser Pro  Gly Pro Glu Ala Ser  Ser Ala Val Ser Thr  Thr Thr Ile
    11525              11530              11535

Ser Pro  Asp Met Ser Asp Leu  Val Thr Ser Leu Val  Pro Ser Ser
    11540              11545              11550

Gly Thr  Asp Thr Ser Thr Thr  Phe Pro Thr Leu Ser  Glu Thr Pro
    11555              11560              11565

Tyr Glu  Pro Glu Thr Thr Ala  Thr Trp Leu Thr His  Pro Ala Glu
    11570              11575              11580

Thr Ser  Thr Thr Val Ser Gly  Thr Ile Pro Asn Phe  Ser His Arg
    11585              11590              11595

Gly Ser  Asp Thr Ala Pro Ser  Met Val Thr Ser Pro  Gly Val Asp
    11600              11605              11610

Thr Arg  Ser Gly Val Pro Thr  Thr Thr Ile Pro Pro  Ser Ile Pro
    11615              11620              11625

Gly Val  Val Thr Ser Gln Val  Thr Ser Ser Ala Thr  Asp Thr Ser
    11630              11635              11640

Thr Ala  Ile Pro Thr Leu Thr  Pro Ser Pro Gly Glu  Pro Glu Thr
    11645              11650              11655

Thr Ala  Ser Ser Ala Thr His  Pro Gly Thr Gln Thr  Gly Phe Thr
    11660              11665              11670

Val Pro  Ile Arg Thr Val Pro  Ser Ser Glu Pro Asp  Thr Met Ala
    11675              11680              11685

Ser Trp  Val Thr His Pro Pro  Gln Thr Ser Thr Pro  Val Ser Arg
    11690              11695              11700

Thr Thr  Ser Ser Phe Ser His  Ser Ser Pro Asp Ala  Thr Pro Val
    11705              11710              11715

Met Ala  Thr Ser Pro Arg Thr  Glu Ala Ser Ser Ala  Val Leu Thr
    11720              11725              11730

Thr Ile  Ser Pro Gly Ala Pro  Glu Met Val Thr Ser  Gln Ile Thr
    11735              11740              11745

Ser Ser  Gly Ala Ala Thr Ser  Thr Thr Val Pro Thr  Leu Thr His
    11750              11755              11760
```

-continued

```
Ser Pro  Gly Met Pro Glu Thr   Thr Ala Leu Leu Ser   Thr His Pro
    11765                11770                11775

Arg Thr  Glu Thr Ser Lys Thr   Phe Pro Ala Ser Thr   Val Phe Pro
    11780                11785                11790

Gln Val  Ser Glu Thr Thr Ala   Ser Leu Thr Ile Arg   Pro Gly Ala
    11795                11800                11805

Glu Thr  Ser Thr Ala Leu Pro   Thr Gln Thr Thr Ser   Ser Leu Phe
    11810                11815                11820

Thr Leu  Leu Val Thr Gly Thr   Ser Arg Val Asp Leu   Ser Pro Thr
    11825                11830                11835

Ala Ser  Pro Gly Val Ser Ala   Lys Thr Ala Pro Leu   Ser Thr His
    11840                11845                11850

Pro Gly  Thr Glu Thr Ser Thr   Met Ile Pro Thr Ser   Thr Leu Ser
    11855                11860                11865

Leu Gly  Leu Leu Glu Thr Thr   Gly Leu Leu Ala Thr   Ser Ser Ser
    11870                11875                11880

Ala Glu  Thr Ser Thr Ser Thr   Leu Thr Leu Thr Val   Ser Pro Ala
    11885                11890                11895

Val Ser  Gly Leu Ser Ser Ala   Ser Ile Thr Thr Asp   Lys Pro Gln
    11900                11905                11910

Thr Val  Thr Ser Trp Asn Thr   Glu Thr Ser Pro Ser   Val Thr Ser
    11915                11920                11925

Val Gly  Pro Pro Glu Phe Ser   Arg Thr Val Thr Gly   Thr Thr Met
    11930                11935                11940

Thr Leu  Ile Pro Ser Glu Met   Pro Thr Pro Pro Lys   Thr Ser His
    11945                11950                11955

Gly Glu  Gly Val Ser Pro Thr   Thr Ile Leu Arg Thr   Thr Met Val
    11960                11965                11970

Glu Ala  Thr Asn Leu Ala Thr   Thr Gly Ser Ser Pro   Thr Val Ala
    11975                11980                11985

Lys Thr  Thr Thr Thr Phe Asn   Thr Leu Ala Gly Ser   Leu Phe Thr
    11990                11995                12000

Pro Leu  Thr Thr Pro Gly Met   Ser Thr Leu Ala Ser   Glu Ser Val
    12005                12010                12015

Thr Ser  Arg Thr Ser Tyr Asn   His Arg Ser Trp Ile   Ser Thr Thr
    12020                12025                12030

Ser Ser  Tyr Asn Arg Arg Tyr   Trp Thr Pro Ala Thr   Ser Thr Pro
    12035                12040                12045

Val Thr  Ser Thr Phe Ser Pro   Gly Ile Ser Thr Ser   Ser Ile Pro
    12050                12055                12060

Ser Ser  Thr Ala Ala Thr Val   Pro Phe Met Val Pro   Phe Thr Leu
    12065                12070                12075

Asn Phe  Thr Ile Thr Asn Leu   Gln Tyr Glu Glu Asp   Met Arg His
    12080                12085                12090

Pro Gly  Ser Arg Lys Phe Asn   Ala Thr Glu Arg Glu   Leu Gln Gly
    12095                12100                12105

Leu Leu  Lys Pro Leu Phe Arg   Asn Ser Ser Leu Glu   Tyr Leu Tyr
    12110                12115                12120

Ser Gly  Cys Arg Leu Ala Ser   Leu Arg Pro Glu Lys   Asp Ser Ser
    12125                12130                12135

Ala Thr  Ala Val Asp Ala Ile   Cys Thr His Arg Pro   Asp Pro Glu
    12140                12145                12150
```

```
Asp Leu   Gly Leu Asp Arg Glu   Arg Leu Tyr Trp Glu   Leu Ser Asn
    12155                 12160                 12165

Leu Thr   Asn Gly Ile Gln Glu   Leu Gly Pro Tyr Thr   Leu Asp Arg
    12170                 12175                 12180

Asn Ser   Leu Tyr Val Asn Gly   Phe Thr His Arg Ser   Ser Met Pro
    12185                 12190                 12195

Thr Thr   Ser Thr Pro Gly Thr   Ser Thr Val Asp Val   Gly Thr Ser
    12200                 12205                 12210

Gly Thr   Pro Ser Ser Ser Pro   Ser Pro Thr Thr Ala   Gly Pro Leu
    12215                 12220                 12225

Leu Met   Pro Phe Thr Leu Asn   Phe Thr Ile Thr Asn   Leu Gln Tyr
    12230                 12235                 12240

Glu Glu   Asp Met Arg Arg Thr   Gly Ser Arg Lys Phe   Asn Thr Met
    12245                 12250                 12255

Glu Ser   Val Leu Gln Gly Leu   Leu Lys Pro Leu Phe   Lys Asn Thr
    12260                 12265                 12270

Ser Val   Gly Pro Leu Tyr Ser   Gly Cys Arg Leu Thr   Leu Leu Arg
    12275                 12280                 12285

Pro Glu   Lys Asp Gly Ala Ala   Thr Gly Val Asp Ala   Ile Cys Thr
    12290                 12295                 12300

His Arg   Leu Asp Pro Lys Ser   Pro Gly Leu Asn Arg   Glu Gln Leu
    12305                 12310                 12315

Tyr Trp   Glu Leu Ser Lys Leu   Thr Asn Asp Ile Glu   Glu Leu Gly
    12320                 12325                 12330

Pro Tyr   Thr Leu Asp Arg Asn   Ser Leu Tyr Val Asn   Gly Phe Thr
    12335                 12340                 12345

His Gln   Ser Ser Val Ser Thr   Thr Ser Thr Pro Gly   Thr Ser Thr
    12350                 12355                 12360

Val Asp   Leu Arg Thr Ser Gly   Thr Pro Ser Ser Leu   Ser Ser Pro
    12365                 12370                 12375

Thr Ile   Met Ala Ala Gly Pro   Leu Leu Val Pro Phe   Thr Leu Asn
    12380                 12385                 12390

Phe Thr   Ile Thr Asn Leu Gln   Tyr Gly Glu Asp Met   Gly His Pro
    12395                 12400                 12405

Gly Ser   Arg Lys Phe Asn Thr   Thr Glu Arg Val Leu   Gln Gly Leu
    12410                 12415                 12420

Leu Gly   Pro Ile Phe Lys Asn   Thr Ser Val Gly Pro   Leu Tyr Ser
    12425                 12430                 12435

Gly Cys   Arg Leu Thr Ser Leu   Arg Ser Glu Lys Asp   Gly Ala Ala
    12440                 12445                 12450

Thr Gly   Val Asp Ala Ile Cys   Ile His His Leu Asp   Pro Lys Ser
    12455                 12460                 12465

Pro Gly   Leu Asn Arg Glu Arg   Leu Tyr Trp Glu Leu   Ser Gln Leu
    12470                 12475                 12480

Thr Asn   Gly Ile Lys Glu Leu   Gly Pro Tyr Thr Leu   Asp Arg Asn
    12485                 12490                 12495

Ser Leu   Tyr Val Asn Gly Phe   Thr His Arg Thr Ser   Val Pro Thr
    12500                 12505                 12510

Ser Ser   Thr Pro Gly Thr Ser   Thr Val Asp Leu Gly   Thr Ser Gly
    12515                 12520                 12525

Thr Pro   Phe Ser Leu Pro Ser   Pro Ala Thr Ala Gly   Pro Leu Leu
    12530                 12535                 12540

Val Leu   Phe Thr Leu Asn Phe   Thr Ile Thr Asn Leu   Lys Tyr Glu
```

-continued

```
    12545              12550              12555

Glu Asp  Met His Arg Pro Gly  Ser Arg Lys Phe Asn  Thr Thr Glu
    12560              12565              12570

Arg Val  Leu Gln Thr Leu Leu  Gly Pro Met Phe Lys  Asn Thr Ser
    12575              12580              12585

Val Gly  Leu Leu Tyr Ser Gly  Cys Arg Leu Thr Leu  Leu Arg Ser
    12590              12595              12600

Glu Lys  Asp Gly Ala Ala Thr  Gly Val Asp Ala Ile  Cys Thr His
    12605              12610              12615

Arg Leu  Asp Pro Lys Ser Pro  Gly Val Asp Arg Glu  Gln Leu Tyr
    12620              12625              12630

Trp Glu  Leu Ser Gln Leu Thr  Asn Gly Ile Lys Glu  Leu Gly Pro
    12635              12640              12645

Tyr Thr  Leu Asp Arg Asn Ser  Leu Tyr Val Asn Gly  Phe Thr His
    12650              12655              12660

Trp Ile  Pro Val Pro Thr Ser  Ser Thr Pro Gly Thr  Ser Thr Val
    12665              12670              12675

Asp Leu  Gly Ser Gly Thr Pro  Ser Ser Leu Pro Ser  Pro Thr Thr
    12680              12685              12690

Ala Gly  Pro Leu Leu Val Pro  Phe Thr Leu Asn Phe  Thr Ile Thr
    12695              12700              12705

Asn Leu  Lys Tyr Glu Glu Asp  Met His Cys Pro Gly  Ser Arg Lys
    12710              12715              12720

Phe Asn  Thr Thr Glu Arg Val  Leu Gln Ser Leu Leu  Gly Pro Met
    12725              12730              12735

Phe Lys  Asn Thr Ser Val Gly  Pro Leu Tyr Ser Gly  Cys Arg Leu
    12740              12745              12750

Thr Leu  Leu Arg Ser Glu Lys  Asp Gly Ala Ala Thr  Gly Val Asp
    12755              12760              12765

Ala Ile  Cys Thr His Arg Leu  Asp Pro Lys Ser Pro  Gly Val Asp
    12770              12775              12780

Arg Glu  Gln Leu Tyr Trp Glu  Leu Ser Gln Leu Thr  Asn Gly Ile
    12785              12790              12795

Lys Glu  Leu Gly Pro Tyr Thr  Leu Asp Arg Asn Ser  Leu Tyr Val
    12800              12805              12810

Asn Gly  Phe Thr His Gln Thr  Ser Ala Pro Asn Thr  Ser Thr Pro
    12815              12820              12825

Gly Thr  Ser Thr Val Asp Leu  Gly Thr Ser Gly Thr  Pro Ser Ser
    12830              12835              12840

Leu Pro  Ser Pro Thr Ser Ala  Gly Pro Leu Leu Val  Pro Phe Thr
    12845              12850              12855

Leu Asn  Phe Thr Ile Thr Asn  Leu Gln Tyr Glu Glu  Asp Met His
    12860              12865              12870

His Pro  Gly Ser Arg Lys Phe  Asn Thr Thr Glu Arg  Val Leu Gln
    12875              12880              12885

Gly Leu  Leu Gly Pro Met Phe  Lys Asn Thr Ser Val  Gly Leu Leu
    12890              12895              12900

Tyr Ser  Gly Cys Arg Leu Thr  Leu Leu Arg Pro Glu  Lys Asn Gly
    12905              12910              12915

Ala Ala  Thr Gly Met Asp Ala  Ile Cys Ser His Arg  Leu Asp Pro
    12920              12925              12930

Lys Ser  Pro Gly Leu Asn Arg  Glu Gln Leu Tyr Trp  Glu Leu Ser
    12935              12940              12945
```

-continued

```
Gln Leu  Thr His Gly Ile Lys  Glu Leu Gly Pro Tyr  Thr Leu Asp
    12950             12955             12960

Arg Asn  Ser Leu Tyr Val Asn  Gly Phe Thr His Arg  Ser Ser Val
    12965             12970             12975

Ala Pro  Thr Ser Thr Pro Gly  Thr Ser Thr Val Asp  Leu Gly Thr
    12980             12985             12990

Ser Gly  Thr Pro Ser Ser Leu  Pro Ser Pro Thr Thr  Ala Val Pro
    12995             13000             13005

Leu Leu  Val Pro Phe Thr Leu  Asn Phe Thr Ile Thr  Asn Leu Gln
    13010             13015             13020

Tyr Gly  Glu Asp Met Arg His  Pro Gly Ser Arg Lys  Phe Asn Thr
    13025             13030             13035

Thr Glu  Arg Val Leu Gln Gly  Leu Leu Gly Pro Leu  Phe Lys Asn
    13040             13045             13050

Ser Ser  Val Gly Pro Leu Tyr  Ser Gly Cys Arg Leu  Ile Ser Leu
    13055             13060             13065

Arg Ser  Glu Lys Asp Gly Ala  Ala Thr Gly Val Asp  Ala Ile Cys
    13070             13075             13080

Thr His  His Leu Asn Pro Gln  Ser Pro Gly Leu Asp  Arg Glu Gln
    13085             13090             13095

Leu Tyr  Trp Gln Leu Ser Gln  Met Thr Asn Gly Ile  Lys Glu Leu
    13100             13105             13110

Gly Pro  Tyr Thr Leu Asp Arg  Asn Ser Leu Tyr Val  Asn Gly Phe
    13115             13120             13125

Thr His  Arg Ser Ser Gly Leu  Thr Thr Ser Thr Pro  Trp Thr Ser
    13130             13135             13140

Thr Val  Asp Leu Gly Thr Ser  Gly Thr Pro Ser Pro  Val Pro Ser
    13145             13150             13155

Pro Thr  Thr Thr Gly Pro Leu  Leu Val Pro Phe Thr  Leu Asn Phe
    13160             13165             13170

Thr Ile  Thr Asn Leu Gln Tyr  Glu Glu Asn Met Gly  His Pro Gly
    13175             13180             13185

Ser Arg  Lys Phe Asn Ile Thr  Glu Ser Val Leu Gln  Gly Leu Leu
    13190             13195             13200

Lys Pro  Leu Phe Lys Ser Thr  Ser Val Gly Pro Leu  Tyr Ser Gly
    13205             13210             13215

Cys Arg  Leu Thr Leu Leu Arg  Pro Glu Lys Asp Gly  Val Ala Thr
    13220             13225             13230

Arg Val  Asp Ala Ile Cys Thr  His Arg Pro Asp Pro  Lys Ile Pro
    13235             13240             13245

Gly Leu  Asp Arg Gln Gln Leu  Tyr Trp Glu Leu Ser  Gln Leu Thr
    13250             13255             13260

His Ser  Ile Thr Glu Leu Gly  Pro Tyr Thr Leu Asp  Arg Asp Ser
    13265             13270             13275

Leu Tyr  Val Asn Gly Phe Thr  Gln Arg Ser Ser Val  Pro Thr Thr
    13280             13285             13290

Ser Thr  Pro Gly Thr Phe Thr  Val Gln Pro Glu Thr  Ser Glu Thr
    13295             13300             13305

Pro Ser  Ser Leu Pro Gly Pro  Thr Ala Thr Gly Pro  Val Leu Leu
    13310             13315             13320

Pro Phe  Thr Leu Asn Phe Thr  Ile Thr Asn Leu Gln  Tyr Glu Glu
    13325             13330             13335
```

-continued

```
Asp Met  Arg Arg Pro Gly Ser  Arg Lys Phe Asn Thr  Thr Glu Arg
    13340             13345             13350

Val Leu  Gln Gly Leu Leu Met  Pro Leu Phe Lys Asn  Thr Ser Val
    13355             13360             13365

Ser Ser  Leu Tyr Ser Gly Cys  Arg Leu Thr Leu Leu  Arg Pro Glu
    13370             13375             13380

Lys Asp  Gly Ala Ala Thr Arg  Val Asp Ala Val Cys  Thr His Arg
    13385             13390             13395

Pro Asp  Pro Lys Ser Pro Gly  Leu Asp Arg Glu Arg  Leu Tyr Trp
    13400             13405             13410

Lys Leu  Ser Gln Leu Thr His  Gly Ile Thr Glu Leu  Gly Pro Tyr
    13415             13420             13425

Thr Leu  Asp Arg His Ser Leu  Tyr Val Asn Gly Phe  Thr His Gln
    13430             13435             13440

Ser Ser  Met Thr Thr Thr Arg  Thr Pro Asp Thr Ser  Thr Met His
    13445             13450             13455

Leu Ala  Thr Ser Arg Thr Pro  Ala Ser Leu Ser Gly  Pro Met Thr
    13460             13465             13470

Ala Ser  Pro Leu Leu Val Leu  Phe Thr Ile Asn Phe  Thr Ile Thr
    13475             13480             13485

Asn Leu  Arg Tyr Glu Glu Asn  Met His His Pro Gly  Ser Arg Lys
    13490             13495             13500

Phe Asn  Thr Thr Glu Arg Val  Leu Gln Gly Leu Leu  Arg Pro Val
    13505             13510             13515

Phe Lys  Asn Thr Ser Val Gly  Pro Leu Tyr Ser Gly  Cys Arg Leu
    13520             13525             13530

Thr Leu  Leu Arg Pro Lys Lys  Asp Gly Ala Ala Thr  Lys Val Asp
    13535             13540             13545

Ala Ile  Cys Thr Tyr Arg Pro  Asp Pro Lys Ser Pro  Gly Leu Asp
    13550             13555             13560

Arg Glu  Gln Leu Tyr Trp Glu  Leu Ser Gln Leu Thr  His Ser Ile
    13565             13570             13575

Thr Glu  Leu Gly Pro Tyr Thr  Leu Asp Arg Asp Ser  Leu Tyr Val
    13580             13585             13590

Asn Gly  Phe Thr Gln Arg Ser  Ser Val Pro Thr Thr  Ser Ile Pro
    13595             13600             13605

Gly Thr  Pro Thr Val Asp Leu  Gly Thr Ser Gly Thr  Pro Val Ser
    13610             13615             13620

Lys Pro  Gly Pro Ser Ala Ala  Ser Pro Leu Leu Val  Leu Phe Thr
    13625             13630             13635

Leu Asn  Phe Thr Ile Thr Asn  Leu Arg Tyr Glu Glu  Asn Met Gln
    13640             13645             13650

His Pro  Gly Ser Arg Lys Phe  Asn Thr Thr Glu Arg  Val Leu Gln
    13655             13660             13665

Gly Leu  Leu Arg Ser Leu Phe  Lys Ser Thr Ser Val  Gly Pro Leu
    13670             13675             13680

Tyr Ser  Gly Cys Arg Leu Thr  Leu Leu Arg Pro Glu  Lys Asp Gly
    13685             13690             13695

Thr Ala  Thr Gly Val Asp Ala  Ile Cys Thr His His  Pro Asp Pro
    13700             13705             13710

Lys Ser  Pro Arg Leu Asp Arg  Glu Gln Leu Tyr Trp  Glu Leu Ser
    13715             13720             13725

Gln Leu  Thr His Asn Ile Thr  Glu Leu Gly Pro Tyr  Ala Leu Asp
```

-continued

```
          13730                  13735                  13740

Asn Asp  Ser Leu Phe Val Asn  Gly Phe Thr His Arg  Ser Ser Val
    13745                  13750                  13755

Ser Thr  Thr Ser Thr Pro Gly  Thr Pro Thr Val Tyr  Leu Gly Ala
    13760                  13765                  13770

Ser Lys  Thr Pro Ala Ser Ile  Phe Gly Pro Ser Ala  Ala Ser His
    13775                  13780                  13785

Leu Leu  Ile Leu Phe Thr Leu  Asn Phe Thr Ile Thr  Asn Leu Arg
    13790                  13795                  13800

Tyr Glu  Glu Asn Met Trp Pro  Gly Ser Arg Lys Phe  Asn Thr Thr
    13805                  13810                  13815

Glu Arg  Val Leu Gln Gly Leu  Leu Arg Pro Leu Phe  Lys Asn Thr
    13820                  13825                  13830

Ser Val  Gly Pro Leu Tyr Ser  Gly Cys Arg Leu Thr  Leu Leu Arg
    13835                  13840                  13845

Pro Glu  Lys Asp Gly Glu Ala  Thr Gly Val Asp Ala  Ile Cys Thr
    13850                  13855                  13860

His Arg  Pro Asp Pro Thr Gly  Pro Gly Leu Asp Arg  Glu Gln Leu
    13865                  13870                  13875

Tyr Leu  Glu Leu Ser Gln Leu  Thr His Ser Ile Thr  Glu Leu Gly
    13880                  13885                  13890

Pro Tyr  Thr Leu Asp Arg Asp  Ser Leu Tyr Val Asn  Gly Phe Thr
    13895                  13900                  13905

His Arg  Ser Ser Val Pro Thr  Thr Ser Thr Gly Val  Val Ser Glu
    13910                  13915                  13920

Glu Pro  Phe Thr Leu Asn Phe  Thr Ile Asn Asn Leu  Arg Tyr Met
    13925                  13930                  13935

Ala Asp  Met Gly Gln Pro Gly  Ser Leu Lys Phe Asn  Ile Thr Asp
    13940                  13945                  13950

Asn Val  Met Gln His Leu Leu  Ser Pro Leu Phe Gln  Arg Ser Ser
    13955                  13960                  13965

Leu Gly  Ala Arg Tyr Thr Gly  Cys Arg Val Ile Ala  Leu Arg Ser
    13970                  13975                  13980

Val Lys  Asn Gly Ala Glu Thr  Arg Val Asp Leu Leu  Cys Thr Tyr
    13985                  13990                  13995

Leu Gln  Pro Leu Ser Gly Pro  Gly Leu Pro Ile Lys  Gln Val Phe
    14000                  14005                  14010

His Glu  Leu Ser Gln Gln Thr  His Gly Ile Thr Arg  Leu Gly Pro
    14015                  14020                  14025

Tyr Ser  Leu Asp Lys Asp Ser  Leu Tyr Leu Asn Gly  Tyr Asn Glu
    14030                  14035                  14040

Pro Gly  Pro Asp Glu Pro Pro  Thr Thr Pro Lys Pro  Ala Thr Thr
    14045                  14050                  14055

Phe Leu  Pro Pro Leu Ser Glu  Ala Thr Thr Ala Met  Gly Tyr His
    14060                  14065                  14070

Leu Lys  Thr Leu Thr Leu Asn  Phe Thr Ile Ser Asn  Leu Gln Tyr
    14075                  14080                  14085

Ser Pro  Asp Met Gly Lys Gly  Ser Ala Thr Phe Asn  Ser Thr Glu
    14090                  14095                  14100

Gly Val  Leu Gln His Leu Leu  Arg Pro Leu Phe Gln  Lys Ser Ser
    14105                  14110                  14115

Met Gly  Pro Phe Tyr Leu Gly  Cys Gln Leu Ile Ser  Leu Arg Pro
    14120                  14125                  14130
```

-continued

```
Glu Lys  Asp Gly Ala Ala Thr  Gly Val Asp Thr Thr  Cys Thr Tyr
    14135              14140              14145

His Pro  Asp Pro Val Gly Pro  Gly Leu Asp Ile Gln  Gln Leu Tyr
    14150              14155              14160

Trp Glu  Leu Ser Gln Leu Thr  His Gly Val Thr Gln  Leu Gly Phe
    14165              14170              14175

Tyr Val  Leu Asp Arg Asp Ser  Leu Phe Ile Asn Gly  Tyr Ala Pro
    14180              14185              14190

Gln Asn  Leu Ser Ile Arg Gly  Glu Tyr Gln Ile Asn  Phe His Ile
    14195              14200              14205

Val Asn  Trp Asn Leu Ser Asn  Pro Asp Pro Thr Ser  Ser Glu Tyr
    14210              14215              14220

Ile Thr  Leu Leu Arg Asp Ile  Gln Asp Lys Val Thr  Thr Leu Tyr
    14225              14230              14235

Lys Gly  Ser Gln Leu His Asp  Thr Phe Arg Phe Cys  Leu Val Thr
    14240              14245              14250

Asn Leu  Thr Met Asp Ser Val  Leu Val Thr Val Lys  Ala Leu Phe
    14255              14260              14265

Ser Ser  Asn Leu Asp Pro Ser  Leu Val Glu Gln Val  Phe Leu Asp
    14270              14275              14280

Lys Thr  Leu Asn Ala Ser Phe  His Trp Leu Gly Ser  Thr Tyr Gln
    14285              14290              14295

Leu Val  Asp Ile His Val Thr  Glu Met Glu Ser Ser  Val Tyr Gln
    14300              14305              14310

Pro Thr  Ser Ser Ser Ser Thr  Gln His Phe Tyr Leu  Asn Phe Thr
    14315              14320              14325

Ile Thr  Asn Leu Pro Tyr Ser  Gln Asp Lys Ala Gln  Pro Gly Thr
    14330              14335              14340

Thr Asn  Tyr Gln Arg Asn Lys  Arg Asn Ile Glu Asp  Ala Leu Asn
    14345              14350              14355

Gln Leu  Phe Arg Asn Ser Ser  Ile Lys Ser Tyr Phe  Ser Asp Cys
    14360              14365              14370

Gln Val  Ser Thr Phe Arg Ser  Val Pro Asn Arg His  His Thr Gly
    14375              14380              14385

Val Asp  Ser Leu Cys Asn Phe  Ser Pro Leu Ala Arg  Arg Val Asp
    14390              14395              14400

Arg Val  Ala Ile Tyr Glu Glu  Phe Leu Arg Met Thr  Arg Asn Gly
    14405              14410              14415

Thr Gln  Leu Gln Asn Phe Thr  Leu Asp Arg Ser Ser  Val Leu Val
    14420              14425              14430

Asp Gly  Tyr Ser Pro Asn Arg  Asn Glu Pro Leu Thr  Gly Asn Ser
    14435              14440              14445

Asp Leu  Pro Phe Trp Ala Val  Ile Leu Ile Gly Leu  Ala Gly Leu
    14450              14455              14460

Leu Gly  Val Ile Thr Cys Leu  Ile Cys Gly Val Leu  Val Thr Thr
    14465              14470              14475

Arg Arg  Arg Lys Lys Glu Gly  Glu Tyr Asn Val Gln  Gln Gln Cys
    14480              14485              14490

Pro Gly  Tyr Tyr Gln Ser His  Leu Asp Leu Glu Asp  Leu Gln
    14495              14500              14505
```

<210> SEQ ID NO 174
<211> LENGTH: 25

-continued

```
<212> TYPE: PRT
<213> ORGANISM: Artificial Sequence
<220> FEATURE:
<223> OTHER INFORMATION: synthetic

<400> SEQUENCE: 174

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 175
<211> LENGTH: 17
<212> TYPE: PRT
<213> ORGANISM: Artificial Sequence
<220> FEATURE:
<223> OTHER INFORMATION: synthetic

<400> SEQUENCE: 175

Met His Trp Val Arg Gln Ala Pro Gly Lys Gly Leu Glu Trp Val Ser
1               5                   10                  15

Gly

<210> SEQ ID NO 176
<211> LENGTH: 38
<212> TYPE: PRT
<213> ORGANISM: Artificial Sequence
<220> FEATURE:
<223> OTHER INFORMATION: synthetic

<400> SEQUENCE: 176

Gly Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys
        35

<210> SEQ ID NO 177
<211> LENGTH: 11
<212> TYPE: PRT
<213> ORGANISM: Artificial Sequence
<220> FEATURE:
<223> OTHER INFORMATION: synthetic

<400> SEQUENCE: 177

Trp Gly Gln Gly Thr Thr Val Thr Val Ser Ser
1               5                   10

<210> SEQ ID NO 178
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (8)..(8)
<223> OTHER INFORMATION: Xaa = Ala or Ser

<400> SEQUENCE: 178

Gly Phe Thr Phe Asp Asp Tyr Xaa
1               5

<210> SEQ ID NO 179
```

```
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (8)..(8)
<223> OTHER INFORMATION: Xaa = Lys or Ile

<400> SEQUENCE: 179

Ile Ser Trp Asn Ser Gly Ser Xaa
1               5

<210> SEQ ID NO 180
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (3)..(3)
<223> OTHER INFORMATION: Xaa = Tyr or Asp
<220> FEATURE:
<221> NAME/KEY: VARIANT
<222> LOCATION: (12)..(12)
<223> OTHER INFORMATION: Xaa = Tyr or His
<220> FEATURE:
<221> NAME/KEY: VARIANT
<222> LOCATION: (15)..(15)
<223> OTHER INFORMATION: Xaa = Met or Leu
<220> FEATURE:
<221> NAME/KEY: VARIANT
<222> LOCATION: (15)..(15)
<223> OTHER INFORMATION: Xaa = Met or Leu

<400> SEQUENCE: 180

Ala Lys Xaa Gly Ser Gly Tyr Gly Lys Phe Tyr Xaa Tyr Gly Xaa Asp
1               5                   10                  15

Val

<210> SEQ ID NO 181
<211> LENGTH: 125
<212> TYPE: PRT
<213> ORGANISM: Artificial Sequence
<220> FEATURE:
<223> OTHER INFORMATION: synthetic

<400> SEQUENCE: 181

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Tyr Ser Gly Tyr Gly Tyr Phe Tyr Tyr Tyr Gly Met
            100                 105                 110

Asp Val Trp Gly Gln Gly Thr Thr Val Thr Val Ser Ser
            115                 120                 125
```

-continued

<210> SEQ ID NO 182
<211> LENGTH: 330
<212> TYPE: PRT
<213> ORGANISM: Artificial Sequence
<220> FEATURE:
<223> OTHER INFORMATION: synthetic

<400> SEQUENCE: 182

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 183
<211> LENGTH: 330
<212> TYPE: PRT
<213> ORGANISM: Artificial Sequence -continued

```
<220> FEATURE:
<223> OTHER INFORMATION: synthetic

<400> SEQUENCE: 183

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 184
<211> LENGTH: 326
<212> TYPE: PRT
<213> ORGANISM: Artificial Sequence
<220> FEATURE:
<223> OTHER INFORMATION: synthetic

<400> SEQUENCE: 184

Ala Ser Thr Lys Gly Pro Ser Val Phe Pro Leu Ala Pro Cys Ser Arg
```

-continued

```
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
            85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
    130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
            165             170             175

Ser Thr Phe Arg Val Val Ser Val Leu Thr Val Val His Gln Asp Trp
            180             185             190

Leu Asn Gly Lys Glu Tyr Lys Cys Lys Val Ser Asn Lys Gly Leu Pro
            195             200             205

Ala Pro Ile Glu Lys Thr Ile Ser Lys Thr Lys Gly Gln Pro Arg Glu
    210             215             220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
            245             250             255

Ser Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
    290             295             300

Ser Val Met His Glu Ala Leu His Asn His Tyr Thr Gln Lys Ser Leu
305             310             315             320

Ser Leu Ser Pro Gly Lys
            325
```

<210> SEQ ID NO 185
<211> LENGTH: 326
<212> TYPE: PRT
<213> ORGANISM: Artificial Sequence
<220> FEATURE:
<223> OTHER INFORMATION: synthetic

<400> SEQUENCE: 185

```
Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
```

-continued

```
                35                    40                    45

Gly Val His Thr Phe Pro Ala Val Leu Gln Ser Ser Gly Leu Tyr Ser
    50                    55                    60

Leu Ser Ser Val Val Thr Val Pro Ser Ser Asn Phe Gly Thr Gln Thr
65                    70                    75                    80

Tyr Thr Cys Asn Val Asp His Lys Pro Ser Asn Thr Lys Val Asp Lys
                85                    90                    95

Thr Val Glu Arg Lys Cys Cys Val Glu Cys Pro Pro Cys Pro Ala Pro
                100                   105                   110

Pro Val Ala Gly Pro Ser Val Phe Leu Phe Pro Pro Lys Pro Lys Asp
                115                   120                   125

Thr Leu Met Ile Ser Arg Thr Pro Glu Val Thr Cys Val Val Val Asp
                130                   135                   140

Val Ser His Glu Asp Pro Glu Val Gln Phe Asn Trp Tyr Val Asp Gly
145                   150                   155                   160

Val Glu Val His Asn Ala Lys Thr Lys Pro Arg Glu Glu Gln Phe Asn
                165                   170                   175

Ser Thr Phe Arg Val Val Ser Val Leu Thr Val Val His Gln Asp Trp
                180                   185                   190

Leu Asn Gly Lys Glu Tyr Lys Cys Lys Val Ser Asn Lys Gly Leu Pro
                195                   200                   205

Ala Pro Ile Glu Lys Thr Ile Ser Lys Thr Lys Gly Gln Pro Arg Glu
    210                   215                   220

Pro Gln Val Tyr Thr Leu Pro Pro Ser Arg Glu Glu Met Thr Lys Asn
225                   230                   235                   240

Gln Val Ser Leu Thr Cys Leu Val Lys Gly Phe Tyr Pro Ser Asp Ile
                245                   250                   255

Ser Val Glu Trp Glu Ser Asn Gly Gln Pro Glu Asn Asn Tyr Lys Thr
                260                   265                   270

Thr Pro Pro Met Leu Asp Ser Asp Gly Ser Phe Phe Leu Tyr Ser Lys
                275                   280                   285

Leu Thr Val Asp Lys Ser Arg Trp Gln Gln Gly Asn Val Phe Ser Cys
    290                   295                   300

Ser Val Met His Glu Ala Leu His Asn Arg Phe Thr Gln Lys Ser Leu
305                   310                   315                   320

Ser Leu Ser Pro Gly Lys
                325
```

<210> SEQ ID NO 186
<211> LENGTH: 327
<212> TYPE: PRT
<213> ORGANISM: Artificial Sequence
<220> FEATURE:
<223> OTHER INFORMATION: synthetic

<400> SEQUENCE: 186

```
Ala Ser Thr Lys Gly Pro Ser Val Phe Pro Leu Ala Pro Cys Ser Arg
1                   5                     10                    15

Ser Thr Ser Glu Ser Thr Ala Ala Leu Gly Cys Leu Val Lys Asp Tyr
                20                    25                    30

Phe Pro Glu Pro Val Thr Val Ser Trp Asn Ser Gly Ala Leu Thr Ser
                35                    40                    45

Gly Val His Thr Phe Pro Ala Val Leu Gln Ser Ser Gly Leu Tyr Ser
    50                    55                    60

Leu Ser Ser Val Val Thr Val Pro Ser Ser Ser Leu Gly Thr Lys Thr
```

-continued

```
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 187
<211> LENGTH: 327
<212> TYPE: PRT
<213> ORGANISM: Artificial Sequence
<220> FEATURE:
<223> OTHER INFORMATION: synthetic

<400> SEQUENCE: 187

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
```

-continued

```
              100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn Arg Phe Thr Gln Lys Ser
305                 310                 315                 320

Leu Ser Leu Ser Leu Gly Lys
                325

<210> SEQ ID NO 188
<211> LENGTH: 329
<212> TYPE: PRT
<213> ORGANISM: Artificial Sequence
<220> FEATURE:
<223> OTHER INFORMATION: synthetic

<400> SEQUENCE: 188

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
```

-continued

```
        130              135              140

Val Val Asp Val Ser Gln Glu Asp Pro Glu Val Gln Phe Asn Trp Tyr
145              150              155              160

Val Asp Gly Val Glu Val His Asn Ala Lys Thr Lys Pro Arg Glu Glu
            165              170              175

Gln Phe Asn Ser Thr Tyr Arg Val Val Ser Val Leu Thr Val Leu His
            180              185              190

Gln Asp Trp Leu Asn Gly Lys Glu Tyr Lys Cys Lys Val Ser Asn Lys
            195              200              205

Gly Leu Pro Ser Ser Ile Glu Lys Thr Ile Ser Lys Ala Lys Gly Gln
            210              215              220

Pro Arg Glu Pro Gln Val Tyr Thr Leu Pro Pro Ser Arg Asp Glu Leu
225              230              235              240

Thr Lys Asn Gln Val Ser Leu Thr Cys Leu Val Lys Gly Phe Tyr Pro
            245              250              255

Ser Asp Ile Ala Val Glu Trp Glu Ser Asn Gly Gln Pro Glu Asn Asn
            260              265              270

Tyr Lys Thr Thr Pro Pro Val Leu Asp Ser Asp Gly Ser Phe Phe Leu
            275              280              285

Tyr Ser Lys Leu Thr Val Asp Lys Ser Arg Trp Gln Gln Gly Asn Val
            290              295              300

Phe Ser Cys Ser Val Met His Glu Ala Leu His Asn His Tyr Thr Gln
305              310              315              320

Lys Ser Leu Ser Leu Ser Pro Gly Lys
            325
```

```
<210> SEQ ID NO 189
<211> LENGTH: 329
<212> TYPE: PRT
<213> ORGANISM: Artificial Sequence
<220> FEATURE:
<223> OTHER INFORMATION: synthetic

<400> SEQUENCE: 189
```

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Lys Val Glu Pro Lys Ser Cys Asp Lys Thr His Thr Cys Pro Pro Cys
            100             105             110

Pro Ala Pro Pro Val Ala Gly Pro Ser Val Phe Leu Phe Pro Pro Lys
            115             120             125

Pro Lys Asp Thr Leu Met Ile Ser Arg Thr Pro Glu Val Thr Cys Val
            130             135             140

Val Val Asp Val Ser Gln Glu Asp Pro Glu Val Gln Phe Asn Trp Tyr
145             150             155             160

Val Asp Gly Val Glu Val His Asn Ala Lys Thr Lys Pro Arg Glu Glu
```

```
                      165               170               175

Gln Phe Asn Ser Thr Tyr Arg Val Val Ser Val Leu Thr Val Leu His
                180               185               190

Gln Asp Trp Leu Asn Gly Lys Glu Tyr Lys Cys Lys Val Ser Asn Lys
                195               200               205

Gly Leu Pro Ser Ser Ile Glu Lys Thr Ile Ser Lys Ala Lys Gly Gln
        210               215               220

Pro Arg Glu Pro Gln Val Tyr Thr Leu Pro Pro Ser Arg Asp Glu Leu
225               230               235               240

Thr Lys Asn Gln Val Ser Leu Thr Cys Leu Val Lys Gly Phe Tyr Pro
                245               250               255

Ser Asp Ile Ala Val Glu Trp Glu Ser Asn Gly Gln Pro Glu Asn Asn
                260               265               270

Tyr Lys Thr Thr Pro Pro Val Leu Asp Ser Asp Gly Ser Phe Phe Leu
                275               280               285

Tyr Ser Lys Leu Thr Val Asp Lys Ser Arg Trp Gln Gln Gly Asn Val
        290               295               300

Phe Ser Cys Ser Val Met His Glu Ala Leu His Asn Arg Phe Thr Gln
305               310               315               320

Lys Ser Leu Ser Leu Ser Pro Gly Lys
                325

<210> SEQ ID NO 190
<211> LENGTH: 326
<212> TYPE: PRT
<213> ORGANISM: Artificial Sequence
<220> FEATURE:
<223> OTHER INFORMATION: synthetic

<400> SEQUENCE: 190

Ala Ser Thr Lys Gly Pro Ser Val Phe Pro Leu Ala Pro Cys Ser Arg
1               5               10               15

Ser Thr Ser Glu Ser Thr Ala Ala Leu Gly Cys Leu Val Lys Asp Tyr
                20               25               30

Phe Pro Glu Pro Val Thr Val Ser Trp Asn Ser Gly Ala Leu Thr Ser
        35               40               45

Gly Val His Thr Phe Pro Ala Val Leu Gln Ser Ser Gly Leu Tyr Ser
        50               55               60

Leu Ser Ser Val Val Thr Val Pro Ser Ser Ser Leu Gly Thr Lys Thr
65               70               75               80

Tyr Thr Cys Asn Val Asp His Lys Pro Ser Asn Thr Lys Val Asp Lys
                85               90               95

Arg Val Glu Ser Lys Tyr Gly Pro Pro Cys Pro Pro Cys Pro Ala Pro
                100               105               110

Pro Val Ala Gly Pro Ser Val Phe Leu Phe Pro Pro Lys Pro Lys Asp
        115               120               125

Thr Leu Met Ile Ser Arg Thr Pro Glu Val Thr Cys Val Val Val Asp
        130               135               140

Val Ser Gln Glu Asp Pro Glu Val Gln Phe Asn Trp Tyr Val Asp Gly
145               150               155               160

Val Glu Val His Asn Ala Lys Thr Lys Pro Arg Glu Glu Gln Phe Asn
                165               170               175

Ser Thr Tyr Arg Val Val Ser Val Leu Thr Val Leu His Gln Asp Trp
                180               185               190

Leu Asn Gly Lys Glu Tyr Lys Cys Lys Val Ser Asn Lys Gly Leu Pro
```

-continued

```
                195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Arg
                275                 280                 285

Leu Thr Val Asp Lys Ser Arg Trp Gln Glu Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 191
<211> LENGTH: 326
<212> TYPE: PRT
<213> ORGANISM: Artificial Sequence
<220> FEATURE:
<223> OTHER INFORMATION: synthetic

<400> SEQUENCE: 191

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
                195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Glu Met Thr Lys Asn
```

-continued

```
225                230                235                240

Gln Val Ser Leu Thr Cys Leu Val Lys Gly Phe Tyr Pro Ser Asp Ile
                245                250                255

Ala Val Glu Trp Glu Ser Asn Gly Gln Pro Glu Asn Asn Tyr Lys Thr
                260                265                270

Thr Pro Pro Val Leu Asp Ser Asp Gly Ser Phe Phe Leu Tyr Ser Arg
                275                280                285

Leu Thr Val Asp Lys Ser Arg Trp Gln Glu Gly Asn Val Phe Ser Cys
                290                295                300

Ser Val Met His Glu Ala Leu His Asn Arg Phe Thr Gln Lys Ser Leu
305                310                315                320

Ser Leu Ser Leu Gly Lys
                325
```

```
<210> SEQ ID NO 192
<211> LENGTH: 232
<212> TYPE: PRT
<213> ORGANISM: Artificial Sequence
<220> FEATURE:
<223> OTHER INFORMATION: synthetic

<400> SEQUENCE: 192

Glu Pro Lys Ser Cys Asp Lys Thr His Thr Cys Pro Pro Cys Pro Ala
1                5                10                15

Pro Glu Leu Leu Gly Gly Pro Ser Val Phe Leu Phe Pro Pro Lys Pro
                20                25                30

Lys Asp Thr Leu Met Ile Ser Arg Thr Pro Glu Val Thr Cys Val Val
                35                40                45

Val Asp Val Ser His Glu Asp Pro Glu Val Lys Phe Asn Trp Tyr Val
                50                55                60

Asp Gly Val Glu Val His Asn Ala Lys Thr Lys Pro Arg Glu Glu Gln
65                70                75                80

Tyr Asn Ser Thr Tyr Arg Val Val Ser Val Leu Thr Val Leu His Gln
                85                90                95

Asp Trp Leu Asn Gly Lys Glu Tyr Lys Cys Lys Val Ser Asn Lys Ala
                100                105                110

Leu Pro Ala Pro Ile Glu Lys Thr Ile Ser Lys Ala Lys Gly Gln Pro
                115                120                125

Arg Glu Pro Gln Val Tyr Thr Leu Pro Pro Ser Arg Asp Glu Leu Thr
                130                135                140

Lys Asn Gln Val Ser Leu Thr Cys Leu Val Lys Gly Phe Tyr Pro Ser
145                150                155                160

Asp Ile Ala Val Glu Trp Glu Ser Asn Gly Gln Pro Glu Asn Asn Tyr
                165                170                175

Lys Thr Thr Pro Pro Val Leu Asp Ser Asp Gly Ser Phe Phe Leu Tyr
                180                185                190

Ser Lys Leu Thr Val Asp Lys Ser Arg Trp Gln Gln Gly Asn Val Phe
                195                200                205

Ser Cys Ser Val Met His Glu Ala Leu His Asn His Tyr Thr Gln Lys
                210                215                220

Ser Leu Ser Leu Ser Pro Gly Lys
225                230
```

```
<210> SEQ ID NO 193
<211> LENGTH: 232
<212> TYPE: PRT
```

<213> ORGANISM: Artificial Sequence
<220> FEATURE:
<223> OTHER INFORMATION: synthetic

<400> SEQUENCE: 193

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn Arg Phe Thr Gln Lys
        210                 215                 220

Ser Leu Ser Leu Ser Pro Gly Lys
225                 230
```

<210> SEQ ID NO 194
<211> LENGTH: 228
<212> TYPE: PRT
<213> ORGANISM: Artificial Sequence
<220> FEATURE:
<223> OTHER INFORMATION: synthetic

<400> SEQUENCE: 194

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95
```

-continued

```
Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                    165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225
```

```
<210> SEQ ID NO 195
<211> LENGTH: 228
<212> TYPE: PRT
<213> ORGANISM: Artificial Sequence
<220> FEATURE:
<223> OTHER INFORMATION: synthetic

<400> SEQUENCE: 195
```

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                    85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                    165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn Arg Phe Thr Gln Lys Ser Leu Ser Leu
            210                 215                 220
```

-continued

```
Ser Pro Gly Lys
225

<210> SEQ ID NO 196
<211> LENGTH: 229
<212> TYPE: PRT
<213> ORGANISM: Artificial Sequence
<220> FEATURE:
<223> OTHER INFORMATION: synthetic

<400> SEQUENCE: 196

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn Arg Phe Thr Gln Lys Ser Leu Ser
    210                 215                 220

Leu Ser Leu Gly Lys
225

<210> SEQ ID NO 197
<211> LENGTH: 229
<212> TYPE: PRT
<213> ORGANISM: Artificial Sequence
<220> FEATURE:
<223> OTHER INFORMATION: synthetic

<400> SEQUENCE: 197

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 198
<211> LENGTH: 231
<212> TYPE: PRT
<213> ORGANISM: Artificial Sequence
<220> FEATURE:
<223> OTHER INFORMATION: synthetic

<400> SEQUENCE: 198

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190
```

-continued

```
Lys Leu Thr Val Asp Lys Ser Arg Trp Gln Gln Gly Asn Val Phe Ser
    195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 199
<211> LENGTH: 231
<212> TYPE: PRT
<213> ORGANISM: Artificial Sequence
<220> FEATURE:
<223> OTHER INFORMATION: synthetic

<400> SEQUENCE: 199

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
    195                 200                 205

Cys Ser Val Met His Glu Ala Leu His Asn Arg Phe Thr Gln Lys Ser
    210                 215                 220

Leu Ser Leu Ser Pro Gly Lys
225                 230

<210> SEQ ID NO 200
<211> LENGTH: 228
<212> TYPE: PRT
<213> ORGANISM: Artificial Sequence
<220> FEATURE:
<223> OTHER INFORMATION: synthetic

<400> SEQUENCE: 200

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
```

-continued

```
                    20                  25                  30

Met Ile Ser Arg Thr Pro Glu Val Thr Cys Val Val Val Asp Val Ser
                35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly Lys
225
```

<210> SEQ ID NO 201
<211> LENGTH: 228
<212> TYPE: PRT
<213> ORGANISM: Artificial Sequence
<220> FEATURE:
<223> OTHER INFORMATION: synthetic

<400> SEQUENCE: 201

```
Glu Ser Lys Tyr Gly Pro Pro Cys Pro Pro Cys Pro Ala Pro Pro Val
1                   5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
```

-continued

```
145                    150                    155                    160

Glu Trp Glu Ser Asn Gly Gln Pro Glu Asn Asn Tyr Lys Thr Thr Pro
                165                    170                    175

Pro Val Leu Asp Ser Asp Gly Ser Phe Phe Leu Tyr Ser Arg Leu Thr
                180                    185                    190

Val Asp Lys Ser Arg Trp Gln Glu Gly Asn Val Phe Ser Cys Ser Val
            195                    200                    205

Met His Glu Ala Leu His Asn Arg Phe Thr Gln Lys Ser Leu Ser Leu
    210                    215                    220

Ser Leu Gly Lys
225
```